US005665357A

United States Patent [19]
Rose et al.

[11] Patent Number: 5,665,357
[45] Date of Patent: Sep. 9, 1997

[54] ANTIBODIES RECOGNIZING TUMOR ASSOCIATED ANTIGEN CA 55.1

[75] Inventors: Michael Samuel Rose, Wilmslow; Christopher Boot, Northwich; Clive Graham Copley; Douglas Stephen Paterson, both of Macclesfield; Susan Margaret Hall, Adlington; Andrew Firman Wright; David Charles Blakey, both of Macclesfield, all of United Kingdom

[73] Assignee: Zeneca Limited, London, United Kingdom

[21] Appl. No.: 353,400

[22] Filed: Dec. 2, 1994

[30] Foreign Application Priority Data

Dec. 3, 1993 [GB] United Kingdom .............. 9324819
Jun. 3, 1994 [GB] United Kingdom .............. 9411089

[51] Int. Cl.⁶ ............ A61K 39/395; C07K 19/00; G01N 33/53; C12N 5/12
[52] U.S. Cl. ............ 424/178.1; 530/387.1; 530/300; 530/328; 530/387.3; 530/388.8; 530/391.3; 530/391.7; 530/391.9; 536/23.53; 435/320.1; 435/252.3; 435/344; 435/7.92; 435/69.7; 435/91.1; 435/172.1; 435/172.3; 435/331; 435/332; 435/344.1; 424/183.1; 424/130.1; 424/181.1; 424/182.1
[58] Field of Search ............ 424/130.1, 133.1, 424/152.1, 155.1, 156.1, 179.1, 180.1, 181.1, 182.1, 183.1, 178.1; 435/7.92, 69.7, 91.1, 172.2, 240.27, 240.1, 252.3, 320.1; 530/387.1, 300, 328, 387.3, 388.8, 391.3, 391.7, 391.9; 536/23.53

[56] References Cited

U.S. PATENT DOCUMENTS 4,867,973  9/1989  Goers et al. .................. 424/85.91

FOREIGN PATENT DOCUMENTS 289 400    9/1987  European Pat. Off. ......... C07K 15/06
89/08114   9/1989  WIPO ............................ C07K 17/02

OTHER PUBLICATIONS

Oldenburg et al., "Peptide ligands for a sugar–binding protein isolated from a random peptide library", Proc. Natl. Acad. Sci. USA, vol. 89, pp. 5393–5397, Jun. 1992.

Scott et al., "A family of concanavalin A–binding peptides from a hexapeptide epitope library", Proc. Natl. Acad. Sci. USA, vol. 89, pp. 5398–5402, Jun. 1992.

Hoess et al., "Identification of a peptide which binds to the carbohydrate–specific monoclonal antibody B3", Gene, 128 (1993) 43–49.

Parmley et al., "Antibody–selectable filamentous fd phage vectors: affinity purification of target genes", Gene, 73 (1988) 305–318.

Durbin et al., "An Epitope On Carcinoembryonic Antigen Defined By The Clinically Relevant Antibody PR1A3", Proc. Natl. Acad. Sci. USA, vol. 91, pp. 4313–4317, May 1994.

Hellstrom et al., "Highly Tumor–reactive, Internalizing, Mouse Monoclonal Antibodies to Leʸ–related Cell Surface Antigens", Cancer Research 50, 2183–2190, Apr. 1, 1990.

Ouyang et al., "CEA And Carbohydrate Antigens In Normal And Neoplastic Colon Mucosa", Acta Path. Microbiolo. Immunol. Scand. Sect. A. 95:177–183, 1987.

Kuusela et al., "Comparison Of A New Tumour Marker CA 242 With CA 19–9, CA 50 and Carcinoembryonic Antigen (CEA) In Digestive Tract Diseases", Int. J. Cancer (1991) 636–640.

Roberts et al., "Value of Different Tumor Markers In Colorectal Cancer", Cancer of the Breast—Status and Trends in Diagnosis and Therapy, 1992, pp. 30–32.

Muraro et al., "A Monoclonal Antibody (D612) With Selective Reactivity For Malignant and Normal Gastro–Intestinal Epithelium", Int. J. Cancer: 43, 598–607 (1989).

Zhang et al., "Monoclonal Antibody Recognizing A Carcinoembryonic Antigen Epitope Differentially Expressed In Human Colonic Carcinoma Versus Normal Adult Colon Tissues", Can. Res. 48, 5766–5773, 1988.

Gold et al., "Murine Monoclonal Antibodies To Colon–Specific Antigen p¹", Cancer Research 50, 6405–6409, Oct. 1, 1990.

Bleday et al., "Characterization Of A New Monoclonal Antibody To A Cell Surface Antigen On Colorectal Cancer and Fetal Gut Tissues", Cancer 57:433–440, 1986.

Verstijnen et al., "Colonic Epithelium Reactive Monoclonal Antibodies", Histochemistry (1989) 92:397–406.

Pant et al., "COTA (Colon–Ovarian Tumor Antigen), An Immunohistochemical Study", Am. J. Clin. Pathol. 1986, 86:1–9.

(List continued on next page.)

*Primary Examiner*—Frank C. Eisenschenk
*Attorney, Agent, or Firm*—Cushman Darby & Cushman Intellectual Property Group of Pillsbury Madison & Sutro, LLP

[57] ABSTRACT

Antibodies which recognize a tumor related antigen designated CA55.1 such as hybridoma 55.1 deposited as ECACC deposit no. 93081901 in which the complementarity determining regions have the following sequences:

a) heavy chain
 CDR1 G Y W I H (SEQ ID NO: 27)
 CDR2 E V N P S T G R S D Y N E K F K N (SEQ ID NO: 28)
 CDR3 E R A Y G Y D D A M D Y (SEQ ID NO: 29)
b) light chain
 CDR1 K S S Q S L L N S R T R K N Y L A (SEQ ID NO: 30)
 CDR2 W A S T R T S (SEQ ID NO: 31)
 CDR3 K Q S Y T L R T (SEQ ID NO: 32)

or a conservative analogue thereof. The peptide ACEHRGS-GWC (SEQ ID NO: 26), as displayed on the surface of bacteriophage NCIMB No. 40638, is a mimic of the tumor related antigen CA55.1.

15 Claims, 19 Drawing Sheets

OTHER PUBLICATIONS

Molinolo et al., "Enhanced Tumor Binding Using Immunohistochemical Analyses By Second Generation Anti-Tumor-Associated Glycoprotein 72 Monoclonal Antibodies versus Monoclonal Antibody B72.3 In Human Tissue", Cancer Research, 50, 1291–1298, Feb. 15, 1990.

Gottlinger et al., "Biochemical Characterization and Tissue Distribution Of The Core Antigen, A Cell Surface Glycoprotein Differentially Expressed on Malignant and Benign Gastrointestinal Epithelia", Cancer Research, 1988 48:2198–2203.

Richman et al., "Monoclonal Antibodies To Human Colorectal Epithelium: Markers For Differentiation And Tumour Characterization", Int. J. Cancer: 39, 317–328 (1987).

Takahashi et al., "In Vivo Localization Of Human Colon Adenocarcinoma By Monoclonal Antibody Binding To A Highly Expressed Cell Surface Antigen", Cancer Research 48, 6573–6579, Nov. 15, 1988.

Drewinko et al., "New Monoclonal Antibodies Against Colon Cancer–Associated Antigens", Cancer Research 46, 5137–5143, Oct. 1986.

Magnani et al., "A Monoclonal Antibody–Defined Antigen Associated With Gastrointestinal Cancer Is A Ganglioside Containing Sialylated Lacto–N–fucopentaose II", J. Bio. Chem., vol. 257, No. 23, 1982, pp. 14365–14369.

Kuroki et al. "Serological Mapping Of The TAG–27–Tumor–Associated Antigen Using 19 Distinct Monclonal Antibodies", Cancer Research 50, 4872–4879, Aug. 15, 1990.

Byers et al., "Inhibition of Growth of Human Tumor Xenografts in Athymic Mice Treated With Ricin Toxin A Chain–Monoclonal Antibody 791T/36 Conjugates", Cancer Research 47, 5042–5046, Oct. 1, 1987.

Larson et al., "Mouse Monoclonal Antibodies For Experimental Immunotherapy Promotes Killing of Tumor Cells", Int. J. Cancer: 42, 877–882 (1988).

Johansson et al., "Comparison of Serological Expression of Different Epitopes On the CA50–Carrying Antigen CanAg", Int. J. Cancer: 48, 000–000 (1991).

Shetye et al ., "Tumor–Associated Antigens Common To Humans and Chemically Induced Colonic Tumors of the Rat", Cancer Research 50, 6358–6363, Oct. 1, 1990.

Magnani et al, "Identification of the Gastrointestinal and Pancreatic Cancer–Associated Antigen Detected By Monoclonal Antibody 19–9 in the Sera of Patients as a Mucin", Cancer Research 43, 5489–5492, Nov. 1983.

Queen et al. [PNAS 86:10029–10033 (1989)].

Waldmann [Science 252:1657–1662 (1991)].

Harris et al. [TIBTECH 11:42–44 (1993)].

Osband et al. [Immunotherapy 11(6):193–195 (1990)].

Dillman [Ann. Internal Med. 111:592–600 (1989)].

Hird et al. [Genes and Cancer (1990) chapter 17].

Curti [Critical Reviews in Oncology/Hematology 14:29–39 (1993)].

Cunningham et al. [TIBTECH 10(4):112–113 (1992)].

Kettleborough et al. [Protein Engineering 4(7):773–783 (1991)].

Riechmann et al. [Nature 332:323–327 (1988)].

GROWTH AND PRODUCTIVITY OF 55.1 IN 5% FBS

GROWTH AND PRODUCTIVITY OF 55.1 IN PROTEIN FREE MEDIUM

Map of Plasmid pICI1646

Anti-Tumour Effect of 55.1-Ricin A Chain Immunoconjugate on Colo 205 Tumour Bearing Nude Mice Figure 6. Western Blot. Lane 1 COLO205 membrane preparation, Lane 2 PNGase F treated COLO205 membrane preparation and Lane 3 Sialidase treated COLO205 membrane preparation. Lane 4 contains molecular weight markers.

Fig.7.
A
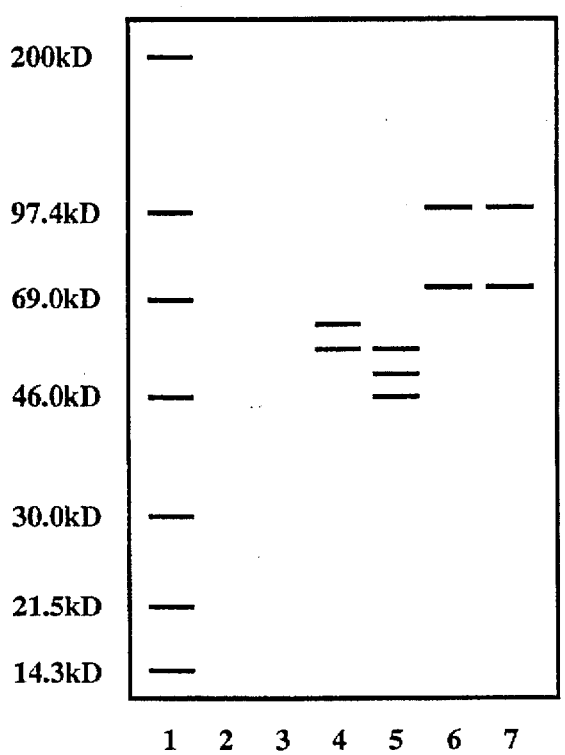
B
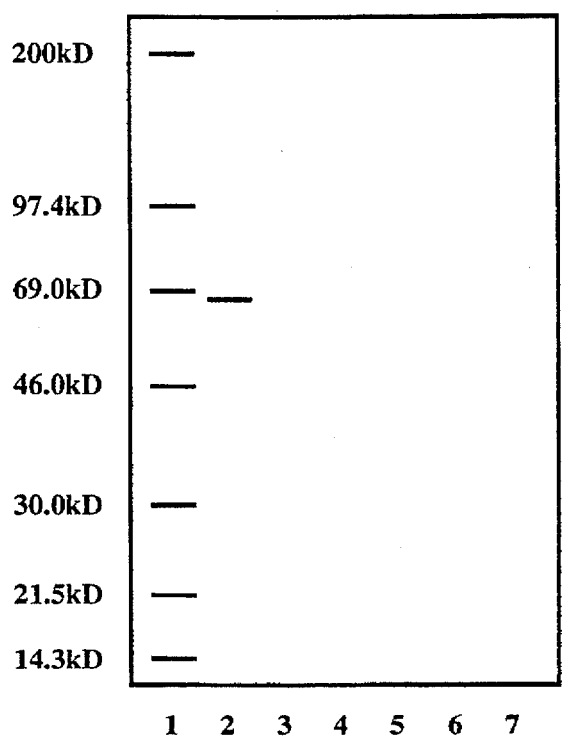
Figure 7. Shows the results of Western Blots with A). Lectin DSA and B). Lectin GNA. The Lanes 1-7 contain the following samples;
1. Molecular weight markers. 2. Carboxypeptidase Y. 3. Transferrin.
4. Fetuin. 5. Asialofetuin. 6. COLO205 membrane preparation.
7. COLO205 membane preparation at x5 loading.

MAP OF pRc/CMV

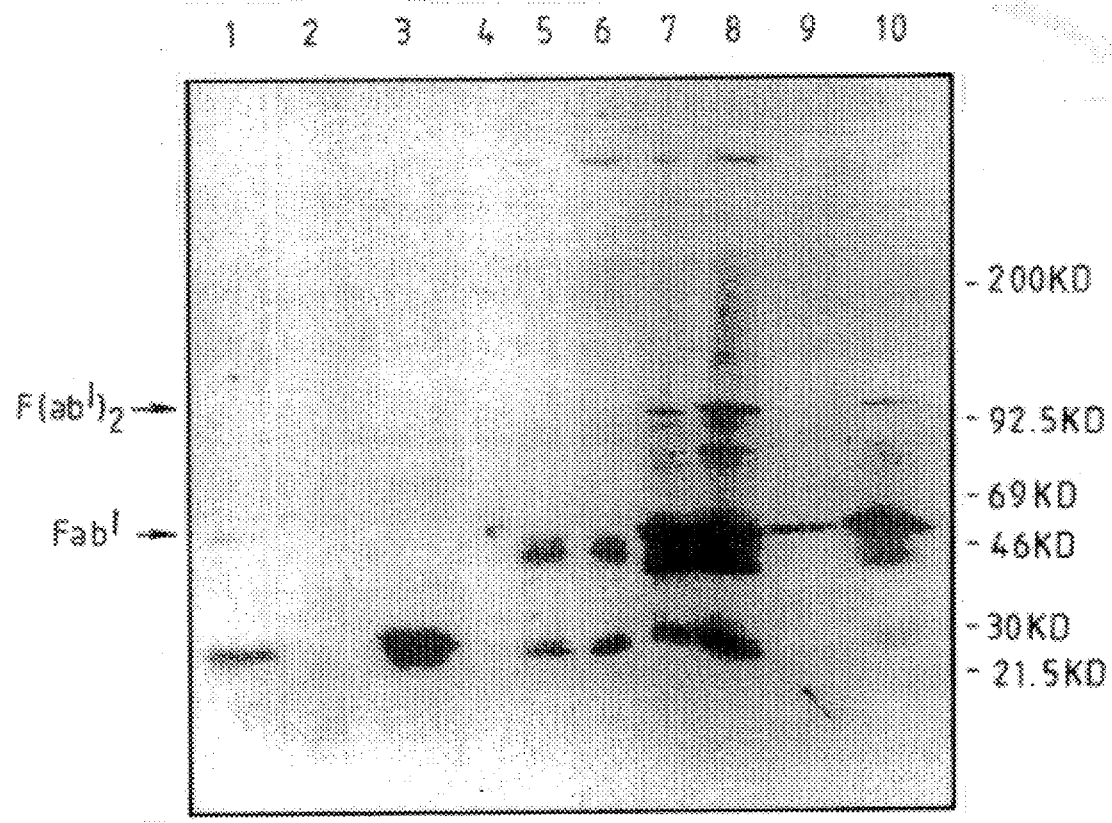
Fig. 9. WESTERN BLOT SHOWING Fab' AND F(ab')$_2$ EXPRESSION
KEY
1 - MC1000(pICI1656) before induction + DTT
2 - MC1000(pICI1656) after induction + DTT
3 - MC1061(pICI1656) before induction + DTT
4 - MC1061(pICI1656) after induction + DTT
5-6 - alternative antibody after induction - DTT
7-8 - hybrid antibody after induction - DTT
9 - MC1000(pICI1656) after induction -DTT
10 - MC1061(pICI1656) after induction - DTT

Fig. 10. ELISA SHOWING Fab' AND F(ab')₂ BINDING

Optical Density

|   | 1 | 2 | 3 | 4 | 5 | 6 | 7 | 8 | 9 | 10 | 11 | 12 |
|---|---|---|---|---|---|---|---|---|---|---|---|---|
| A | 0.124 | 0.111 | 0.097 | 0.099 | 0.105 | 0.108 | 0.098 | 0.128 | 0.124 | 0.127 | 0.224 | 0.247 |
| B | 0.183 | 0.329 | 0.218 | 0.261 | 0.248 | 0.248 | 0.187 | 0.224 | 0.233 | 0.212 | 0.197 | 0.190 |
| C | 0.332 | 0.365 | 0.194 | 0.203 | 0.176 | 0.186 | 0.155 | 0.185 | 0.227 | 0.203 | 0.198 | 0.190 |
| D | 0.220 | 0.196 | 0.141 | 0.145 | 0.161 | 0.176 | 0.145 | 0.130 | 0.129 | 0.148 | 0.099 | 0.178 |
| E | 0.137 | 0.125 | 0.090 | 0.084 | 0.096 | 0.096 | 0.098 | 0.105 | 0.150 | 0.157 | 0.167 | 0.162 |
| F | 0.680 | 0.677 | 0.358 | 0.439 | 0.242 | 0.330 | 0.270 | 0.315 | 0.249 | 0.236 | 0.155 | 0.168 |
| G | 0.599 | 0.553 | 0.411 | 0.433 | 0.279 | 0.382 | 0.275 | 0.306 | 0.209 | 0.215 | 0.155 | 0.166 |
| H | 0.386 | 0.235 | 0.225 | 0.266 | 0.177 | 0.176 | 0.161 | 0.182 | 0.141 | 0.145 | 0.123 | 0.172 |

KEY

A3-10   MC1000(pICI1656) before induction, 3&4 neat, 5&6 1 in 2, 7&8 1 in 4 etc.

C1-10   MC1000(pICI1656) after induction, 1&2 neat, 3&4 1 in 2, 5&6 1 in 4 etc.

E3-8   MC1061(pICI1656) before induction

G1-10   MC1061(pICI1656) after induction

B1-10 & F1-10   hybrid antibody after induction

D1-10 & H1-10 alternative antibody after induction

A-G 11&12   anti-COLO205 antibody standard, A 5µg/ml, B 2.5µg/ml, C 1.25µg/ml etc.

Remaining wells - reagent blanks

WESTERN BLOT SHOWING scFv EXPRESSION

KEY

1 - scFv in MC1000 before induction

2 - scFv in MC1000 after induction

3 - scFv in MC1061 before induction

4 - scFv in MC1061 after induction

Fig.12. ELISA SHOWING scFv BINDING

Optical Density

|   | 1 | 2 | 3 | 4 | 5 | 6 | 7 | 8 | 9 | 10 | 11 | 12 |
|---|---|---|---|---|---|---|---|---|---|----|----|----|
| A | 0.356 | 0.357 | 0.480 | 0.473 | 0.477 | 0.505 | 0.476 | 0.399 | 0.461 | 0.416 | 2.130 | 2.223 |
| B | 0.321 | 0.416 | 0.495 | 0.527 | 0.598 | 0.534 | 0.530 | 0.576 | 0.536 | 0.340 | 1.109 | 1.055 |
| C | 0.342 | 0.318 | 0.353 | 0.380 | 0.456 | 0.422 | 0.350 | 0.491 | 0.279 | 0.433 | 0.761 | 0.690 |
| D | 0.292 | 0.347 | 0.350 | 0.359 | 0.218 | 0.366 | 0.339 | 0.346 | 0.339 | 0.351 | 0.572 | 0.488 |
| E | 0.316 | 0.385 | 0.520 | 0.398 | 0.502 | 0.504 | 0.449 | 0.473 | 0.434 | 0.474 | 0.481 | 0.395 |
| F | 0.518 | 0.473 | 0.647 | 0.505 | 0.570 | 0.579 | 0.530 | 0.574 | 0.486 | 0.573 | 0.364 | 0.359 |
| G | 0.314 | 0.362 | 0.334 | 0.394 | 0.387 | 0.360 | 0.358 | 0.409 | 0.396 | 0.384 | 0.388 | 0.326 |
| H | 0.320 | 0.294 | 0.347 | 0.367 | 0.484 | 0.470 | 0.464 | 0.392 | 0.438 | 0.384 | 0.205 | 0.319 |

KEY

A1&2, D&G1-10, H11&12 - reagent blanks

A3-10 MC1000(pICI1657) before induction,
3&4 neat, 5&6 1 in 2, 7&8 1 in 4 etc..

B1-10 MC1000(pICI1657) after induction,
1& 2 neat, 3&4 1 in 2 etc..

E3-10 MC1061(pICI1657) before induction

F1-10 MC1061(pICI1657) after induction

C & H1-10 alternative scFv after induction

A-G11&12 anti-COLO205 antibody standard,
A11&12 5µg/ml, B11&12 2.5µg/ml,
C11&12 1.25µg/ml etc..

Specificity of Direct Binding of ACEHRGSGWC Phage to MAb 55.1

- □ ACEHRGSGWC Phage on MAb 55.1
- ● ACEHRGSGWC Phage on MAb 19.9
- ■ ACEHRGSGWC Phage on MAb C242

Specificity of ACEHRGSGWC Phage in Colo 205 Competition Assay

— □ —  ACEHRGSGWC Phage on MAb 55.1
— ◆ —  ACEHRGSGWC Phage vs MAb 19.9
— ■ —  ACEHRGSGWC Phage vs MAb C242

Fig.15.

Complete DNA sequence of 55.1 H chain cDNA with protein translation

```
GAATTCGCGGCCGCCAGTTCTCTCTACAGTTACTGAGCACACAGGACCTCACCATGGGAT
                                                          MetGlyT

GGAGCTATATCATCCTCTTTTTGGTAGCAACAGGTACAGATGTCCACTCCCAGGTCCAAC
rpSerTyrIleIleLeuPheLeuValAlaThrGlyThrAspValHisSer
                                                    Q  V  Q  L

TGCAGCAGCCTGGGGCTGAACTGGTGAAGCCTGGGGCTTCAGTGCAGCTGTCCTGCAAGG
 Q  Q  P  G  A  E  L  V  K  P  G  A  S  V  Q  L  S  C  K  A

CTTCTGGCTACACCTTCACCGGCTACTGGATACACTGGGTGAAGCAGAGGCCTGGACAAG
 S  G  Y  T  F  T  G  Y  W  I  H  W  V  K  Q  R  P  G  Q  G

GCCTTGAGTGGATTGGAGAGGTTAATCCTAGTACCGGTCGTTCTGACTACAATGAGAAGT
 L  E  W  I  G  E  V  N  P  S  T  G  R  S  D  Y  N  E  K  F

TCAAGAACAAGGCCACACTGACTGTAGACAAATCCTCCACCACAGCCTACATGCAACTCA
 K  N  K  A  T  L  T  V  D  K  S  S  T  T  A  Y  M  Q  L  S

GCAGCCTGACATCTGAGGACTCTGCGGTCTATTACTGTGCAAGAGAGAGGGCCTATGGTT
 S  L  T  S  E  D  S  A  V  Y  Y  C  A  R  E  R  A  Y  G  Y

ACGACGATGCTATGGACTACTGGGGTCAAGGAACCTCAGTCACCGTCTCCTCTGCCAAAA
 D  D  A  M  D  Y  W  G  Q  G  T  S  V  T  V  S  S  A  K  T

CGACACCCCCATCTGTCTATCCACTGGCCCCTGGATCTGCTGCCCAAACTAACTCCATGG
 T  P  P  S  V  Y  P  L  A  P  G  S  A  A  Q  T  N  S  M  V

TGACCCTGGGATGCCTGGTCAAGGGCTATTTCCCTGAGCCAGTGACAGTGACCTGGAACT
 T  L  G  C  L  V  K  G  Y  F  P  E  P  V  T  V  T  W  N  S

CTGGATCCCTGTCCAGCGGTGTGCACACCTTCCCAGCTGTCCTGCAGTCTGACCTCTACA
 G  S  L  S  S  G  V  H  T  F  P  A  V  L  Q  S  D  L  Y  T

CTCTGAGCAGCTCAGTGACTGTCCCCTCCAGCACCTGGCCCAGCGAGACCGTCACCTGCA
 L  S  S  S  V  T  V  P  S  S  T  W  P  S  E  T  V  T  C  N

ACGTTGCCCACCCGGCCAGCAGCACCAAGGTGGACAAGAAAATTGTGCCCAGGGATTGTG
 V  A  H  P  A  S  S  T  K  V  D  K  K  I  V  P  R  D  C  G
```

Fig.15(Cont).

```
GTTGTAAGCCTTGCATATGTACAGTCCCAGAAGTATCATCTGTCTTCATCTTCCCCCCAA
 C  K  P  C  I  C  T  V  P  E  V  S  S  V  F  I  F  P  P  K

AGCCCAAGGATGTGCTCACCATTACTCTGACTCCTAAGGTCACGTGTGTTGTGGTAGACA
 P  K  D  V  L  T  I  T  L  T  P  K  V  T  C  V  V  V  D  I

TCAGCAAGGATGATCCCGAGGTCCAGTTCAGCTGGTTTGTAGATGATGTGGAGGTGCACA
 S  K  D  D  P  E  V  Q  F  S  W  F  V  D  D  V  E  V  H  T

CAGCTCAGACGCAACCCCGGGAGGAGCAGTTCAACAGCACTTTCCGCTCAGTCAGTGAAC
 A  Q  T  Q  P  R  E  E  Q  F  N  S  T  F  R  S  V  S  E  L

TTCCCATCATGCACCAGGACTGGCTCAATGGCAAGGAGTTCAAATGCAGGGTCAACAGTG
 F  P  I  M  H  Q  D  W  L  N  G  K  E  F  K  C  R  V  N  S

CAGCTTTCCCTGCCCCCATCGAGAAAACCATCTCCAAAACCAAAGGCAGACCGAAGGCTC
 A  A  F  P  A  P  I  E  K  T  I  S  K  T  K  G  R  P  K  A  P

CACAGGTGTACACCATTCCACCTCCCAAGGAGCAGATGGCCAAGGATAAAGTCAGTCTGA
 Q  V  Y  T  I  P  P  P  K  E  Q  M  A  K  D  K  V  S  L  T

CCTGCATGATAACAGACTTCTTCCCTGAAGACATTACTGTGGAGTGGCAGTGGAATGGGC
 C  M  I  T  D  F  F  P  E  D  I  T  V  E  W  Q  W  N  G  Q

AGCCAGCGGAGAACTACAAGAACACTCAGCCCATCATGGACACAGATGGCTCTTACTTCG
 P  A  E  N  Y  K  N  T  Q  P  I  M  D  T  D  G  S  Y  F  V

TCTACAGCAAGCTCAATGTGCAGAAGAGCAACTGGGAGGCAGGAAATACTTTCACCTGCT
 Y  S  K  L  N  V  Q  K  S  N  W  E  A  G  N  T  F  T  C  S

CTGTGTTACATGAGGGCCTGCACAACCACCATACTGAGAAGAGCCTCTCCCACTCTCCTG
 V  L  H  E  G  L  H  N  H  H  T  E  K  S  L  S  H  S  P  G

GTAAATGATCCCAGTGTCCTTGGAGCCCTCTGGTCCTACAGGACTCTGACACCTACCTCC
 K  *

ACCCCTCCCTGTATAAATAAAGCACCCAGCACTGCCTTGGGACCCTGCAAAAAAAAAAA

AAAAAAAAGCGGCCGCGAATTC
```

Fig. 16.

Complete DNA sequence of 55.1 L chain cDNA with protein translation

```
GAATTCGCGGCCGCGATGGATTCACAGGCCCAGGTTCTTATATTGCTGCTGCTATGGGTA
              MetAspSerGlnAlaGlnValLeuIleLeuLeuLeuLeuTrpVal

TCTGGAACCTGTGGGGACATTGTGATGTCACAGTCTCCATCCTCCCTGGCTGTGTCAGCA
SerGlyThrCysGly
              D  I  V  M  S  Q  S  P  S  S  L  A  V  S  A

GGAGAGAAGGTCACCATGAGCTGCAAATCCAGTCAGAGTCTCCTCAACAGTAGAACCCGA
G  E  K  V  T  M  S  C  K  S  S  Q  S  L  L  N  S  R  T  R

AAGAACTACTTGGCTTGGTACCAGCAGAGACCAGGGCAGTCTCCTAAACTGCTGATCTAT
K  N  Y  L  A  W  Y  Q  Q  R  P  G  Q  S  P  K  L  L  I  Y

TGGGCATCCACTAGGACATCTGGGGTCCCTGATCGCTTCACAGGCAGTGGATCTGGGACA
W  A  S  T  R  T  S  G  V  P  D  R  F  T  G  S  G  S  G  T

GATTTCACTCTCACCATCAGCAGTGTGCAGGCTGAAGACCTGGCAATTTATTACTGCAAG
D  F  T  L  T  I  S  S  V  Q  A  E  D  L  A  I  Y  Y  C  K

CAATCTTATACTCTTCGGACGTTCGGTGGAGGCACCAAGCTGGAAATCAAACGGGCTGAT
Q  S  Y  T  L  R  T  F  G  G  G  T  K  L  E  I  K  R  A  D

GCTGCACCAACTGTATCCATCTTCCCACCATCCAGTGAGCAGTTAACATCTGGAGGTGCC
A  A  P  T  V  S  I  F  P  P  S  S  E  Q  L  T  S  G  G  A

TCAGTCGTGTGCTTCTTGAACAACTTCTACCCCAAAGACATCAATGTCAAGTGGAAGATT
S  V  V  C  F  L  N  N  F  Y  P  K  D  I  N  V  K  W  K  I

GATGGCAGTGAACGACAAAATGGCGTCCTGAACAGTTGGACTGATCAGGACAGCAAAGAC
D  G  S  E  R  Q  N  G  V  L  N  S  W  T  D  Q  D  S  K  D

AGCACCTACAGCATGAGCAGCACCCTCACGTTGACCAAGGACGAGTATGAACGACATAAC
S  T  Y  S  M  S  S  T  L  T  L  T  K  D  E  Y  E  R  H  N

AGCTATACCTGTGAGGCCACTCACAAGACATCAACTTCACCCATTGTCAAGAGCTTCAAC
S  Y  T  C  E  A  T  H  K  T  S  T  S  P  I  V  K  S  F  N

AGGAATGAGTGTTAGAGACAAAGGTCCTGAGACGCCACCACCAGCTCCCCAGCTCCATCC
R  N  E  C  *
```

Fig.16(Cont).

TATCTTCCCCTTCTAAGGTCTTGGAGGCTTCCCCACAAGCGACCTACCACTGTTGCGGTG

CTCCAAACCTCCTCCCCACCTCCTTCTCCTCCTCCTCCCTTTCCTTGGCTTTTATCATGC

TAATATTTGCAGAAAATATTCAATAAAGTGAGTCTTTGGCGGCCGCGAATTC

FLOWCHART FOR GENERATION OF ANTIBODIES TO 55.1 ANTIGEN

Fig.18.

DNA sequence of the c-myc tag

TCGAGATCAA ACGGGAACAA AAACTCATCT CAGAAGAGGA TCTGAATTAA TAATGATCAA

CTAGTT TGCCCTTGTT TTTGAGTAGA GTCTTCTCCT AGACTTAATT ATTACTAGTT

ACGGTAATAA GGATCCAGCT CG

TGCCATTATT CCTAGGTCGA GCTTAA

ANTIBODIES RECOGNIZING TUMOR ASSOCIATED ANTIGEN CA 55.1 PROTEINS

The present invention relates to a novel tumour associated antigen (CA55.1) useful for the diagnosis and therapy of cancer.

It is established that the transformation of normal tissue cells to tumour cells is associated with a change in carbohydrate structure on the cell surface. Many such cell surface carbohydrate structures serve as antigens and the tumour modified structures represent a type of so-called tumour-associated antigen (see Altered Glycosylation in Tumour Cells, eds Reading, Hakamori and Marcus 1988 Arthur R. Liss publ.). Such antigens may be exploited for example by the generation of monospecific antibodies using hybridoma technology. Hybridoma technology for the isolation and production of monclonal antibodies is presently well established and was first described by Kohler and Milstein (Nature, 256, 495–497, 1975).

Tumour-associated antigens have been reported in relation to human tumour diseases for example, CEA (carcinoma embryonic antigen, Gold and Freedman, J Exp Med, 121, 439, 1965), GICA (gastrointestinal cancer antigen) carrying the CA19.9 epitope, and the C242.2 epitope on CA50 (Larson et al, Int J Cancer, 42, 877–882, 1988) have been demonstrated, particularly in gastrointestinal carcinomas. All these antigens are present on the tumour cell surface and can also be demonstrated in the blood serum.

The concept of using such antibodies to target tumour associated antigens in the treatment of cancer has been appreciated for over 10 years (Herlyn et. al. (1980) Cancer Research 40, 717). Antibodies may be used to target various chemical and biological agents to the tumour and such conjugates have been particularly successful in forming the basis for many methods of both in vitro and in vivo diagnosis. The use of immunoconjugates in the therapy of cancer is also promising (Lord et al (1985) Trends in Biotechnology 3, 175; Vitetta et al (1987) Science 238, 1098). This approach is technically more demanding than diagnostic applications and requires that tumour associated antigens which are targetted in such immunotherapeutic approaches, are highly tumour specific and not expressed at significant levels in vital human tissues. As well as the property of having specific tumour associated tissue distribution, the metabolic fate of the antigen in the tumour cell itself is also an important property. It has been found that the potency of various conjugates of monoclonal antibodies and their derivatives is dependent on rates of internalization of the tumour associated antigen from the membrane surface of the cell. In particular certain conjugates, namely immunotoxins, require rapid and continuous internalization of the antigen molecule from the surface of the tumour cell in order to be effective pharmaceutically. For immunotoxin or drug conjugate related uses a high rate of internalization or endocytosis is desirable but for other uses such as antibody directed enzyme prodrug therapy or radiotherapy it is not an essential characteristic.

To be useful in the treatment of cancer it is believed that a tumour specific antigen must generally be: 1) expressed in significant levels on the surface of the majority of tumour cells (generally >10 000 molecules per cell) and; 2) expressed at low levels or be undetectable on vital normal tissues.

There is a need for further and improved tumour specific antigens useful in cancer diagnosis and therapy.

The present invention is based on the discovery of the tumour associated antigen designated CA55.1 (as defined herein). The antigen exhibits several properties which make it a superior target for immunotherapy or diagnosis of certain cancers than known tumour specific antigens. It is expressed in a majority of colorectal tumours and is only weakly expressed or absent in normal colonic tissue. Furthermore, following antibody binding to cell bound CA55.1 the complex so formed is endocytosed or internalised into the tumour cells at a high rate.

According to one aspect of the present invention there is provided an antigen binding structure having complementarity determining regions (CDRs) recognising antigen CA55.1 in which the antigen possesses:
  a) three dominant species having molecular weights by SDS-PAGE in the ranges about 48 to 52 kD, about 58 kD to 72 kD and about 88 kD to 92 kd;
  b) a subcellular location in the membrane fraction of COLO 205 tumour cells (ATCC No CCL 222);
  c) a complex N-linked carbohydrate structure;
and wherein the antigen binding structure has at least one of the following properties:
  i) the antigen binding structure competitively inhibits binding of monoclonal antibody 55.1 (ECACC No. 93081901) to the CA55.1 antigen or;
  ii) the peptide ACEHRGSGWC (SEQ ID NO: 26), as displayed on the surface of bacteriophage NCIMB No. 40638, binds to the antigen binding structure with an effective binding of 10 pM or less when incubated with solid phase coated antigen binding structure or;
  iii) the peptide ACEHRGSGWC (SEQ ID NO: 26), as displayed on the surface of bacteriophage NCIMB No 40638, at an effective concentration of 200 nM or less, when preincubated with the antigen binding structure, competitively inhibits the binding of the antigen binding structure to solid phase coated Colo 205 cells (ATCC No. CCL 222).

Lectin binding studies on the purified CA55.1 antigen demonstrate that the CA55.1 carbohydrate is an N-linked oligosaccharide of the complex type without sialic acid residues linked $\alpha(2-6)$ or $\alpha(2-3)$ to galactose. A test for recognition of CA55.1 (by competitive inhibition of binding of antibody 55.1) is set out in Example 7 hereinafter. Tests for measurement of binding in the presence of ACEHRGSGWC phage (SEQ ID No 26) are set out in Example 14. A subcellular location in the membrane fraction means that the antigen is present on a membrane fraction produced from whole cells by a method such as that described in Example 7.1a.

In the search for novel antagonists of the binding of MAb 55.1 to its antigen, libraries of M13 bacteriophage displaying random peptide sequences on the N-terminus of the phage minor coat protein pIII were generated and screened against MAb 55.1 immobilised on polystyrene. As a result of such screening, a phage displaying the sequence ACEHRGSGWC (single letter amino acid code; (SEQ ID No 26) at the N-terminus of pIII was found to inhibit the attachment of MAb 55.1 to its antigen on Colo 205 cells.

There are already examples in the literature of peptide mimetics being selected from phage peptide display libraries screened against carbohydrate-binding proteins, including peptide ligands for the mannose-binding protein concanavalin A (con A) (Scott et al, Proc. Natl. Acad. Sci. USA, vol 89, pp. 5398–5402, 1992; also Oldenburg et al, Proc. Natl. Acad. Sci. USA, vol 89, pp. 5393–5397, 1992), and an anti-carbohydrate MAb (Hoess et al, Gene, vol 128, pp. 43–49, 1993). The independent results of the two groups studying con A showed strong consensus in the peptide sequences selected, including the repeated motif YPY; screening against the MAb resulted in selection of a repeated motif PWLY. There has been some speculation that the aromatic side-chains selected by both carbohydrate-binding proteins stack against each other in a similar stereochemical configuration to sugar rings. In contrast, the structure selected by MAb 55.1 lacks the hydrophobic and conformational properties of the ligands described above, was selected from a nominally cyclic peptide library, and no selection was observed on screening MAb 55.1 against linear peptide libraries generated in-house (the other groups selected binders from linear peptide libraries). A search for the sequence ACEHRGSGWC in protein sequence databases has failed to show homology to any known peptides, hence the sequence bound by MAb 55.1 is novel.

An antigen binding structure is generally an antibody (or fragment thereof or modified antibody construct such as scFv) and is defined as any protein sequence which will recognize and bind CA55.1 antigen. Preferably binding affinity for CA55.1 antigen is at least 10E–5M, more preferably binding affinity for CA55.1 antigen is at least 10E–6M, more preferably binding affinity for CA55.1 antigen is at least 10E–7M, more preferably binding affinity for CA55.1 antigen is at least 10E–8M, more preferably binding affinity for CA55.1 antigen is at least 10E–9M, more preferably binding affinity for CA55.1 antigen is at least 10E–10M and especially binding affinity for CA55.1 antigen is at least 10E–11M. The protein sequence of the antigen binding structure is normally derived from an immunoglobulin or immunoglobulin domain of the immunoglobulin super gene family and may be either the complete natural molecule, a fragment thereof or a species engineered to retain only those structural features of the immunoglobulin fold which allow productive binding to the antigen. Preferably the antigen binding structure is based on the CDRs of antibody 55.1. The CDRs or complementarity determining regions are those sequences within the hypervariable loops of antibody variable domains which are assumed to be critical in determining the specificity of the antigen-antibody interaction (Kabat et al (1987) in Sequences of Proteins of Immunological Interest, US Depy Health and Human Services, Washington D.C.); CDRs as defined herein however includes framework residues where these contribute to binding. For the antibody 55.1 the CDRs were determined by homology with the hypervariable sequences of other murine antibodies.

The Heavy Chain CDRs are:

1 pos 31–35 inc.=G Y W I H (SEQ ID NO: 27)

2 pos 50–66 inc=E V N P S T G R S D Y N E K F K N (SEQ ID NO: 28)

3 pos 99–110 inc=E R A Y G Y D D A M D Y (SEQ ID NO: 29)

The Light Chain CDRs are:

1 pos 24–40 inc=K S S Q S L L N S R T R K N Y L A (SEQ ID NO: 30)

2 pos 56–62 inc=W A S T R T S (SEQ ID NO: 31)

3 pos 95–102 inc=K Q S Y T L R T (SEQ ID NO: 32)

According to one aspect of the present invention there is provided an antigen binding structure having complementarity determining regions (CDRs) recognising antigen CA55.1 in which the CDRs have the following sequences:

a) heavy chain

CDR1 G Y W I H (SEQ ID NO: 27)

CDR2 E V N P S T G R S D Y N E K F K N (SEQ ID NO: 28)

CDR3 E R A Y G Y D D A M D Y (SEQ ID NO: 29);

b) light chain

CDR1 K S S Q S L L N S R T R K N Y L A (SEQ ID NO: 30)

CDR2 W A S T R T S (SEQ ID NO: 31)

CDR3 K Q S Y T L R T (SEQ ID NO: 32)

or a conservative analogue thereof.

According to one aspect of the present invention there is provided an antigen binding structure having the following, optionally humanised, structure:

a heavy chain sequence (SEQ ID NO: 33)

Gln Val Gln Leu Gln Gln Pro Gly Ala Glu Leu Val Lys Pro Gly Ala

Ser Val Gln Leu Ser Cys Lys Ala Ser Gly Tyr Thr Phe Thr Gly Tyr

Trp Ile His Trp Val Lys Gln Arg Pro Gly Gln Gly Leu Glu Trp Ile

Gly Glu Val Asn Pro Ser Thr Gly Arg Ser Asp Tyr Asn Glu Lys Phe

Lys Asn Lys Ala Thr Leu Thr Val Asp Lys Ser Ser Thr Thr Ala Tyr

Met Gln Leu Ser Ser Leu Thr Ser Glu Asp Ser Ala Val Tyr Tyr Cys

Ala Arg Glu Arg Ala Tyr Gly Tyr Asp Asp Ala Met Asp Tyr Trp Gly

Gln Gly Thr Ser Val Thr Val Ser Ser Ala Lys Thr Thr Pro Pro Ser

Val Tyr Pro Leu Ala Pro Gly Ser Ala Ala Gln Thr Asn Ser Met Val

Thr Leu Gly Cys Leu Val Lys Gly Tyr Phe Pro Glu Pro Val Thr Val

Thr Trp Asn Ser Gly Ser Leu Ser Ser Gly Val His Thr Phe Pro Ala

Val Leu Gln Ser Asp Leu Tyr Thr Leu Ser Ser Ser Val Thr Val Pro

Ser Ser Thr Trp Pro Ser Glu Thr Val Thr Cys Asn Val Ala His Pro

Ala Ser Ser Thr Lys Val Asp Lys Lys Ile Val Pro Arg Asp Cys Gly

Cys Lys Pro Cys Ile Cys Thr Val Pro Glu Val Ser Ser Val Phe Ile

Phe Pro Pro Lys Pro Lys Asp Val Leu Thr Ile Thr Leu Thr Pro Lys

-continued

| | | | | | | | | | | | | | |
|---|---|---|---|---|---|---|---|---|---|---|---|---|---|
| Val | Thr | Cys | Val | Val | Val | Asp | Ile | Ser | Lys | Asp | Asp | Pro | Glu | Val | Gln |
| Phe | Ser | Trp | Phe | Val | Asp | Asp | Val | Glu | Val | His | Thr | Ala | Gln | Thr | Gln |
| Pro | Arg | Glu | Glu | Gln | Phe | Asn | Ser | Thr | Phe | Arg | Ser | Val | Ser | Glu | Leu |
| Pro | Ile | Met | His | Gln | Asp | Trp | Leu | Asn | Gly | Lys | Glu | Phe | Lys | Cys | Arg |
| Val | Asn | Ser | Ala | Ala | Phe | Pro | Ala | Pro | Ile | Glu | Lys | Thr | Ile | Ser | Lys |
| Thr | Lys | Gly | Arg | Pro | Lys | Ala | Pro | Gln | Val | Tyr | Thr | Ile | Pro | Pro | Pro |
| Lys | Glu | Gln | Met | Ala | Lys | Asp | Lys | Val | Ser | Leu | Thr | Cys | Met | Ile | Thr |
| Asp | Phe | Phe | Pro | Glu | Asp | Ile | Thr | Val | Glu | Trp | Gln | Trp | Asn | Gly | Gln |
| Pro | Ala | Glu | Asn | Tyr | Lys | Asn | Thr | Gln | Pro | Ile | Met | Asp | Thr | Asp | Gly |
| Ser | Tyr | Phe | Val | Tyr | Ser | Lys | Leu | Asn | Val | Gln | Lys | Ser | Asn | Trp | Glu |
| Ala | Gly | Asn | Thr | Phe | Thr | Cys | Ser | Val | Leu | His | Glu | Gly | Leu | His | Asn |
| His | His | Thr | Glu | Lys | Ser | Leu | Ser | His | Ser | Pro | Gly | Lys | | | | and;
a light chain sequence (SEQ ID NO: 34):

sp Ile Val Met Ser Gln Ser Pro Ser Ser Leu Ala Val Ser Ala Gly
Glu Lys Val Thr Met Ser Cys Lys Ser Ser Gln Ser Leu Leu Asn Ser
Arg Thr Arg Lys Asn Tyr Leu Ala Trp Tyr Gln Gln Gln Pro Gly Gln
Ser Pro Lys Leu Leu Ile Tyr Trp Ala Ser Thr Arg Thr Ser Gly Val
Pro Asp Arg Phe Thr Gly Ser Gly Ser Gly Thr Asp Phe Thr Leu Thr
Ile Ser Ser Val Gln Ala Glu Asp Leu Ala Ile Tyr Tyr Cys Lys Gln
Ser Tyr Thr Leu Arg Thr Phe Gly Gly Gly Thr Lys Leu Glu Ile Lys
Arg Ala Asp Ala Ala Pro Thr Val Ser Ile Phe Pro Pro Ser Ser Glu
Gln Leu Thr Ser Gly Gly Ala Ser Val Val Cys Phe Leu Asn Asn Phe
Tyr Pro Lys Asp Ile Asn Val Lys Trp Lys Ile Asp Gly Ser Glu Arg
Gln Asn Gly Val Leu Asn Ser Trp Thr Asp Gln Asp Ser Lys Asp Ser
Thr Tyr Ser Met Ser Ser Thr Leu Thr Leu Thr Lys Asp Glu Tyr Glu
Arg His Asn Ser Tyr Thr Cys Glu Ala Thr His Lys Thr Ser Thr Ser
Pro Ile Val Lys Ser Phe Asn Arg Asn Glu Cys;

or any one of the following constructs thereof:

F(ab')2; F(ab'), Fab, Fv, single chain Fv & V-min or; a conservative analogue thereof.

According to another aspect of the present invention there is provided a polynucleotide sequence coding for the heavy or light chain variable region of an antibody which hybridises under stringent conditions to a polynucleotide sequence coding for CDR3 of the heavy or light chain of antibody 55.1 (ECACC deposit no. 93081901).

Preferably the polynucleotide codes for two (especially three) CDRs of the heavy or light chain of antibody 55.1. A hybridisation test is set out in Example 10 hereinafter.

According to one aspect of the present invention there is provided a polynucleotide sequence encoding at least the variable region of the heavy chain or a light chain of an antigen binding structure as hereinbefore defined.

According to another aspect of the present invention there is provided an antigen binding structure having a sequence encoded by a polynucleotide sequence as defined hereinbefore.

According to another aspect of the present invention there is provided an antigen binding structure having at least one CDR3 of antibody 55.1 (ECACC deposit no. 93081901) or a conservative analogue thereof. Preferably the antigen binding structure has at least 3 CDRs (more preferably 4 CDRs, more preferably 5 CDRs and especially 6 CDRs) of antibody 55.1 or conservative analogues thereof.

A conservative analogue is a protein sequence which retains the binding properties of the antigen binding structure but differs in sequence by one or more conservative amino acid substitutions. For the purposes of this document a conservative amino acid substitution is a substitution whose probability of occurring in nature is greater than ten times the probability of that substitution occurring by chance (as defined by the computational methods described by Dayhoff et al, Atlas of Protein Sequence and Structure, 1971, page 95–96 and FIGS. 9–10).

According to another aspect of the present invention there is provided an antibody having an antigen binding structure as hereinbefore described.

According to another aspect of the present invention there is provided an antibody or antibody fragment as hereinbefore described characterised in that it is humanised.

A humanized antibody, related fragment or antibody binding structure is a polypeptide composed largely of a structural framework of human derived immunoglobulin sequences supporting non human derived amino acid sequences in and around the antigen binding site (complementarity determining regions or CDRs). Appropriate methodology has been described for example in detail in WO 91/09967, EP 0328404 and Queen et al. Proc Natl Acad Sci 86,10029, Mountain and Adair (1989) Biotechnology and Genetic Engineering Reviews 10, 1 (1992) although alternative methods of humanisation are also contemplated such as antibody veneering of surface residues (EP 519596, Merck/NIH, Padlan et al). Preparation of chimaeric humanised antibody fragments of antibody 55.1 is described in Example 3 herein.

According to another aspect of the present invention there is provided a host cell transformed with a polynucleotide sequence or a transgenic non-human animal or transgenic plant developed from the host cell in which the polynucloetide sequence encodes at least the variable region of the heavy chain or light chain of an antigen binding structure as hereinbefore defined.

According to another aspect of the present invention there is provided hybridoma 55.1 deposited as ECACC deposit no. 93081901 and variant cell lines thereof.

Hybridoma 55.1 was deposited at the European Collection of Animal Cell Cultures (ECACC), PHLS Centre for Applied Microbiology & Research, Porton Down, Salisbury, Wiltshire SP4 0JG, United Kingdom on 19 Aug. 1993 under deposit reference no. 93081901 in accordance with the Budapest Treaty.

According to another aspect of the present invention there is provided ACEHRGSGWC phage deposited as NCIMB No. 40638 and variants thereof.

ACEHRGSGWC phage was deposited at The National Collections of Industrial and Marine Bacteria, 23 St Machar Drive, Aberdeen AB2 1RY, Scotland, United Kingdom on 10 May 1994 under deposit reference number NCIMB 40638 in accordance with the Budapest Treaty.

According to another aspect of the present invention there is provided a method of making at least a variable region of a heavy or light chain of an antigen binding structure as hereinbefore defined comprising:

a) transforming a host cell with a polynucleotide sequence which encodes at least the variable region of the heavy or light chain of the antigen binding structure and optionally developing the transformed host cell into a transgenic non-human mammal or transgenic plant;

b) subjecting the host cell, transgenic non-human mammal or transgenic plant to conditions conducive to expression, and optionally secretion, of at least the variable region and optionally;

c) at least partially purifying the variable region.

Preferably both heavy and light chain variable regions are expressed in the same cell and assembled thereby to form an antigen binding structure.

According to another aspect of the present invention there is provided a method of making monoclonal antibody 55.1 comprising:

a) culturing hybridoma 55.1 deposited as ECACC deposit no. 93081901 in medium under conditions conducive to expression of antibody therefrom and;

b) obtaining antibody 55.1 from the culture medium and optionally;

c) preparing a F(ab')2 fragment of antibody 55.1 by enzymic digestion.

According to another aspect of the present invention there is provided a conjugate which comprises an effector moiety (preferably a toxin, but also an enzyme or radioactive ligand) and an antigen binding structure or antibody as hereinbefore described.

It will be appreciated that the conjugate of the present invention does not necessarily consist of one effector molecule and one antibody molecule. For example the conjugate may comprise more than one effector molecule per antibody molecule.

When the effector molecule is a toxin, this toxin moiety generally comprises a component which possesses cytotoxic properties and hence is capable of killing cells following internalisation.

The toxin moiety and the antigen binding structure may be coupled directly to one another, or they may be coupled indirectly. The toxin moiety and the antigen binding structure are, in general, coupled such that the geometry of the conjugate permits the antigen binding structure to bind to its target cell. Advantageously, the toxin moiety and the antigen binding structure are coupled such that the conjugate is extracellularly stable, and intracellularly unstable so that the toxin moiety and the antigen binding structure remain coupled outside the target cell, but following internalisation, the toxin moiety is released. Thus, advantageously the conjugate has an intracellularly cleavable/extracellularly stable site.

Examples of conjugates in which the toxin moiety is directly coupled to the target cell binding moiety include those in which the toxin moiety and the antigen binding structure are coupled by a disulphide bridge formed between a thiol group on the toxin moiety and a thiol group on the antigen binding structure. Details of the preparation and properties of immunotoxins and other conjugates are given in European patent application EP 528 527 (publication no.) the contents of which is incorporated herein by reference thereto.

According to another aspect of the present invention there is provided a pharmaceutical composition comprising an immunotoxin as described hereinbefore.

It will be appreciated that the dose and dosage regimen will depend upon the particular toxin moiety employed, the population of the target cell and the patient's history. The dose of the conjugate administered will typically be in the range 0.1 to 1 mg/kg of patient weight.

The conjugates of the present invention will normally be administered in the form of a pharmaceutical composition. Thus according to the present invention there is also provided a pharmaceutical compostion which comprises a conjugate (as defined herein) in association with a pharmaceutically-acceptable diluent or carrier. An example of such a formulation is given herein in Example 9.

Pharmaceutical compositions of the present invention may be formulated in a variety of dosage forms. Generally, the conjugates of the present invention will be administered parenterally, preferably intravenously. A particular parenteral pharmaceutical composition is one which is formulated in a unit dosage form which is suitable for administration by injection. Thus, particularly suitable compositions comprise a solution, emulsion or suspension of the immunotoxin in association with a pharmaceutically acceptable parenteral carrier or diluent. Suitable carriers or diluents include aqueous vehicles, for example water or saline, and non-aqueous vehicles, for example fixed oils or liposomes. The compositions may include agents which enhance the stability of the conjugate in the composition. For example, the composition may include a buffer, for example Tween.

The concentration of the conjugate will vary, but in general, the conjugate will be formulated at concentrations of about 1 to 10 mg/dose.

The antibody 55.1 is selective for pancreatic and colorectal tumour cells and conjugates incorporating this antibody have been found to be potent immunotoxins which are selective for colorectal tumour cells.

According to another aspect of the present invention there is provided an expression vector coding for an antigen binding structure as herein defined.

According to another aspect of the present invention there is provided an expression vector encoding at least the variable region of a heavy or light chain of an antigen binding structure as hereinbefore defined.

Mammalian cells (CHO, COS, myeloma) have been used as host for the co-expression of antibody H and L chain cDNAs and fragments thereof to produce protein with the specified binding activity (Bebbington, C., 1991, Methods, vol 2, p136–145, and Adair, J., 1992, Immunological Reviews, vol 130). The cDNAs can be introduced on plasmids and allowed to integrate into chromosomal DNA. The plasmids require a selectable marker for maintenance in transfected hosts, an efficient eukaryotic promoter to allow a high level of transcription from the cDNAs, convenient restriction enzyme sites for cloning and polyadenylation and transcription termination signals for message stabilty. Several such vectors have been described in the literature (Bebbington, C. et al, 1992, Bio/Technology, vol 10, p169–175, and Wright, A., 1991, Methods, vol 2, p125–135) and there are commercially available vectors, such as pRc/CMV (Invitrogen Corp., see FIG. 8), which fulfil the necessary criteria.

The expression of a range of antibody fragments in E. coli is well documented (reviewed by Pluckthun, A., Immunological Reviews, 1992, vol 130, p151–188 and Skerra, A., Current Opinion in Immunology, 1993, vol 5, p256–262). Intracellular expression of Fd and L chains has been described (Cabilly, S., 1989, Gene, vol 85, p553–557) but this may require in vitro refolding and re-association of the chains (Buchner, J and Rudolph, R., 1991, Bio/Technology, vol 9, p157–162) to produce binding activity. A more efficient route to obtaining active antibody fragments is through periplasmic secretion (Better, M. et al, 1988, Science, vol 240, p1041–1043). The H and L chain components of the antibody fragment are co-expressed from a single plasmid. Each antibody chain is provided with a bacterial leader peptide which directs it to the E. coli periplasm where the leader is cleaved and the free chains associate to produce soluble and active antibody fragments. This process is believed to mimic the natural process in eukaryotic cells where the expressed antibody chains pass into the lumen of the ER prior to association into whole antibodies. This process often results in the presence of binding activity in the culture supernatant.

According to another aspect of the present invention there is provided a host cell transformed with a vector as hereinbefore described which is compatible with expression therein.

According to another aspect of the present invention there is provided a host cell transformed with a polynucloetide sequence as hereinbefore defined.

According to another aspect of the present invention there is provided a method of making at least a variable region of a heavy or light chain of an antigen binding structure as hereinbefore defined comprising:

a) transforming a host cell with a polynucleotide sequence which encodes at least the variable region;

b) subjecting the host cell to conditions conducive to expression, and optionally secretion, of at least the variable region and optionally;

c) at least partially purifying the variable region.

Preferably both heavy and light chain variable regions are expressed in the same host cell and assembled thereby to form an antigen binding structure.

Some expression systems involve transforming a host cell with a vector; such systems are well known such as for example in E. coli, yeast and mammalian hosts (see Methods in Enzymology 185, Academic Press 1990). Other systems of expression are also contemplated such as for example transgenic non-human mammals in which the gene of interest, preferably cut out from a vector and preferably in association with a mammary promoter to direct expressed protein into the animal's milk, is introduced into the pronucleus of a mammalian zygote (usually by microinjection into one of the two nuclei (usually the male nucleus) in the pronucleus) and thereafter implanted into a foster mother. A proportion of the animals produced by the foster mother will carry and express the introduced gene which has integrated into a chromosome. Usually the integrated gene is passed on to offspring by conventional breeding thus allowing ready expansion of stock. Preferably the protein of interest is simply harvested from the milk of female transgenic animals. The reader is directed to the following publications: Simons et al. (1988), Bio/Technology 6:179–183; Wright et al. (1991) Bio/Technology 9:830–834; U.S. Pat. No. 4,873, 191 and; U.S. Pat. No. 5,322,775. Manipulation of mouse embryos is described in Hogan et al, "Manipulating the Mouse Embryo; A Laboratory Manual", Cold Spring Harbor Laboratory 1986.

Transgenic plant technology is also contemplated such as for example described in the following publications: Swain W. F. (1991) TIBTECH 9:107–109; Ma J. K. C. et al (1994) Eur. J. Immunology 24: 131–138; Hiatt A. et al (1992) FEBS Letters 307:71–75; Hein M. B. et al (1991) Biotechnology Progress 7:455–461; Duering K. (1990) Plant Molecular Biology 15: 281–294.

If desired, host genes can be inactivated or modified using standard procedures as outlined briefly below and as described for example in "Gene Targeting; A Practical Approach", IRL Press 1993. The target gene or portion of it is preferably cloned into a vector with a selection marker (such as Neo) inserted into the gene to disrupt its function. The vector is linearised then transformed (usually by electroporation) into embryonic stem (ES) cells (eg derived from a 129/01a strain of mouse) and thereafter homologous recombination events take place in a proportion of the stem cells. The stem cells containing the gene disruption are expanded and injected into a blastocyst (such as for example from a C57BL/6J mouse) and implanted into a foster mother for development. Chimeric offspring can be identified by coat colour markers. Chimeras are bred to ascertain the contribution of the ES cells to the germ line by mating to mice with genetic markers which allow a distinction to be made between ES derived and host blastocyst derived gametes. Half of the ES cell derived gametes will carry the gene modification. Offspring are screened (eg by Southern blotting) to identify those with a gene disruption (about 50% of progeny). These selected offspring will be heterozygous and therefore can be bred with another heterozygote and homozygous offspring selected thereafter (about 25% of progeny). Transgenic animals with a gene knockout can be crossed with transgenic animals produced by known techniques such as microinjection of DNA into pronuclei, sphaeroplast fusion (Jakobovits et al. (1993) Nature 362:255–258) or lipid mediated transfection (Lamb et al. (1993) Nature Genetics 5 22–29) of ES cells to yield transgenic animals with an endogenous gene knockout and foreign gene replacement.

ES cells containing a targeted gene disruption can be further modified by transforming with the target gene sequence containing a specific alteration, which is preferably cloned into a vector and linearised prior to transformation. Following homologous recombination the altered gene is introduced into the genome. These embryonic stem cells can subsequently be used to create transgenics as described above.

The term "host cell" includes any procaryotic or eucaryotic cell suitable for expression technology such as for example bacteria, yeasts, plant cells and non-human mammalian zygotes, oocytes, blastocysts, embryonic stem cells and any other suitable cells for transgenic technology. If the context so permits the term "host cell" also includes a transgenic plant or non-human mammal developed from transformed non-human mammalian zygotes, oocytes, blastocysts, embryonic stem cells, plant cells and any other suitable cells for transgenic technology.

According to another aspect of the present invention there is provided a method of making monoclonal antibody 55.1 comprising:

a) culturing hybridoma 55.1 deposited as ECACC deposit no. 93081901 and;

b) obtaining antibody 55.1 from the culture medium and optionally;

c) preparing a F(ab')2 fragment of antibody 55.1 by enzymic digestion.

According to another aspect of the present invention there is provided a method of treatment of a human or animal in need of such treatment which comprises of the administration to humans or animals of a pharmaceutically effective amount of an immunoconjugate as hereinbefore described.

According to another aspect of the present invention there is provided a method of targeting a toxin to cells displaying antigen CA55.1 in a mammal in need of such targeting which comprises administration of a pharmaceutically effective amount of an immunotoxin conjugate which comprises a toxin and an antigen binding structure as hereinbefore defined.

As mentioned herein, the conjugate is capable of killing gastrointestinal tumour cells. Thus the conjugate (or "immunotoxin") is able to deliver the toxin moiety to the tumour cell such that the toxin moiety may exert its cytotoxic properties. The conjugate will therefore, in general, be able to bind to the tumour cells (through the target cell binding moiety binding to the tumour cells) and allow the toxin moiety to pass into the cell, that is allow the toxin moiety to "internalise". Particularly effective conjugates will, in general, have the following properties:

1. The antigen binding structure should be capable of binding to a tumour cell surface antigen.

2. The cell surface antigen should be present in high copy number on tumour cells, for example, at least ten thousand per cell.

3. The antigen should not be expressed in high copy number on normal cells.

4. The antibody:antigen complex should be internalised efficiently such that the toxin moiety can exert its cytotoxicity intracellularly.

5. The conjugate should preferably be constructed such that it is sufficiently stable to remain intact in the blood for long enough to deliver the toxin moiety to the tumour cells as well as being sufficiently clearable to allow the release of the toxin moiety once the toxin moiety is inside the cell.

In general, the dose range for such a conjugate is determined as a proportion of an established toxic dose (eg the maximum tolerated dose). Commonly, this approach is used man also. Typically, the dose range would be 50–5000 µg/kg.

According to another aspect of the present invention there is provided the use of an antibody as hereinbefore described in a diagnostic method.

One diagnostic method is immunoassay. An immunoassay for in vitro testing based upon the novel antibody according to the invention may be designed in accordance with conventional immunological techniques in the art, utilising the antibody according to the invention in a labelled or unlabelled form and determining the complex formation of the antibody with specific antigenic species in the sample to be tested. In one case, the antibody may be labelled with a detectable label, such as radiolabel, a chemiluminescer, a fluorescer or an enzyme label. Alternatively the antibody is detected via a complex formed with a labelled substance or by non-labelling techniques, such as biosensor methods eg based upon surface plasmon resonance. The sample may, for example, be in the form of a body fluid, such as serum, or a tissue preparation (histochemical assay).

For in vivo diagnostic purposes, the antibody according to the invention is provided with a suitable externally detectable label, such as eg. a radiolabel or a heavy metal atom, and administered to a subject whereupon the possible localised accumulation of antibody in the body is determined.

For the in vitro diagnosis of cancer the antigen binding structure can be conjugated to either enzymes such as horse radish peroxidase and bacterial luciferase which can generate a signal which can be measured or to fluorescent markers or radioisotopes which can be detected and quantitated directly. In a standard immunoassay system such conjugates provide a means of measuring the presence or absence of CA55.1 in body tissues and consequently provides a rapid and convenient test for the diagnosis of tumour disease. See general descriptions of the methodology involved in Enzyme Immunoassay, E. T. Maggio, CRC Press and U.S. Pat. No. 3,690,8334, U.S. Pat. No. 3,791,932, U.S. Pat. No. 3,817,837, U.S. Pat. No. 3,850,578, U.S. Pat. No. 3,853,987, U.S. Pat. No. 3,867,517, U.S. Pat. No. 3,901,654, U.S. Pat. No. 3,935,074, U.S. Pat. No. 3,984,533, U.S. Pat. No. 3,996,345 and U.S. Pat. No. 4,098,876.

For the in vivo diagnosis of cancer, the antigen binding structure can be conjugated to isotopes of elements such as yttrium, tecnicium or indium or heavy metal isotopes which can be detected by whole body imaging cameras (see Larson, S. M. [1987] Radiology, 165, 297–304.

For the therapy of cancer, although the antigen binding structure could be used without further modification, the preferred embodiments involve an antigen binding structure that can be conjugated to toxic agents which can kill the cancer cells or the cells in the immediate vicinity of those cancer cells bearing the CA55.1 antigen. In the preferred embodiment the antigen binding structure is conjugated to a protein toxin such as ricin, diptheria toxin, Staphylococcal enterotoxin, Pseudomonas exotoxin, abrin or other ribosomal inactivating protein. These proteins may be linked to the antigen binding structure either chemically using a chemical cross linking agent or genetically by the construction of a fusion protein containing a single linear amino acid sequence of all or part of the antigen binding structure and all or part of the protein toxin. Because CA55.1 is rapidly internalized the protein toxin selectively enters the tumour cells and brings about their death.

Selective cell killing of tumour cells can also be achieved by conjugation of the antigen binding structure either directly or by chemical derivatization with macrocycle chelators containing high energy radioisotopes such as 90 Y, 131I and 111In. The antigen binding structure serves to localize the isotope to the tumour and the radiation emitted by the isotope destroys the DNA of the surrounding cells and kills the tumour.

Selective killing of tumour cells can also be achieved by conjugation of the antigen binding structure to cytotoxic and cytostatic drugs such as methotrexate, chlorambucil, adriamycin, daunorubicin and vincristine. These drugs have been used in the clinic for many years and the therapy they provide is often limited by non specific toxicity. Conjugation of these drugs to the CA55.1 antigen binding structure enables these drugs to localize at the tumour site and thus increasing the dose of drug that can be delivered to the tumour without incurring unacceptable side effects from the action of such drugs on other tissues such as the bone marrow or nervous system.

Selective killing of tumour cells can also be achieved by conjugating the antigen binding structure to an enzyme which is capable of catalysing the conversion of a non-toxic dose of a prodrug into a potent toxic drug compound. Administration of the conjugate leads to localization of the enzyme activity at the tumour site. Subsequent administration of the prodrug leads to local production of the toxic drug and selective kill at the tumour site. This approach is described in WO 88/07378, U.S. Pat. No. 4,975,278 and WO89/10140.

Another application is in the use of CA55.1 to isolate antigen binding structures which can be used to isolate further antibodies, idiotypic to CA55.1 specific antibodies. These antibodies can then be used as tumour vaccines to induce or boost a natural immune response to CA55.1 bearing tumours. An example of this approach is given in Nepom et. al. Proc. Natl. Acad. Sci. U.S. (1984) 81, 2864.

The technique for producing CA55.1 antigen binding structures is described in EXAMPLE 1 and EXAMPLE 2 and involves in the first instance the production of many thousands of monoclonal antibodies against a tumour cell carrying the antigen CA55.1 and then screening for those particular antibodies which specifically react with CA55.1 (EXAMPLE 6). This technology is generally practised using fusion of spleen cells from rodents which have been immunized with either the CA55.1 antigen or cells or membrane preparations of cells expressing the CA55.1 antigen such as COLO 205 (ATCC CCL 222, Can. Res. [1978] 38, 13455) and a parent myeloma cell line such as Sp/2 (ECACC Cat. No. 85110503, Methods in Enzymol [1981]73B, 3). The product of this fusion is a rodent hybriboma cell line which will express a rodent monoclonal antibody such as the murine IgG1 55.1 antibody. In the uses described above the most advantageous antigen binding structure for a particular application is not always the intact rodent monclonal antibody produced by the hybridoma fusion technology and the molecule is best modified further whilst retaining the original binding specificity for CA55.1.

In particular, the rodent antibody on repeated in vivo administration in man either as the antigen binding structure alone or as a conjugate will bring about an immune response in the recipient against the rodent antibody; the HAMA response. The HAMA response will limit the effectiveness of the pharmaceutical composition if repeated dosing is required. The immunogenicity of the antigen binding structure may be reduced by chemical modification of the antibody binding structure with a hydrophilic polymer such as polyethylene glycol or by using the methods of genetic engineering to make the antibody binding structure more human like. For example, the gene sequences for the variable domains of the rodent antibody which bind CA55.1 can be substituted for the variable domains of a human myeloma protein, thus producing a recombinant chimaeric antibody. These procedures are detailed in EP 194276, EP 0120694, EP 0125023, EP 0171496, EP 0173494 and WO 86/01533. Alternatively the gene sequences of the complementarity determining regions or CDR's of the CA55.1 binding rodent antibody may be isolated or synthesized and substituted for the corresponding sequence regions of a homologous human antibody gene, producing a human antibody with the specificity of the original rodent antibody. These procedures are described in EP 023940, WO 90/07861 and WO91/09967. Alternatively a large number of the surface residues of the variable domain of the rodent antibody may be changed to those residues normally found on a homologous human antibody, producing a rodent antibody which has a surface 'veneer' of residues and which will therefore be recognized as self by the human body. This approach has been demonstrated by Padlan et. al. (1991) Mol. Immunol. 28, 489.

The effectiveness of the antibody binding structure is in many applications improved by reducing the size of the antibody binding structure and thereby improving the tissue penetration and other pharmacodynamic properties of the pharmaceutical composition. This can be achieved by removing the Fc region of the antibody molecule either enzymically (EXAMPLE 4) or by genetic engineering methods to produce a recombinant Fab' or F(ab)2 fragment (Example 3.3).

Genetic engineering methods can also be used to further reduce the size of the antigen binding structure. The Fv which contain the CDRs can be engineered and expressed in isolation and chemically cross linked for instance by the use of disulphide bridges. Alternatively, both the light and heavy chain domains making up the Fv structure may be produced as a single polypeptide chain (SCFv) by fusing the Fv domains with a linker peptide sequence from the natural C-terminus of one domain to the N-terminus of the other domain (See EXAMPLE 3.3 and PCT/US/87/02208 and U.S. Pat. No. 4,704,692). Alternatively, a single Fv domain may be expressed in isolation forming a single domain antibody or dAb as described by Ward et al Nature(1989) 341,544. Another type of antigen binding structure is a V-min construct as disclosed in International Patent Application WO 94/12625 (inventors Slater & Timms).

The invention is illustrated by the following non-limiting examples in which.

Figure 8:
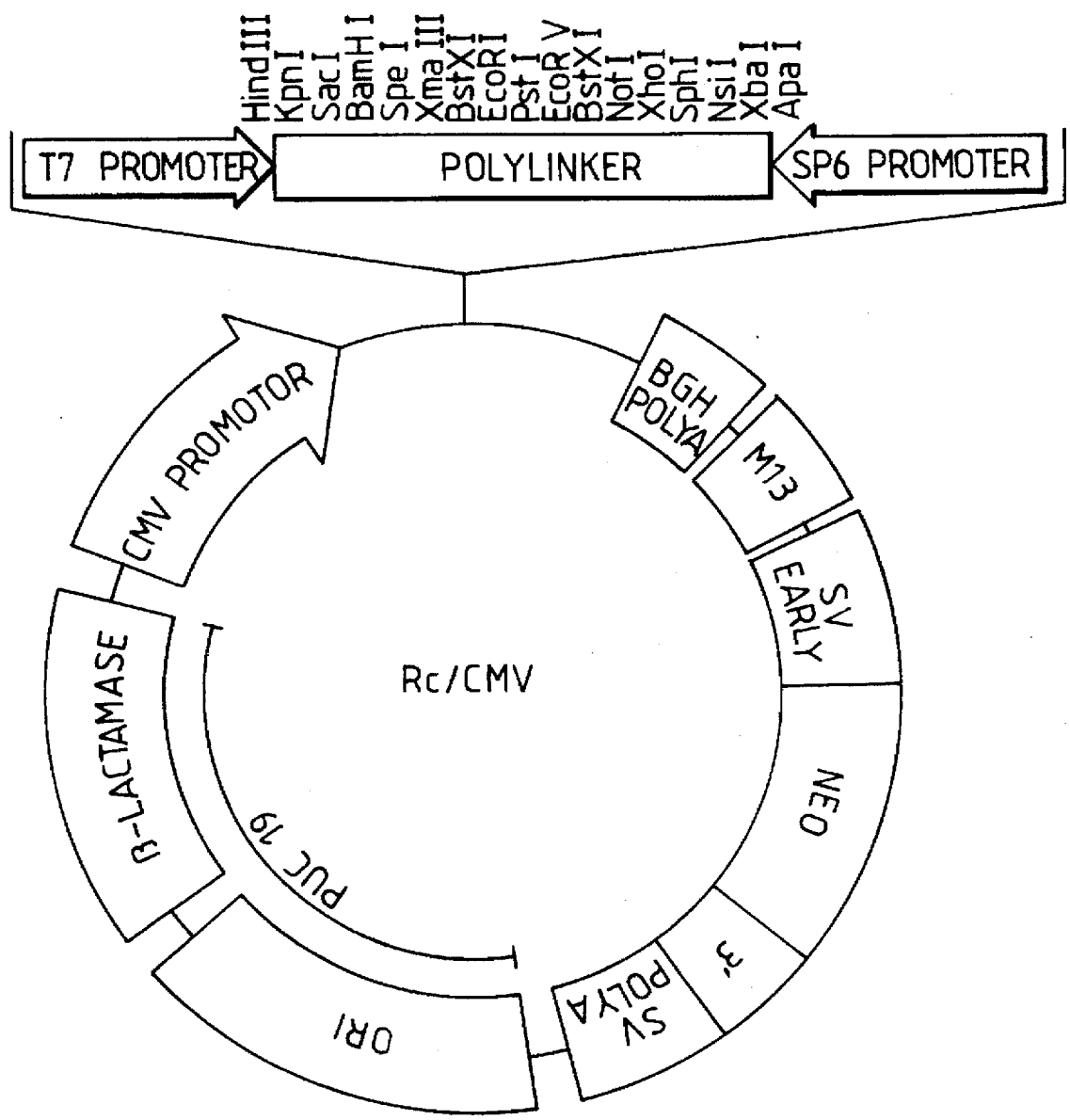
Figure 11:
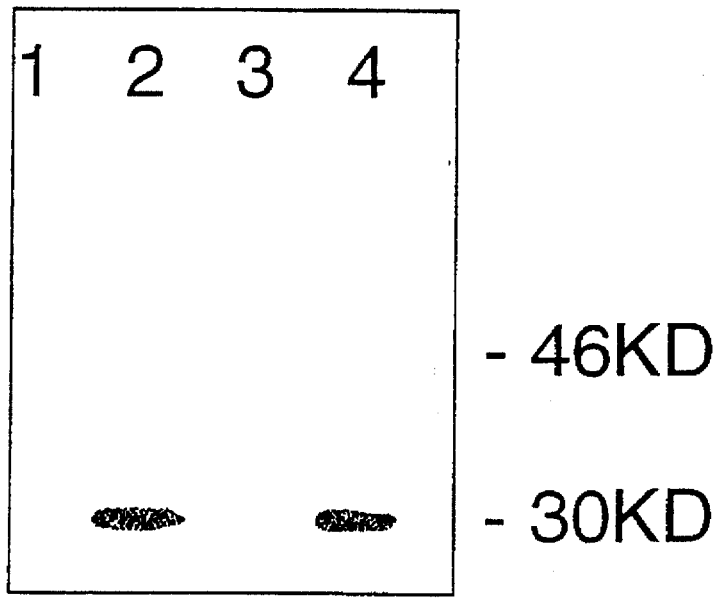
Figure 13:
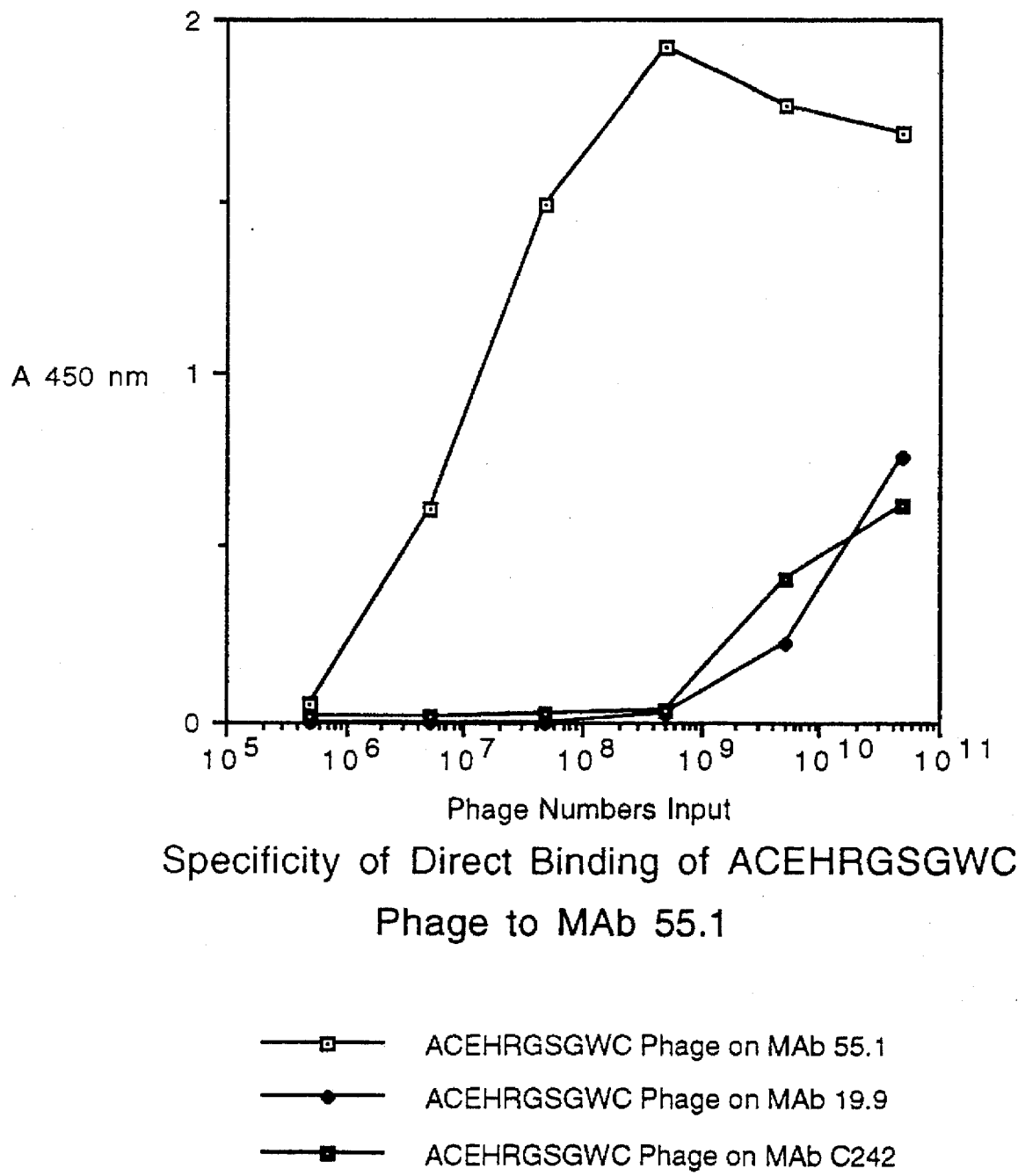
Figure 14:
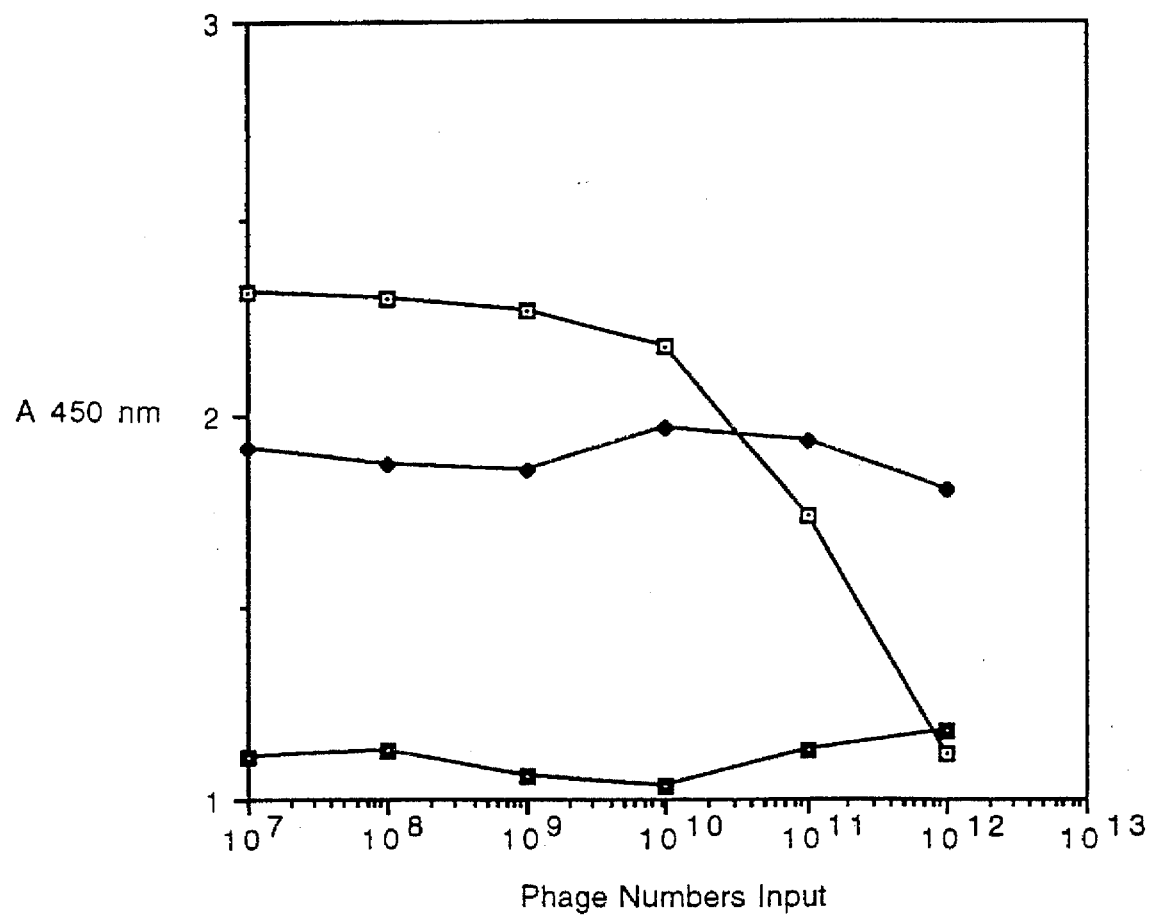

FIGS. 7A & B show representations of Western blots with lectins DSA and GNA;

FIG. 8 shows a map of plasmid pRc/CMV;

FIG. 9 shows a Western blot demonstrating Fab' and F(ab')$_2$ expression;

FIG. 10 shows ELISA data on Fab' and F(ab')$_2$ binding;

FIG. 11 shows a Western blot demonstrating scFv expression;

FIG. 12 shows ELISA data on scFv binding;

FIG. 13 shows specificity of direct binding of ACE-HRGSGWC phage to 55.1 antibody FIG. 14 shows specificity of binding of ACEHRGSGWC phage in a competition assay FIGS. 15 & 16 show the heavy and light chain cDNA sequences of antibody 55.1. Note the presence of secretory leader peptide sequences which are present in the mature antibody chains. The leader sequences are shown in 3 letter amino acid code and the mature sequences in single letter code.

Figure 17:
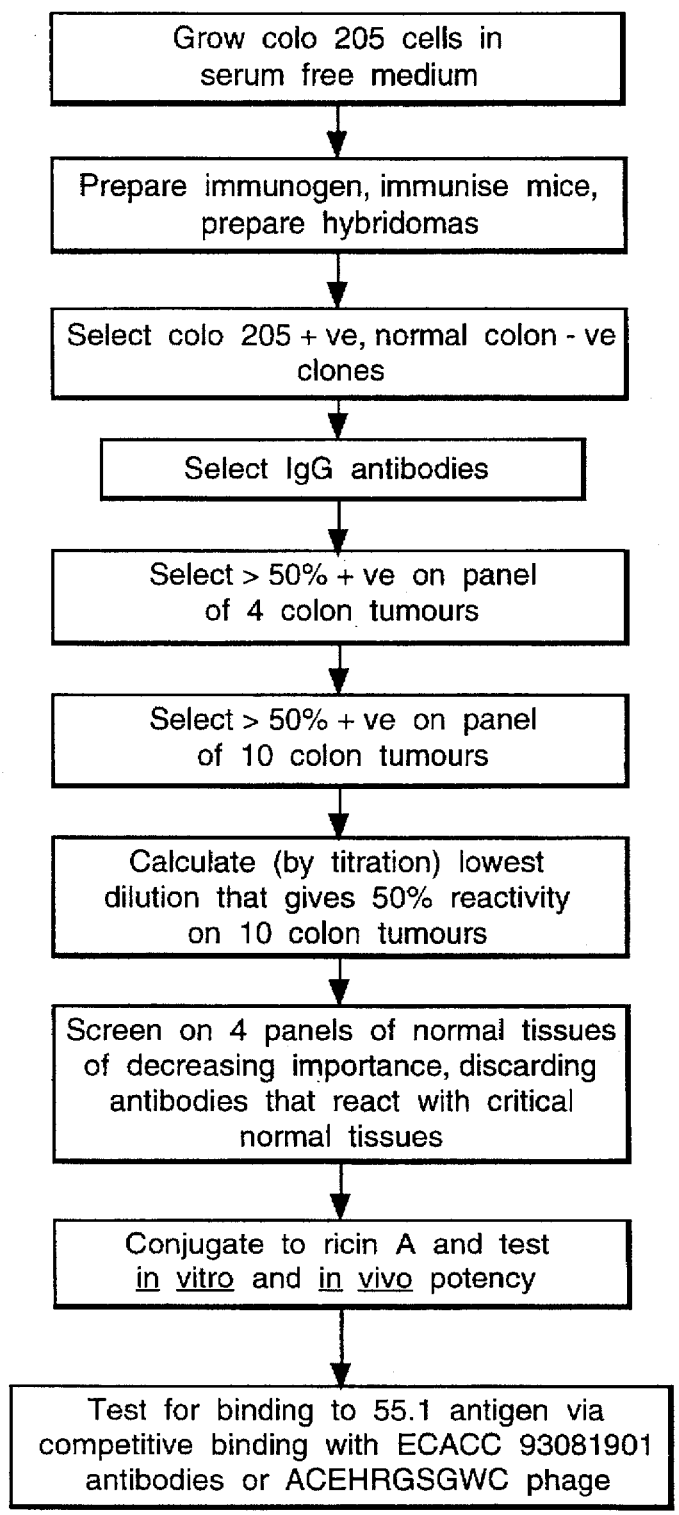

FIG. 17 shows a flowchart for generation of antibodies to 55.1 antigen.

FIG. 18 shows the double stranded DNA sequence of the c-myc tag used for antibody detection.

Table 1 shows cell density and IgG concentration on culture of 55.1 hybridoma in serum containing medium;

Table 2 shows cell density and IgG concentration on culture of 55.1 hybridoma in protein free medium;

Table 3 shows 55.1 antibody reactivity with colorectal tumours and;

Table 4 shows proportions of normal tissues staining with 55.1 antibody.

Abbreviations:

SDS-PAGE is sodium dodecyl sulphate (SDS) polyacrylamide gel electrophoresis (PAGE)

TABLE 1

GROWTH AND IgG PRODUCTION FROM 55.1 IN 5% FBS IS ROLLER CULTURE

| TIME | CELL DENSITY (Cell/ml × 10e5) | | IgG |
|---|---|---|---|
| (hours) | Viable | Total | (mg/l) |
| 0 | 2.58 | 3.05 | |
| 26.3 | 3.2 | 3.65 | 19.3 |
| 43.3 | 4.05 | 5.15 | |
| 69.5 | 6.5 | 8.05 | 39.1 |
| 95.8 | 12.9 | 16.25 | 67.6 |
| 144 | 9.3 | 18.7 | 101.3 |
| 167 | 4.65 | 18.3 | 111 |
| 188.8 | 3.75 | 22.5 | 126.5 |
| 215.8 | 1.25 | 21.9 | 121.5 |
| 236.5 | 0.8 | 23.5 | 122.5 |
| 260.9 | 0.4 | 20.6 | 123.5 |
| 308.8 | 0 | 20.6 | 126.5 |

TABLE 2

GROWTH AND IgG PRODUCTION FROM 55.1 IN PROTEIN FREE MEDIUM IN ROLLER CULTURE

| TIME | CELL DENSITY (Cell/ml × 10e5) | | IgG |
|---|---|---|---|
| (hours) | Viable | Total | (mg/l) |
| 0 | 2 | 2.12 | |
| 46.3 | 7.65 | 9.05 | 42.7 |
| 70 | 10.2 | 12.8 | 57.9 |
| 92 | 10.3 | 13.4 | 72.4 |
| 122.8 | 6.15 | 14.3 | 85.3 |
| 188 | 0.95 | 14.2 | 119 |
| 214.8 | 0.15 | 14.1 | 119.5 |
| 235.8 | 0 | 15.6 | 129 |

TABLE 3

55.1 Human Colo-Rectal Tumour Reactivity

| Tumour (patient initials) | Staining score |
|---|---|
| LM | +++ |
| AW | + |
| HM | +++ |
| JG | +++ |
| LG | + |
| KA | + |
| HO | ++ |
| JP | − |
| CD | +++ |
| EM | + |
| JP | +++ |
| ED | + |
| AB | ++ |
| FW | +/− |
| WC | +/− |
| DM | + |
| DG | +++ |
| TD | ++ |

TABLE 4

Proportion of Normal Tissues Staining with 55.1

| Immunohistology Score | % of Tissues Stained |
|---|---|
| − | 59 |
| +/− | 26 |
| + | 14 |
| ++ | 1 |

EXAMPLE 1

Preparation of 55.1 Antibody and Antibodies which Cross React with CA55.1

Since its inception in 1976 monoclonal antibody generation has been applied to the search for cancer cell selective antigens. Unlike the generation of antibodies to a fully purified antigen this process involves immunising mice with a less pure preparation, then applying a screening cascade so that antibodies of the required specificity are identified. Antibodies identified in this manner may then be used to identify the cancer-selective antigen through procedures well known to someone skilled in the art.

Having identified the antigen, further antibodies with similar specificity may be generated by immunising animals with an enriched preparation of said antigen (such as prepared by the method described in example 11), fusing the spleen cells of these animals with a suitable myeloma cell line as described below and screening the resulting hybridomas for the production of monoclonal antibodies which cross react with the monoclonal antibody 55.1 by the method described in EXAMPLES 6 AND 7.

1.1 Establishment of Hybridoma Cell Line and Production of 120/466.034.017.023.023.003; Preparation of Established Spleen Cells A human colorectal carcinoma cell line, COLO 205, commercially obtainable from the American Type Culture Collection (ATCC), Rockville, Md., USA, under accession No. CCL 222, was routinely cultured in serum-free medium. Cells were harvested when they reached an approximate densitity of 7×10e5, and then washed 3 times in Iscoves basal(protein-free) medium for immunization.

BALB/c mice, 8 to 10 weeks old, were immunized intraperitoneally with a priming dose of 100 µg of membranes derived from COLO 205 cells suspended in 0.1 ml of phosphate buffered saline solution and 0.1 ml of Freund's Complete Adjuvant. Two weeks later and again 4 weeks later the animals were boosted with other further doses 100 µg of COLO 205 membranes suspended in phosphate buffered saline and Freund's Incomplete adjuvant. Six weeks after the second booster immunisation, mice were given a final intraperitoneal immunisation of 100 µg Colo205 membranes suspended in phosphate buffered saline alone and sacrificed four days later and the spleens were removed. The spleens were then dissociated into a single cell suspension by injecting Dulbecco's modification of Eagle's medium into the spleen sack.

1.2 Preparation of Hybridoma $1.95 \times 10e^8$ spleen cells from the above described cell suspension were mixed with $2.136 \times 10e7$ myeloma cells from the mouse myeloma cell line NS0 (available from the European Collection of Animal Cell Cultures under the accession No. 85110503). The tube was centrifuged, and all liquid was decanted. To the tube was then slowly added (over 1 min with constant stirring) 1 ml of PEG solution at 37° C. (Boehringer PEG1500) with constant stirring and then stirred for a further minute. The fusion was interrupted by adding Dulbecco's Modification of Eagle's Medium according to the following scheme: 2 ml during the first 2 minutes, 8 ml during the following 4 minutes and another 10 ml over 2 minutes. The tube was then centrifuged and resuspended in 30 mls DMEM with 10% foetal calf serum. Aliquots of 50 µl were distributed to the wells of 6 96-well tissue culture dishes. After 24 hours, 50 µl per well DMEM with 10% foetal calf serum and double strength hypoxanthine/aminopterin/thymidine (HAT) supplements was added. Each well was fed with 200 µl DMEM with 10% foetal calf serum and single strength hypoxanthine/aminopterin/thymidine (HAT) supplements 7 days later.

1.3 Screening of Antibody Hybridomas

The spent medium from day 13 above was tested for COLO 205 positive/Normal colon negative antibodies. In brief, the wells of two sets of Nunc immunoplates maxisorp were coated with either $10e^5$ cells/well of COLO 205 cells; coating volume 100 µl or membranes derived from normal colon (10 µg/ml, 100 µl per well). The plates were centrifuged and 100 µl 0.2% glutaraldehyde in PBS added and incubated for 20' at room temperature. The plates were then washed with PBS tween and blocked with 0.1% porcine gelatin in PBS, 200 µl per well. The above mentioned spent culture medium from day 13 was then added to the coated wells of both sets of plates, 50 µl/well. After incubation for 2 hours at room temperature peroxidase conjugated anti-mouse IgG (Sigma, goat anti-mouse IgG whole molecule, absorbed with rat serum proteins, A8924)) diluted (1/2000) in 0.1% Tween 20-PBS was added at 100 µl/well and incubated 2 hours at room temperature. Substrate, in the form of 90 µg OPD dissolved in 100 ml of citrate/phosphate buffer, pH 4.5, plus 15 µl of 30% hydrogen peroxide, was then added at 100 µl/well and incubated at room temperature for 15 minutes. The reaction was then stopped with addition of 50 µl citric acid (0.5M) and the absorbance was measured at 450 nm.

When screening the products of hybridomas for their ability to bind to specific targets, it is advantageous to use a second-labelled antispecies antibody that firstly reflects the desirable characteristics required of a hybridoma product and secondly does not exclude (that is fail to react with) hybridoma products which may have these characteristics. Specifically, in the case of the discovery of 55.1 we sought to exclude IgM monoclonal antibodies from further study, because these molecules form part of the early humoral response and are generally of low affinity and poor specificity. To achieve this we screened a number of commercially available anti-mouse IgG peroxidase conjugates for their ability to react with murine IgM, and then discarded any preparations that showed this characteristic. We did not, however, wish to exclude any subclass of IgG monoclonal antibodies. Thus our next step was to determine the ability of the remaining commercial conjugates to react with murine IgG1, IgG2a, IgG2b & IgG3. We found no commercially available preparation that both failed to react with murine IgM, and reacted equally with all subclasses of murine IgG. To overcome this we enhanced the best anti-mouse IgG reagent by addition of specific anti-subclass conjugate(s). The final preparation equally well recognised the four recognised subclasses of murine IgG.

Roughly 600 hybridoma clones were tested. Initially, 165 of these reacted with COLO 250 cells. Of these, 43 were shown to react also with normal human colon membrane, and were discarded. A clone established from one of the remaining hybridomas was designated 120/466 and was isotyped as IgG1 class. The 120/466 hybridoma was then subjected to a number of subcloning steps to eventually produce a final, stable monoclonal antibody producing a clone designated as 120/466.034.017.023.023.003, which became known as 55.1.

Thus, the 120/466 hybridoma was first cloned resulting in a clone called 120/466.034. This clone was in turn cloned to form clone 120/466.034.017; this clone was in turn cloned to form clone 120/466.034.017.023; this clone was in turn cloned to form clone 120/466.034.017.023.023; this clone was in turn cloned to form clone 120/466.034.017.023.023.003. In all these clonings, hybridoma suspension was diluted in hypoxanthine/thymidine (HT) supplemented culture medium to a density of 2.5 cells/ml. 200 µl (1 cells) were distributed to each well in a 96-well culture dish. After 5–7 days, single cell clones were detected by visual inspection in a microscope. On day 17, medium was changed and aliquots of spent media analysed for quantity of antibodies binding to COLO 205 cells but not to normal membranes by ELISA as described above. The best clones in terms of positive reaction in the COLO 205 ELISA which retained negative reaction in the normal cell ELISA were selected and frozen in vials in liquid nitrogen for further development.

Testing of the cloning of 120/466.034.017 indicated that 66% of the cells produced antibodies which reacted with colo 205 cells. Testing of the cloning of 120/466.034.017.023 indicated that 100% of the cells produced antibodies which reacted with colo 205 cells. Testing of the cloning of 120/466.034.017.023.023 indicated that 100% of the cells produced antibodies which reacted with colo 205 cells. Following cloning, the hybridomas which reacted with COLO 205 cells and which did not react with normal human colon membrane were then evaluated as follows to identify 55.1.

The antibodies secreted by the hybridomas (exhausted media from $10^7$ cells grown in 75 $cm^2$ flasks for approximately 7 day) were evaluated by immunohistology (as described in example 6) on tissue sections from 4 colon tumours obtained from 4 different patients with primary colorectal cancer. Antibodies which bound strongly (++ see example 6) to at least 2 of these tumours were evaluated by immunohistology for reactivity on a larger panel of colorectal tumour sections from 10 different patients. Antibodies which bound strongly (++) to at least 5 of these tumours were evaluated further.

At this stage the hybridoma supernatants were titrated against the panel of 10 colorectal tumours to determine the highest dilution of the supernatant that gave strong reactivity (++) to at least 50% of the tumours. This was designated the 'working concentration' and was used to screen a series of panels of normal tissues. To minimise normal tissue screening a four step normal tissue screening cascade was devised where more critical tissues were screened first. Hybridomas were discarded if the antibody they secreted did not meet the reactivity criteria at each step in the cascade. The steps of the cascade, the tissues and the selection criteria were:

| Step | Tissues | Criteria for progression |
| --- | --- | --- |
| 1 | Heart, Nerve | No reactivity to either |
| 2 | Brain, Kidney, Adrenal | < ++ reactivity to any |
| 3 | Lung, Liver, Pancreas, Muscle | < ++ reactivity to 2 of these |
| 4 | Colon, Spleen, Stomach, Lymph node, Bladder, Parathyroid, Skin, Ovary, Testis | < ++ reactivity to 4 of these |

This screening cascade led to the identification of antibody 55.1

EXAMPLE 2

Preparation of 55.1 Antibody from Deposited Cell Line ECACC No. 93081901

2.1 Preparation from Serum Containing Medium

A 1 ml cryopreserved amoule was removed from storage in liquid nitrogen and rapidly thawed in a 37 deg. C. water bath. The contents were aseptically transferred to a sterile 15 ml centrifuge tube. The cells were resuspended by dropwise addition of 10 ml of Dulbecco's modified Eagle's medium (DMEM) containing 10% (v/v) foetal calf serum (FCS) accompanied by gentle mixing. The suspension was centrifuged at 50×g for 10 min and the supernatant aseptically removed and the pellet resuspended in 10 ml of DMEM and 10% FCS in a 95% air/5% carbon dioxide pre-gassed 25 ml tissue culture flask. The flask was incubated at 37° C.

After 3 days the flask was sub-cultured by passing the contents of the entire flask into a larger 75 ml flask and diluting with DMEM+10% FCS (final viable density=2.5× 10E5 cells/ml). Further expansion to 162 ml flasks was performed in a similar manner except that the FCS concentration was reduced to 5%.

Figure 1:
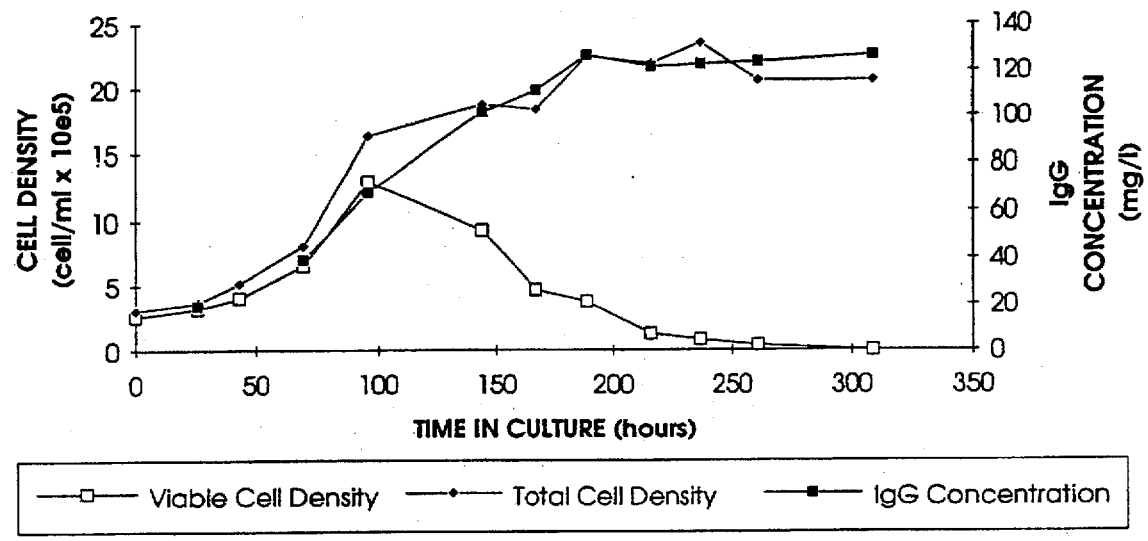
FIG. 1 shows cell density and IgG concentration on culture of 55.1 hybridoma in serum containing medium.

Culture supernatants for purification were prepared in 250 ml and 500 ml roller cultures in 490 ml and 850 ml roller bottles respectively. Cultures were seeded at 2.6×10E5 viable cells/ml in pre-gassed roller bottles, rotated at 3 rpm and incubated at 37° C. Cultures were grown to maturity and harvested 309 hours after inoculation when the cell viability was 0% and IgG concentration had reached a maximum (Table 1 and FIG. 1).

2.2 Preparation from Protein Free Medium

Roller cultures in 5% FBS were adapted to protein free growth and productivity by serial passage in Gibco Protein Free Hybridoma Medium II (PFHMII, catalogue number 074-03600P) supplemented with FBS. FBS concentration was reduced in 50% steps once healthy growth was established after each successive reduction. Cultures were seeded at 3×10E5 viable cell/ml and not allowed to grow higher than 1×10E6 viable cell/ml during the adaptation process. Once weaned to protein free growth, culture supernatants for purification were prepared in 250 ml and 500 ml roller cultures as before. Cultures were seeded at 2.0×10E5 viable cell/ml in pre-gassed roller bottles, rotated at 3 prm and incubated at 37° C. Cultures were grown to maturity and harvested 236 hours after inoculation when cell viability was 0%, and immunoglobulin G (IgG) concentration maximum (see Table 2 and FIG. 2).

2.3 Treatment of Culture Harvests

After harvest, roller culture supernatants were clarified by centrifugation at 60 g for 30 minutes. Clarified supernatants were stored sterile at 4° C. in the dark until purification.

2.4 Purification of 55.1

55.1 antibody has been isolated from cell culture supernates by adsorption onto and elution from Protein A.

5 liters 55.1 antibody cell culture supernate, grown in a serum-free nutrient medium, containing approx. 80 mg Ab/liter, was made 1.5M glycine/3M sodium chloride by addition, with stirring, of 562.5 g glycine+876.6 g sodium chloride. The pH of the solution was adjusted to 8.9 with 5M sodium hydroxide. The resulting solution was filtered by pumping through a prefilter (Millipore 'Polygard' cartridge filter) followed by a 0.45μ filter (Millipore Millidisk PVDF cartridge filter).

A 500 mg nominal IgG capacity Nygene Protein A cartridge of 500 ml bed volume was washed with 4 bed volumes of 0.45μ prefiltered 1.5M glycine/3M sodium chloride pH 8.9 buffer at flow-rate of 500 ml/minute using a peristaltic pump.

All buffers subsequently used with the Nygene cartridge were prefiltered through a 0.45μ filter.

The filtered 55.1 culture supernatant, at pH 8.9, was pumped through the cartridge, also at 500 ml/min. and the column was washed with the 5 bed volumes of the glycine/salt buffer until all of the methyl red medium indicator was removed from the cartridge. The cartridge was then washed with 1 bed volume of PBS at the same flow-rate, followed by elution of the 55.1 antibody with 3 bed volumes of 100 mM sodium citrate pH 2.8 at a flow-rate of 250 ml/min., collecting 50 ml fractions and monitoring the presence of the Ab by UV A280 nm. All of the antibody containing fractions were bulked and neutralised with 1M sodium hydroxide.

The glycine/salt column effluent and washes were recycled through the Protein A cartridge to yield ~15% more antibody in the subsequent citrate wash.

All of the bulked antibody was buffer exchanged into PBS buffer. SDS-PAGE of the bulked antibody showed >90% purity, with a yield of 360 mg antibody.

EXAMPLE 3

Production of Antibody Binding Structures by the Use of Recombinant DNA Technology 3.1 Determination of 55.1 Heavy and Light Chain cDNA Sequences The following example describes the construction of a cDNA library from the 55.1 hybridoma, the isolation of specific cDNA clones encoding heavy and light chain proteins and determination of the complete DNA sequence of these clones.

3.1 (a) Preparation of mRNA from Hybridoma Cells

There are several procedures for the isolation of polyA+ mRNA from eukaryotic cells (Sambrook J., Fritsch E. F., Maniatis T., Molecular Cloning: A Laboratory Manual, Cold Spring Harbor Laboratory Press, Second Edition, 1989, Chapter 8 p3 hereinafter referred to as Maniatis). One such method is provided in kit form by Pharmacia and relies on the lysis of a relatively small number of cells ($10^7$ or less)

followed by binding of polyA+ mRNA to an oligo dT column. Unwanted cell components are removed by washing with a low salt concentration before eluting the mRNA in high salt solution at elevated temperature.

mRNA was prepared from $10^7$ 55.1 hybridoma cells using the Quickprep mRNA kit (Pharmacia Biotechnology Ltd.). The concentration of the mRNA was estimated by scanning a sample from 300–220 nm in a Uvikon 930 spectrophotometer (Kontron Instruments) and using an extinction coefficient of 40 µg/ml at 260 nm. The mRNA was stored as 2.5 µg aliqouts precipitated in ethanol.

3.1 (b) cDNA Synthesis and Cloning

The method used for cDNA synthesis was based on that of Gubler and Hofman which relies on reverse transcription from primed mRNA followed by RNAse H treatment to provide priming and synthesis of the second strand by DNA polymerase I. Other methods for the synthesis of cDNA are reviewed in Maniatis (Chapter 8).

A 5 µg sample of mRNA was primed with oligo dT (12–18 mer mixture, Pharmacia Biotechnology Ltd., 0.5 µg) in a 10 µl solution containing 2.5 u placental RNAse inhibitor (Life Technologies Ltd.) made up with RNAse-free water by incubating at 70° C. followed by cooling on ice. First strand cDNA synthesis was then performed by adding 4 µl 5× H-RT buffer (250 mM Tris, pH 8.3, 200 mM KCl, 30 mM $MgCl_2$ and 0.5 mg/ml BSA), 2 µl 10.1M DTT (dithiothreitol), 1 µl dNTP mix (dATP,dCTP,dGTP and dTTP at 20 mM), 4 µl Superscript Reverse transcriptase (Life Technologies Ltd.) and incubating at 42° C. for 1 hour. For the second strand reaction, 1.5 µl dNTP mix (as above), 92.5 µl RNAse-free water, 30 µl 5× reaction buffer (125 mM Tris, pH 7.5, 500 mM KCl, 25 mM MgCl2 50 mM $(NH_4)_2SO_4$ and 0.5 mg/ml β-NAD), 1 µl T4 DNA ligase (10u, Life Technologies Ltd.), 4 µl DNA polymerase I (40u, Life Technologies Ltd.) and 1 µl RNAse H (2.7u, Life Technologies Ltd.) were added and incubation continued at 16° C. for a further 2 hours. To ensure that blunt-ended cDNA was prepared a final incubation at 16° C. for 5 minutes after adding 2 µl T4 DNA polymerase (10u, Life Technologies Ltd.) was performed. Enzyme activity was then stopped by incubation at 70° C. for 10 minutes.

To prepare the cDNA for cloning the above solution was extracted against an equal volume of phenol and the resulting aqueous phase extracted with an equal volume of phenol:chloroform (50:50 v:v) to remove proteins before purifying by spun column chromatography using Sepharose C4-LB in a column purchased from Pharmacia Bioctechnology Ltd. and used in accordance with the manufacturers instructions. The purified cDNA was then mixed with 5 µl EcoRI/NotI adaptors (Pharmacia Biotechnology Ltd.), 1 µl ATP solution (5 mM) and 3 µl T4 DNA ligase (10u, Pharmacia Biotechnology Limited) and incubated at 12° C. overnight. The cDNA plus adaptors was then phosphorylated by addition of 10 µl ATP solution (5 mM) and 1 µl T4 polynucleotide kinase (10u, Pharmacia Biotechnology Limited) and incubation at 37° C. for 30 minutes. Again, the solution was extracted against equal volumes of phenol and phenol:chloroform and purified by spun column chromatography to remove excess adaptors. At this stage the cDNA is ready for cloning into an appropriate plasmid or phage vector.

pBluescript (Stratagene Cloning Systems) was used for construction of a cDNA library. This phagemid vector has a unique EcoRI cloning site, Ampicillin resistance gene, and both ColEI and fI replication origins for isolation of either double- or single stranded DNA. 5 µg pBluescript KS- DNA was digested to completion with 30 u EcoRI (Promega Corporation) in a solution containing 90 mM Tris-HCl, pH 7.5, 10 mM MgCl2, 50 mM NaCl at 37° C. for 45 minutes. 2 µl calf-intestinal alkaline phosphatase (2u, Boehringer Mannheim) was then added to remove 5' phosphate groups and incubation continued at 37° C. for a further 30 minutes. Phosphatase activity was destroyed by incubation at 70° C. for 10 minutes.

5 µl of the cDNA plus adaptors was ligated with 25 ng of EcoRI/CIP treated pBluescript in a solution containing 30 mM Tris-HCl, pH 7.8, 10 mM MgCl2, 10 mM DTT, 1 mM ATP and 1.5 u T4 DNA ligase (Promega Corporation) at 16° C. for 2.5 hours. 5 µl and 2.5 µl aliquots of this reaction were used to transform 100 µl and 50 µl of competent *E. coli* DH5α cells (Life Technologies Ltd.) respectively using the protocol provided with the cells. Transformed cells were plated onto L-agar plus 100µg/ml Ampicillin, 1 mM IPTG and 0.2% X-gal and incubated overnight at 37° C. Clones containing cDNA inserts were selected on the basis of producing white colonies on the above medium compared to the blue colour generated by cells containing the parental plasmid. Two hundred white colonies in batches of 50 were picked in duplicate onto nitrocellulose discs (Schleicher and Schull) laid onto L-agar plus ampicillin plates. A third set of plates without filters was streaked to form a master stock of the selected colonies. After overnight incubation at 37° C., the nitrocellulose filters were removed and processed according to the method of Grunstein and Hogness (Maniatis, Chapter 1, p102) to lyse the bacterial cells in situ. The filters were overlaid on 3 MM paper (Whatman) soaked in the various reagents—10% SDS for 2 minutes, 3M NaOH, 1M NaCl for 5 minutes and 1M Tris, pH6.8 for 2×2 minutes. The filters containing lysed cells were transfered to 3 MM paper moistened with 20× SSC (3M NaCl, 0.3M sodium citrate) and the DNA cross-linked to the filters by exposure to UV light in a Stratalinker 2400 (Stratagene Ltd.) set on auto-crosslink (120,000 µJoules). The filters were air dried before use in probing (see below). The master stock plates were stored at 4° C. until required.

3.1 (c) cDNA Library Screening

To generate effective probes for cDNA library screening the variable region DNAs of the 55.1 heavy and light chains were isolated by the polymerase chain reaction (PCR, Saiki, R. et al, 1985, Science, vol 230 p1350–1354). This was possible due to the availability of N-terminal protein sequence data for both chains (see above). This data was used to design 5' PCR primers (SEQ ID NO: 1–4). Two primers were synthesised for each sequence, one based on the most commonly occuring codons for mouse V-regions determined from published sequences (Sequences of Proteins of Immunological Interest, 4th edition, 1987, Kabat, E. A., Wu, T. T., Reid-Miller, M., Perry, H. M. and Gottesman, K. S., published by The U.S. Department of Health and Human Services and hereinafter refered to as Kabat) (SEQ ID NO: 1 and 3) and another including degeneracy at some base positions to cover several codon options (SEQ ID NO: 2 and 4). PCR primers for the 3' end (SEQ ID NO: 5 and 6) were complementary to sequences published in Kabat for the 5' regions of CH1 of IgG1 and the 3' terminus of Cκ respectively. The heavy chain isotype had been determined by assay (see above) and the N-terminal VL protein sequence indicated that the light chain was the kappa isotype. These 3' constant region primers could also be used as screening probes in their own right.

3.1 (d) Oligo Synthesis

All oligonucleotide sequences used were prepared on Applied Biosystems 380B or 394 DNA synthesisers from 5'dimethoxytrityl base-protected nucleoside-2-cyanoethyl- N,N-di-isopropyl-phosphoramidites and protected nucleosides linked to controlled-pore glass supports on a 0.2 μmol scale, according to protocols supplied by Applied Biosystems Inc.

Alternatively, the oligonucleotides can be prepared manually by the methods described by Atkinson and Smith in "Oligonucleotide Synthesis, a manual approach" (M. T. Gait, editor, IRL Press, Oxford, Washington D.C., pages 35–81).

Each synthesised oligonucleotide, after cleavage from the solid support and removal of all the protecting groups, was dissolved in double distilled water (1 ml).

3.1 (e) Probe Generation

Variable region DNA fragments were generated from cDNA using PCR. 1 μl of cDNA was added to a 100 μl reaction containing 10 mM Tris-HCl, pH 8.3, 50 mM KCl, 0.1% gelatin, 1.5 mM MgCl2, 1.25 mM each of dATP, dCTP, dGTP and dTTP, 1 μM each of an appropriate oligo pair and 2.5 u Taq DNA polymerase (Amplitaq, Perkin-Elmer Cetus). Each reaction was overlaid with 100 μl mineral oil and incubated at 94° C. for 1.5 minutes, 50° C. for 1.0 minute and 72° C. for 2.0 minutes for 25 cycles plus 10 minutes at 72° C. Control reactions with no DNA were also set up.

The PCR reactions were analysed by running a 5 μl sample of each on a 0.8% agarose (Pharmacia Biotechnology) gel which was subsequently stained in 1 μg/ml Ethidium Bromide (Sigma Chemical Company Ltd.) solution and the DNA visualised on a UV transilluminator. The presence of a band of approximately 400 bp was visible in all PCRs with 55.1 cDNA present indicating successful amplification of the variable regions. The absence of a DNA band in the control reactions indicated that the reagents used did not contain contaminating DNA.

Each PCR product was purified by use of a Centricon 100 microconcentrator (Amicon Ltd.). Each reaction was added to a concentrator and the volume increased to 2 ml by addition of double distilled water. The unit was then centrifuged at 2000 rpm for 5 minutes and the "flow-through" discarded. The retentate was diluted to 2 ml again and the unit re-centrifuged. The process was repeated for a third time. This procedure results in the removal of excess oligos and buffer components from the amplified DNA.

The amplified VH and VL fragments were used to generate specific hybridisation probe for heavy and light chain cDNA clones. Radio-labelled probes were generated using a T7 QuickPrime kit (Pharmacia Biotechnology Ltd.) as follows: 5 μl (~50 ng) of the purified PCR product was added to 32 μl of double distilled water and the whole incubated at 100° C. for 2 minutes to denature the double-stranded DNA. This sample was then cooled on ice before adding 10 μl reagent mix (a buffered aqueous solution containing dATP, dGTP, dTTP and random oligo primers, primarily 9-mers), 2 μl α32P dCTP (20 μCi 3000 Ci/mmol, NEN), and 1 μl T7 polymerase (4–8 u). The reaction was incubated at 37° C. for 20 minutes before adding to 10 ml of 6×SSC (1M NaCl, 0.1M sodium citrate), 0.1% SDS (sodium dodecyl sulphate) and 0.25% Marvel™ (fat-reduced dried milk powder) which was then used as a probe solution.

3.1 (f) Library Probing

The processed filters containing the selected clones (see above) were pre-hybridised in duplicate batches each in 90 ml 6×SSC, 0.1% SDS, 0.25% Marvel™ at 65° C. for 3 hours in a Techne HB-1 hybridisation oven using rotating glass tubes. Each duplicate set was then probed in 10 ml of probe solution (one set with the VH probe and the other with VL) at 65° C. overnight in the same apparatus. After incubation, each set of filters was washed in 100 ml 6×SSC, 0.1% SDS at 65° C. for 15 minutes, 100 ml 3×SSC, 0.1% SDS at 65° C. for 30 minutes and 100 ml 1×SSC, 0.1% SDS at 65° C. for 30 minutes in the same apparatus. The washed filters were then air dried and autordiographed using Hyperfilm™ MP (Amersham International) in conjunction with a fast tungstate intensifying screen at −70° C. After developing the film in a Kodak automatic film processor, 2 potential heavy chain cDNA clones and 1 potential light chain cDNA clone were clearly identified by hybridisation of the relevant probe. The frequecy of the antibody cDNA clones identified is typical of hybridoma cDNA libraries (Levy, S. et al, 1987, Gene, vol 54, p167–173).

3.1 (g) DNA Sequence Analysis of cDNA Clones

The potential heavy and light chain cDNA clones identified by hybridisation were picked from the master plate and used for large scale plasmid DNA preparation. Each clone was used to inoculate 200 ml of L-broth plus ampicillin in a 500 ml conical flask. The cultures were incubated, shaking at 37° C. overnight. After growth the cells from each culture were pelleted by centrifugation at 5000×g for 10 minutes in a Sorvall RC5C centrifuge and GS3 rotor at 4° C. The cell pellet from each culture was resuspended in 20 ml TE buffer and re-centrifuged at 2000×g for 10 minutes in a Sorvall RC5C centrifuge and SS-34 rotor in an oak-ridge tube at 4° C. Each washed cell pellet was resuspended in 3 ml ice cold 25% sucrose, 50 mM Tris, pH 8.0, and left on ice. Fresh lysozyme solution (1.0 ml at 10 mg/ml) was added, the contents mixed by rolling the tube and incubation on continued for 5 minutes. Sodium ethylenediaminetetraacetic acid (EDTA) solution (1.0 ml at 0.5 mM, pH 8.5) was added and the contents gently mixed. Finally, 5.0 ml of iced Triton X solution (0.1% Triton X-100, 62.5 mM EDTA, 50 mM Tris, pH 8.0) was added, the contents gently mixed and incubation on ice continued for a further 10 minutes. The cell debris was then pelleted by centrifugation at 39,000×g for 30 minutes in a Sorvall RC5C centrifuge and SS-34 rotor at 4° C. The supernatant containing plasmid DNA was added to 16 g Caesium chloride and 150 μl ethidium bromide solution (10 mg/ml) and the volume increased to 18.5 ml by addition of TE buffer. This solution was transferred to an 18.5 ml crimp top, polypropylene centrifuge tube (Sorvall Instruments). The tube was sealed and centrifuged at 180,000×g for 16 hours in a Sorvall TV865B (titanium, vertical) rotor and OTD65B centrifuge at 18° C.

After centrifugation, plasmid DNA was visible as a distinct orange band in the CsCl/EtBR density gradient which had formed. The plasmid DNA was removed from the gradient using a hypodermic syringe to pierce the tube wall. The sample taken from the gradient was diluted 3–4 fold with TE buffer and the DNA precipitated by addition of an equal volume of isopropyl alcohol and incubation on ice for 10 minutes. The precipitated DNA was pelleted by centrifugation at 17,000×g in a Sorvall RC5C centrifuge and SS-34 rotor at 4° C. and the supernatant discarded. The resulting pellet was washed in 70% ethanol (v/v) and re-centrifuged for 5 minutes. The pellet was then dried under vacuum, resuspended in 1.8 ml TE buffer and 200 μl 3M sodium acetate solution and extracted with an equal volume of phenol using centrifugation at 17,000×g for 2 minutes to separate the phases. The aqueous phase was re-extracted against an equal volume of chloroform before precipitating the DNA by addition of an equal volume of ethanol at −20° C. and incubating on ice for 10 minutes. The purified DNA was pelleted as above, washed in 70% ethanol and the pellet vacuum dried. The dried pellet was resuspended in 500 μl double-distilled water and DNA concentration estimated by scanning a diluted sample from 300 to 220 nm in a UV spectrophotometer using and extinction coefficient of 50 µg/ml/OD 260 nm.

This purified plasmid DNA was the used for DNA sequence analysis. Double stranded DNA can be used for DNA sequence analysis by the dideoxy chain termination method of Sanger (Proc. Nat. Acad. Sci. USA 74, 1977, p5463) using a proprietary sequencing kit such as the Sequenase kit supplied by United States Biochemical Company and used in accordance with the protocols provided.

Aliquots (2–4 µg) of heavy and light chain cDNA clone plasmid DNA were used for DNA sequence analysis. Each aliquot was initially denatured by incubation with 0.2M NaOH, 0.2 mM EDTA in a final volume of 100 µl at room temperature for 10 minutes. The denatured DNA was then precipitated by addition of 10 µl 3M sodium acetate (pH 5.0) and 275 µl ethanol and incubation on ice for 10 minutes. The precipitated DNA was recovered as described for plasmid DNA above. The denatured DNA was then primed for sequencing by incubation of each with 0.5 pmoles of an appropriate primer in the presence of Sequenase reaction buffer (40 mM Tris, pH 7.5, 25 mM MgCl2, 50 mM NaCl) and 10% di-methyl sulphoxide (DMSO) at 65° C. for 2 minutes followed by gradual cooling to below 30° C. These primed templates were then used in sequencing reactions according to the protocols provided with 10% DMSO added to labelling and termination mixtures.

The sequencing reactions were analysed by autoradiography after high resolution polyacrylamide gel electrophoresis (Sanger and Coulson, 1978, FEBS Lett. 87, p107).

The complete heavy and light chain sequences of the cloned cDNAs are given below (SEQ ID NO: 23 for H chain cDNA, SEQ ID NO: 36 for amino acid with alignment between them in FIG. 15 and likewise SEQ ID NO: 24 shows L chain cDNA, SEQ ID NO: 37 shows the amino acid sequence and FIG. 16 shows alignment between them). The authenticity of these coding sequences was confirmed by comparison with N-terminal protein sequence deduced from purified antibody protein. The DNA sequence also confirms that the antibody is an IgGκ isotype.

3.2 Expression of Whole 55.1 Antibody in Myeloma Cells

The following example describes the expression of 55.1 antibody from myeloma cells using sequences cloned into pRc/CMV (FIG. 8).

pRc/CMV (FIG. 8) uses the enhancer/promoter sequences from the immediate early gene of human cytomegalovirus (CMV) for high level transcription, a neomycin resistance gene for the selection of Geneticin sulphate (G418) resistant stable cell lines, unique restriction enzyme sites (HindIII, BstXI, NotI, XbaI and ApaI) downstream from the promoter sequence and polyadenylation signal/transcription termination sequences from bovine growth hormone 3' to the cloning sites.

3.2 (a) Subcloning into pRc/CMV

The 55.1 cDNAs are excisable, intact, from the pBluescript vector on a NotI fragment. Each fragment can subsequently be cloned into the NotI site of pRc/CMV independently to allow expression from the CMV promoter.

Aliquots of the various DNAs, pRc/CMV (3 µg) p55.1H (5 µg) and p55.1L (10 µg), are digested separately in a solution containing NotI (5 u/µg), 10 mM Tris-acetate (pH 7.5), 10 mM magnesium acetate, 50 mM potassium acetate and 0.1% Triton X-100 which is incubated at 37° C. for a minimum of 1 hour. In addition the pRc/CMV NotI digest is subsequently treated with calf intestinal alkaline phosphatase (2u, Pharmacia Biotechnology Ltd.) in the same solution at 37° C. for 40 minutes and inactivation of the enzyme at 80° C. for 15 minutes. This is to prevent recircularisation of the vector upon ligation. Complete digestion is analysed by agarose gel electrophoresis and the appropriate DNA fragments (pRc/CMV vector band, 5.5 Kbp, and 55.1 H and L inserts, 1.5 Kbp and 800 bp respectively) excised from the gel and purified as above.

Each 55.1 cDNA fragment is ligated, as described above, with the pRc/CMV vector fragment in separate reactions. The ligated DNA is used to transform competent DH5α cells and ampicillin resistant clones picked for plasmid DNA preparation and restriction enzyme analysis with NotI to identify pRc/CMV clones with the 55.1 H and L chain inserts. PCR is then used to subsequently identify clones with the correct orientation of insert for expression from those with the appropriate NotI insert. One colony from each putative clone is resuspended in 1 ml of double distilled water. The cells are then pelleted by microfuging at 6000 rpm for 1 minute, 800 µl of the supernatant is discarded and the cell pellet resuspended in the remaining 200 µl. The cells are then disrupted by incubation at 100° C. for 1 minute and the insoluble material pelleted at 12000 rpm in a microfuge for 2 minutes. One µl of the cleared supernatant is then used in a 20 µl PCR reaction containing a T7 promoter primer (SEQ ID NO: 7) and either an internal H chain primer (SEQ ID NO: 8) for H chain clones or an internal L chain primer (SEQ ID NO: 6) for L chain clones, 200 µM dNTPs, 10 mM Tris-HCl (pH 8.3), 50 mM KCl, 1.5 mM MgCl2, 0.01% gelatin and 0.5 u Taq polymerase (Amplitaq) and overlaid with 20 µl light mineral oil (Sigma Chemical Company Ltd.). Control reactions with no DNA are set up to detect contamination of reagent solutions. All reactions are incubated at 94° C. for 1.5 minutes, 50° C. for 1.0 minutes, 72° C. for 2 minutes for 20 cycles plus 10 minutes at 72° C. in a programmable heat controller (Techne PHC-1). The PCR products are analysed by running the entire reaction on a 0.8% agarose gel. Clones with the correct fragment orientation for expression are identified by the presence of a PCR product (~900 bp for H chain and ~600 bp for L chain) when compared to control reactions. Clones with the incorrect fragment orientation do not produce a PCR product due to both oligonucleotides priming the same DNA strand. One H chain clone with the correct orientation is named pRc/55.1H and a correct L chain clone pRc/55.1L.

Large scale plasmid preparations as described above are performed using these clones to provide sufficient DNA for transfection of myeloma cells. Prior to transfection a sample (50 µg) of each plasmid DNA (pRc55.1H, pRc55.1L and pRc/CMV) is digested to completion with BglII in a solution containing 25 u BglII, 6 mM Tris-HCl, pH 7.9, 6 mM MgCl2, 100 mM NaCl and 1 mM DTT at 37° C. for a minimum of 1 hr. BglII causes linearisation of the plasmid DNA at a point outside the antibody sequences and important control elements and should facilitate integration of the expression cassette into the host genome.

3.2 (b) Transfection of Myeloma Cells

Several methods exist for the introduction of DNA into eukaryotic cells (Bebbington, C., 1991, Methods, vol 2, p136–145). Electroporation has become a routinely used method more recently, replacing the calcium phosphate-DNA coprecipitation. However, the latter method has the benefit of producing a higher frequecy of integration of the plasmid DNA into chromosomal DNA and is favoured here where co-integration of 2 plasmids each carrying the same resistance marker is required. It is expected that a proportion of G418 resistant colonies produced after co-transfection of H and L chain bearing plasmids will express functional antibody molecules. NSO myeloma cells (Methods in Enzymology, 1981, 73B, p3. ECACC cat no. 85110503) are a suitable host cell for this work due to the absence of any endogenous secreted antibody protein.

The procedure used is based on that of Gorman (1986, DNA Cloning, vol. 2, p143, Academic Press, New York). Exponentiallly growing NS0 cells in non-selective medium (Dulbecco's Modified Eagle Medium; Life Technologies Ltd., plus 10% foetal calf serum from an acredited source) are seeded into 9 cm petri dishes at a density of $5 \times 10^5$ per dish in 10 ml non-selective growth medium and incubated at 37° C. for 24 hr. Immediately prior to transfection the plasmid DNA is co-precipitated with calcium phosphate. Linearised plasmid DNA (pRc55.1H and pRc55.1L) is mixed in equal proportions (2.5, 5 or 10 μg of each) in 0.5 ml of aqueous solution containing 62 mM CaCl2. Each mixture is then added dropwise to 0.5 ml of 2×HBS solution (280 mM NaCl, 2.8 mM Na2HPO4, 46 mM Hepes, pH 7.1) with continuous agitation. Air is then bubbled through the mixture to help formation of the calcium phosphate-DNA precipitate.

The growth medium is removed from the NS0 cells which are then washed with 10 ml of serum-free medium which is also discarded. The calcium phosphate-DNA precipitate is added to a petri dish of cells together with 1 ml of serum-free medium. Several different proportions of the 2 expression plasmids are used and 2 different quantities (5 and 10 μg) of pRc/CMV as controls. A control with no DNA is also set up. The cells are incubated in the presence of the precipitate for 4 hrs at 37° C. with occasional rocking to prevent areas of the plate from drying out. The precipitate is then removed from the cells and replaced with 3 ml of 15% glycerol in 1×HBS for 1.5 minutes at 37° C. before washing with 10 ml serum-free medium. The cells are then incubated in 10 ml non-selective medium at 37° C. for 24 hr.

Selective medium (DMEM plus 10% FCS and 1.5 mg/ml G418-Geneticin sulphate, Life Technologies Ltd.) is applied to the transfected cells after 24 hr and the cells maintained under this selection until the appearance of G418 resistant colonies. The colonies are then picked and sub-cultured under G418 selection for analysis of antibody expression by ELISA (see later).

3.3 Expression of Fragments of 55.1 in *E. coli*

The following examples describe the expression of chimaeric Fab' and F(ab')2 fragments (with human constant regions) and a single-chain Fv (scFV) of 55.1 from plasmid vectors in *E. coli*.

3.3 (a) Vector Systems

Plasmid expression vectors allowing the secretion of antibody fragments into the periplasm of *E. coli* have been described by several groups (Skerra, A. et al, 1991, Bio/ Technology vol 9, p273–278. Carter, P. et al, 1992, Bio/ Technology vol 10, p163–167. Better, M. et al, 1993, Proc. Natl. Acad. Sci. vol 90, p457–461). These generally consist of a regulable promoter (lac, araB, lpp etc) directing the co-expression of Fd' and L chain fragments each with its own secretion leader sequence (pelB, ompA etc) in a vector background (pAT153, pUC19 etc) which allows for selection and replication within a chosen *E. coli* host. We have constructed such a vector by introduction of an araB/C promoter/repressor element derived by PCR from *Salmonella typhimurium* into a pAT153 based vector with a Tc resistance gene, T4 transcription termination sequence and cer stability function (ref). Two pelB leader sequences and human CH1 and CK sequences were derived from pSW1FabD1.3 (Skerra, A. et al, 1991, Anal. Biochem. vol 196, p151–155). In addition, the pelB leader sequences were modified by site directed mutagenesis to introduce unique restriction sites. The pelB sequence upstream from the H chain fragment was modified to introduce a unique NcoI site, i.e.

5' ... TCGCTGCCCAACCAGCCATGGCC 3' where the underlined base represents a G to C substitution from the original sequence to create the NcoI site (CCATGG).

A vector with a single pelB leader sequence including the above mentioned NcoI site and the other vector features (pICI266) has been deposited under the Budapest Treaty at the National Collections of Industrial and Marine Bacteria Limited (NCIMB), 23 St. Machar Drive, Aberdeen, AB2 1RY, Scotland, U.K.

Similarly, a unique SfiI was introduced into the second pelB leader sequence upstream from the L chain, i.e.

5' ... TCGCGGCCCAACCGGCCCAGGCC 3' where the underlined bases represent base substitutions which introduce the SfiI site (GGCCCAACCGGCC) and prevent the creation of a second NcoI site. This latter change necessitates an amino acid substitution (Met to Gln) which is not expected to affect secretion as the C-terminal portion (Ala-Gln-Ala) is now identical to that of the ompA leader.

These modifications allow insertion of antibody V regions upstream from and in frame with the appropriate C regions on an NcoI-BstEII fragment for VH and an SfiI-XhoI fragment for VL. This plasmid has the advantage over previously described vectors that the V regions of different antibodies can be inserted without N-terminal amino-acid substitutions.

The CH1 sequence was also modified from the original pSW1Fab vector by the re-introduction of a cys residue for L chain interaction, the complete hinge and an extension into CH2 to promote dimerisation. This was achieved by insertion of synthetic oligonucleotide sequences between SalI and SphI sites of the original sequence (SEQ ID NO: 9 and 10) followed by insertion of further synthetic oligonucleotide sequences (SEQ ID NO: 11 and 12) between the PmlI and HpaI sites of the first insertion.

The c-terminal cys residue in CK was also restored by site directed mutagenesis to allow covalent interaction between Fd and L chains.

Figure 2:
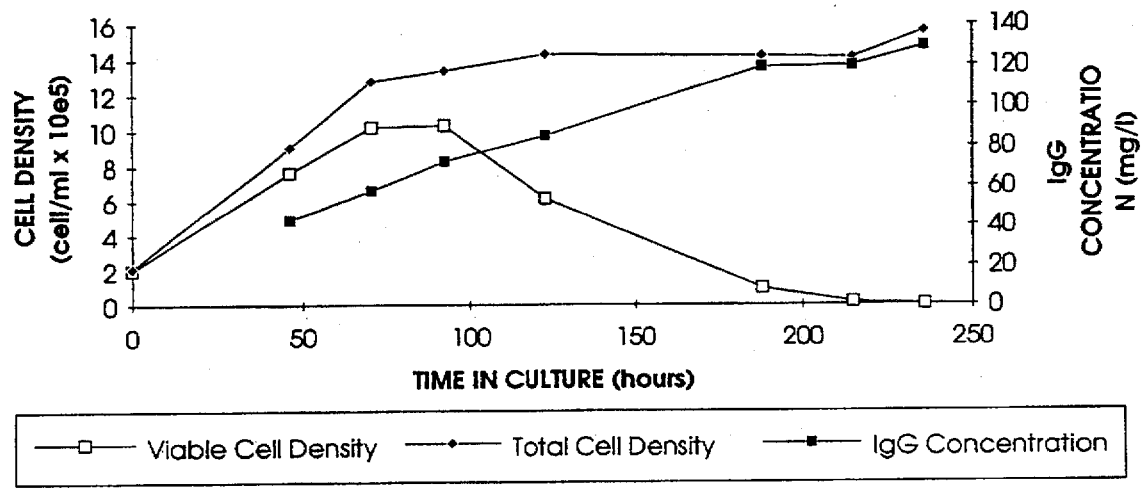
FIG. 2 shows cell density and IgG concentration on culture of 55.1 hybridoma in protein free medium.
Figure 3:
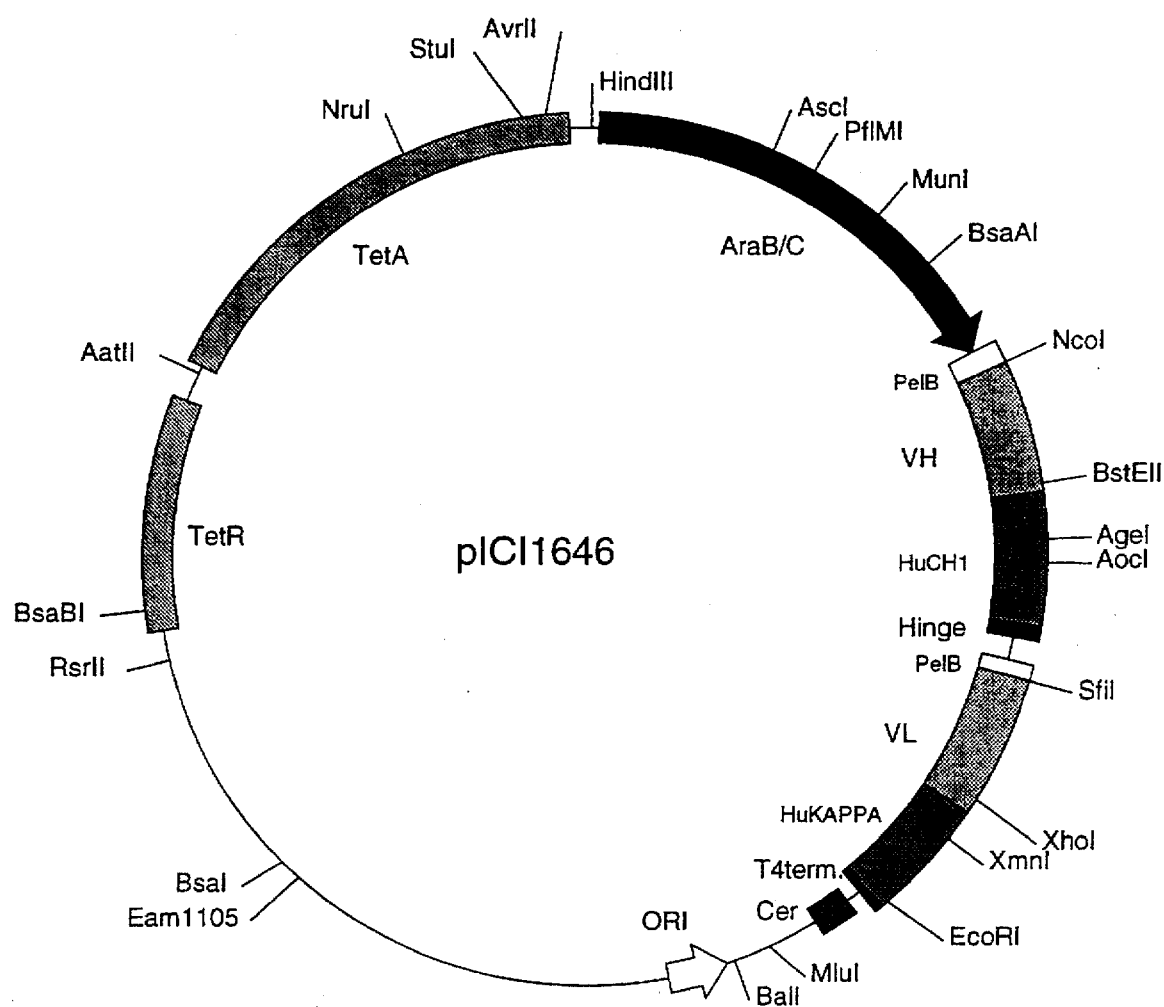
FIG. 3 shows a plasmid map of pICI1646.

Plasmid pICI1646 is shown in FIG. 2.

3.3 (b) Generation of 55.1 Fab' and F(ab')2 Expressing Clones.

3.3 (b)i Isolation of 55.1 V-Region Fragments

Synthetic oligonucleotides (SEQ ID NO: 13–16) were designed to isolate the 55.1 VH and VL regions from cDNA clones using PCR. The oligos also introduce the appropriate cloning sites (NcoI and BstEII for VH and SfiI and XhoI for VL) to allow subsequent cloning into pICI1646.

PCRs were set up containing 15 ng template DNA (55.1 H or L chain cDNA clone in pBluescript), 100 pmoles of each oligo (SEQ ID NO: 13 and 14 for VH and SEQ ID NO: 15 and 16 for VL), in a 100 μl reaction containing 200 μM dNTPs, 10 mM Tris-HCl (pH 8.3), 50 mN KCl, 1.5 mM MgCl2, 0.01% gelatin and 2.5 u Taq polymerase (Amplitaq) and overlaid with 100 μl light mineral oil. Control reactions with no DNA were set up to detect contamination of reagent solutions. All reactions were incubated at 94° C. for 1.5 minutes, 50° C. for 1.0 minutes, 72° C. for 2 minutes for 20 cycles plus 10 minutes at 72° C. in a programmable heat controller (Techne PHC-1). The PCRs were analysed by running a 5 μl sample on a 0.8% agarose gel.

The remainder of the PCR reactions containing VH and VL fragments were purified to remove excess oligos using Centricon 100 microconcentrators with 3 washes in 2 ml double-distilled water at 1000×g for 5 minutes each (as described above). The retentate containing the isolated V region fragments was retained and the DNA precipitated in 70% ethanol and 0.3M sodium acetate on ice for 10 minutes. Each DNA was then pelleted by microfuging at 13000 rpm for 10 minutes, the pellets washed in 70% ethanol and vacuum dried.

3.3(b)ii Restriction Digestion of 55.1 VH Fragment

The PCR isolated 55.1 VH product was then digested with BstEII by resuspension in a 200 µl solution containing 10 mM Tris-acetate, pH 7.5, 10 mM magnesium acetate, 50 mM potassium acetate and 25 u BstEII which was incubated at 65° C. for 1 hour. This reaction was then cooled on ice and digestion with NcoI performed by doubling buffer component concentrations, addition of 50 u NcoI and incubation at 37° C. for 1 hour. The digested DNA was treated with Strataclean resin (Stratagene Ltd.) according to the protocols provided to remove protein contamination. The DNA was ethanol precipitated and then resuspended in 20 µl of sterile double-distilled water.

The digested fragment was then electrophoresed on a 0.75% SeaPlaque GTG agarose (FMC Bio-products) gel and each fragment purified from the gel by phenol extraction according to the protocol provided. The DNA was then ethanol precipitated and resuspended in 10 µl of sterile distilled water. A 1 µl sample of each fragment was electrophoresed on a 0.8% agarose gel for estimation of DNA concentration.

3.3 (b)iii Cloning the 55.1 VH Fragment into pICI1646

A 5 µg sample of pICI1646 DNA was digested with BstEII and NcoI as for the 55.1 VH fragment above. The digested DNA was purified and the DNA concentration estimated as above.

A 10 µl ligation reaction was then set up containing 100 ng of the BstEII-NcoI vector fragment, 50 ng of the BstEII-NcoI 55.1 VH fragment and 2.5 u T4 DNA ligase in 30 mM Tris-HCl, pH 7.8, 10 mM MgCl2, 10 mM DTT and 1 mH ATP. The ligation reaction was incubated at 16° C. for 2 hours before using a 1 µl aliqout to transform 20 µl of competent E. coli DH5α cells (Life Technologies Ltd.) according to the protocols provided by the supplier. Transformed cells were plated on an L agar plate containing 10 µg/ml tetracycline which was then incubated at 37° C. overnight.

Six tetracycline resistant colonies were picked from the agar plate and each inoculated into 10 ml L broth plus 10 µg/ml tetracycline. These cultures were incubated at 37° C., shaking, overnight before being used for plasmid DNA preparation using the method of Birnboim and Doly as specified in Maniatis (Chapter 1, p38). Potential 55.1 VH clones were selected on the basis of acquisition of a unique DraIII restriction site when compared to the parental plasmid. Larger scale plasmid preparations using CsCl/EtBr density gradient centrifugation (see above under "DNA sequence analysis of cDNA clones") were made from 4 such clones and the clones verified by DNA sequence analysis according to the method of Sanger as provided in the Sequenase kit (United States Biochemical Corp.). One clone with the correct sequence was named pICI1655.

3.3(b)iv Subcloning of 55.1 VL fragment into pICI1655.

The isolated 55.1 VL fragment and pICI1655 plasmid DNA ($~$5 µg of each) were digested with 25 u SfiI in 200 µl reactions containing 10 mM Tris-HCl, pH 7.9, 10 mM MgCl2, 50 mM NaCl and 1 mM DTT and incubated at 50° C. for 1 hour. Subsequently, 24 u XhoI was added to each digest an incubation continued at 37° C. for 1 hour. The digestions were then treated with Strataclean resin, the DNA ethanol precipitated, resuspended in 20 µl sterile double-distilled water, electrophoresed on a 0.75% SeaPlaque GTG agarose gel and the appropriate vector and VL fragments isolated as specified above. The concentration of the isolated DNA fragments was estimated after running 1 µl aliquots on a 0.8% agarose gel.

A ligation was set up containing 100 ng pICI1655 SfiI-XhoI fragment, 50 ng 55.1 VL SfiI-XhoI fragment under conditions used for the 55.1 VH above. The ligation was incubated at 16° C. for 3 hours before using 1 µl to transform competent DH5α cells to tetracycline resistance. Eight tetracycline resistant colonies were selected for small scale plasmid DNA preparation. These DNAs were screened for loss of a unique SstI site when compared to the parent vector. Potential 55.1 F(ab')2 clones were chosen for larger scale plasmid DNA preparation and confirmation by DNA sequence data analysis as detailed above. One clone with the predicted 55.1 V region DNA sequences was named pICI1656.

3.3 (b)v Expression Studies

For analysis of antibody fragment expression, the pICI1656 DNA was used to transform the E. coli strains MC1000 (ATCC no. 39531) and MC1061 (ATCC no. 53338) [Casadaban, M. J. and Cohen, S. N., 1980, J. Mol. Biol., vol 138, p179–207]. These are ara- strains which are not able to metabolise the arabinose used to induce expression from the araB promoter. Competent cells from these two strains were prepared and transformed to tetracycline resistance according to methods quoted in Maniatis (Chapter 1, p74–84). Pure clones in each strain were then used for analysis of expression by Western blot and ELISA of culture supernatants.

3.3 (b) vi Preparation of Culture Supernatants

MC1000 (pICI1656) and MC1061 (pICI1656) were inoculated into 10 ml 2×YT broth plus 10 µg/ml tetracycline and incubated at 37° C., shaking, overnight. The overnight cultures were then subbed (1 in 100) into 100 ml 2×YT broth plus tetracycline. These cultures were incubated at 37° C., shaking for 3 hours. After this time the incubator heater was switched off and the temperature allowed to fall to ambient (25° C.) gradually ($~$1 hour). A 10 ml sample of each culture was taken and the OD$_{540}$ measured ($~$0.7). The sample was centrifuged (10 minutes at 2500×g) to pellet the cells and the supernatant stored at 4° C. as the pre-induction sample.

Arabinose solution (20% w/v) was added to each culture to a final concentration of 1% (w/v) and incubation continued at ambient temperature for 3 hours. After this period, a second 10 ml sample was taken, the OD$_{540}$ measured ($~$0.85) and the sample centrifuged to pellet cells. The supernatant was stored at 4° C. (after induction sample).

3.3 (b) vii Western Blot Analysis

Aliquots (15 µl ) of each supernatant sample were mixed with an equal volume of sample buffer (62.5 mM Tris, pH 6.8, 1% SDS, 10% sucrose and 0.05% bromophenol blue) with and without reductant (50 mM DTT). The samples were incubated at 100° C. for 15 minutes before electrophoresis on a 8–18% acrylamide gradient gel (Excel gel system from Pharmacia Biotechnology Products) in a multiphor apparatus (LKB Produkter AB) according to the manufacturers instructions. After electrophoresis, the separated proteins were transfered to a Hybond C-Super membrane (Amersham International) using a Novablot apparatus (LKB Produkter AB) according to protocols provided by the manufacturer. After blotting, the membrane was air dried.

The presence of antibody fragments was detected by the use of an anti-human Cκ antibody-peroxidase conjugate (Sigma Chmical Company, product A7164) with the ECL detection system (Amersham International).

The results of the Western blot analysis are shown in FIG. 9. The expression of antibody fragments is clearly detectable by the presence of a signal in the after induction samples compared to the blank pre-induction samples. In the presence of reductant, a single band of ~25 kD is detected which is consistant with free light chains. In the absence of reductant, additional bands of ~50 kD and 100 kD are seen which are consistant with the covalent association of antibody chains into Fab' and F(ab')2 fragments.

3.3 (b) viii ELISA Analysis

Standard procedures for ELISA assay are available in "Laboratory Techniques in Biochemistry and Molecular Biology" eds. Burdon, R. H. and van Kippenberg, P. H., volume 15, "Practice and Theory of Enzyme Immunoassays", Tijssen, P., 1985, Elsevier Science Publishers B. V. Another source of information is "Antibodies—A Laboratory Manual" Harlow, E. and Lane, D. P. 1988, published by Cold Spring Harbor Laboratory.

The supernatant samples were used in an ELISA to detect binding to COLO205 cells (Semple, T. et al, 1978, Cancer Res., vol 38, p1345–1355, ATCC no. CCL 322). COLO205 cells cultured in serum-free medium (Zeneca Pharmaceuticals ref. M1) were fixed to 96 well microtitre plates ($10^5$ cells per well) using glutaraldehyde (0.1% v/v solution in PBS). The culture supenatants were added to the wells and incubated at 4° C. for ~70 hours to allow binding of the antibody fragments. After washing PBS with 1% (w/v) BSA and 0.5% (v/v) Tween 20, the anti-human Cκ antibody-peroxidase conjugate (see above) was used to detect bound antibody fragments using o-Phenylenediamine (Sigma Chemical Company Ltd.) for colour development which was then measured in a ThermoMax plate reader (Molecular Devices) at 490 nm. The results of the ELISA are shown in FIG. 10. Specific binding to COLO205 by the 55.1 antibody fragments is detected in induced MC1000 and MC1061 (pICI1654) culture supernatants compared to uninduced samples and controls with the expression of other antibody fragments with alternate specificities from COLO205.

3.3 (c) Generation of a 55.1 scFV.

The rapid generation of scFv fragments from antibodies using PCR has been described (Davis, G. T. et al, 1991, Bio/Technology, vol 9, p165–169). The construction relies on linking the VH and VL regions of the antibody by a flexible peptide linker which allows folding of the V regions into an active conformation. Separate VH and VL regions containing the linker fragment are generated by PCR and the complementarity of the linker regions then used to create a gene encoding the scFv in a subsequent PCR.

3.3 (c)i Construction of a 55.1 scFv Expressing Clone.

Oligonucleotides (SEQ ID NO: 13 and 16-20) were designed to act as PCR primers. Oligo 20 encodes a (Gly4Ser)3 linker sequence and also has complementarity to the 5' region of antibody VL regions at its 3' end. Oligo 21 is the complement of the linker sequence and has complementarity to the 3' region of antibody VH sequences. Another oligo (SEQ ID NO: 21) was designed to be complemetary to the 3' region of 55.1 VL with the addition of in-frame translation termination codons and an EcoRI cloning site.

The VH and VL regions of 55.1 were isolated by PCR as described above in construction of the 55.1 F(ab')2 expressing clone using oligos 13 and 17 for VH and 16 and 18 for VL. These fragments (~0.2 pmoles of each) were mixed with oligos 19 and 20 (0.1 pmoles of each) in a 50 µl PCR reaction containing 200 µM dNTPs, 10 mM Tris-HCl (pH 8.3), 50 mM KCl, 1.5 mM MgCl2, 0.01% gelatin and 1.25 u Taq polymerase (Amplitaq) and overlaid with 50 µl light mineral oil. A control reaction without the V regions was also set up. These reactions were incubated at 94° C. for 1 minute and 63° C. for 4 minutes for 7 cycles. After this incubation a further 50 µl of a solution containing 100 pmoles of oligos 13 and 21 and 200 µM dNTPs, 10 mM Tris-HCl (pH 8.3), 50 mM KCl, 1.5 mM MgCl2, 0.01% gelatin and 1.25 u Taq polymerase (Amplitaq) was added and incubation continued at 94° C. for 1.5 minutes, 50° C. for 1.0 minutes and 72° C. for 2.5 minutes for 25 cycles plus 10 minutes at 72° C.

Analysis of the PCR reactions by agarose gel electrophoresis confirmed the presence of a putative scFv fragment (~750 bp) in comparison with the control PCR reaction. The fragment was purified, digested with NcoI and EcoRI and cloned into pICI1646 by the procedures described for construction of the F(ab')2 expressing clone above. Clones capable of expressing the scFv were subsequently identified by the presence of a 750 bp NcoI-EcoRI fragment and confirmed by DNA sequence analysis.

3.3 (c) ii Insertion of a Tag Sequence.

Detection of the scFv fragment in Western blot and ELISA is not possible with conventional reagents. By addtion of a tag peptide at the c-terminus, such analyses would be facilitated. A decapeptide c-myc tag recognised by the antibody from hybridoma mycl-9E10 (also referred to as 9E10, Munro, S. and Pelham, H., 1986, Cell, vol 46, p291–300. ECACC no. 85102202. ATCC no. CRL 1729) can be used for such purposes. This tag is available on a XhoI-EcoRI fragment from plasmid pSW1D1.3VH.VK.tag (Ward, E. S. et al, 1989, Nature, vol 341, p544–546) or can be synthesised as a pair of complementary oligonucleotides (see FIG. 18 and SEQ ID NO: 25 & 35).

A XhoI-EcoRI fragment from pSW1D1.3VH.VK.tag was purified and cloned into the scFv expressing clone described above digested with XhoI and EcoRI using standard techniques. The presence of the tag at the c-terminus of the scFv was confirmed by DNA sequence analysis. One clone with the correct construction was named pICI1657.

3.3 (c) iii Expression Studies

After transformation of MC1000 and MC1061 strains with pICI1657 plasmid DNA, analysis of expression is performed by Western blot (FIG. 11) and ELISA assay (FIG. 12) of culture supernatants as described above except that detection is performed by incubation with antibody 9E10 followed by an additional incubation for 2 hours with an anti-mouse antibody-peroxidase conjugate (Sigma Chemical Company, product A9044) prior to the addition of oxidisable substrate.

EXAMPLE 4

Preparation of Enzymically Derived F(ab)$_2$ Antigen Binding Structures 55.1 antibody was successfully cleaved by proteolysis using papain to yield the F(ab)2 fragment as set out below.

15 mg 55.1 antibody at a concentration of 3 mg/ml was dialysed against 3 mM EDTA/100 mM sodium acetate pH 5.5 buffer overnight at 4° C. 2 mg (=200 µl) papain [10 mg/ml suspension obtained from Boehringer Mannheim Gmbh, Mannheim, Germany, Cat. no. 108 014 ] was diluted with 200 µl 3 mM EDTA/100 mM sodium acetate/100 mM cysteine pH 5.5 and incubated at 37 deg C. for 30 minutes. The excess cysteine was removed from the reduced papain by chromatography of the digest, at 4 deg C., on a 5 ml column of Sephadex G25 [Pharmacia, Uppsala, Sweden] in 3 mM EDTA/100 mM sodium chloride, buffer pH 5.5. Fractions were collected and monitored by UV adsorption [A280 nm] to locate the eluted reduced papain. The concentration of reduced papain was calculated using an extinction coefficient of 2.5.

An aliquot of 500 µg reduced papain was added to the predialysed 55.1 antibody at an enzyme to antibody ratio of 1 in 30. The container was then purged with nitrogen and the mixture was incubated for 20 h at 37 deg C. in a water bath. Further reaction was stopped by the addition of 0.5 ml 100 mM N-ethyl maleimide.

The crude digest was exchanged into 1.5M glycine/3M sodium chloride buffer, pH 8.9 by overnight dialysis at 4° C. and loaded onto a 5 ml column of Protein A Fast Flow Sepharose [Pharmacia, Uppsala, Sweden], previously equilibrated in the same buffer. The column was washed with 3 column volumes of glycine/salt buffer, 3 column volumes of 100 mM sodium phosphate pH 6.0 and finally 3 column volumes of 100 mM sodium citrate pH 3.0, collecting fractions and monitoring the eluent by uv absorbance at 280 nm. The F(ab)2 does not bind to the Protein A and elutes in the glycine/salt wash, the smaller fragments elute in the phosphate wash and undigested antibody in the citrate wash, as determined by SDS PAGE. The F(ab)2 containing fractions were bulked and dialysed into phosphate buffered saline (sodium phosphate/150 mM sodium chloride pH 7.2) containing 3 mM EDTA for storage.

EXAMPLE 5

Preparation of Immunoconjugates

5.1 Antibody 55.1 Immunoconjugates

A solution of the monoclonal antibody 55.1 (200 mg) in phosphate buffered saline (sodium phosphate/150 mM sodium chloride pH 7.2) at 4.4 mg/ml was concentrated to 12 mg/ml by membrane filtration (Amicon YM10 membrane, Amicon Ltd., Stonehouse, Gloucs. U.K.) at 4° C. The concentrate was diluted with 0.5 vols of borate buffer (100 mM sodium borate pH 9.1). The protein concentration was determined by monitoring absorbance at 280 nm and the pH of the mixed solution was noted to be 8.8 ±0.1.

N-succinimidyl-3-(2-pyridyldithio) butyrate (the "linker") was dissolved in dry, redistilled dimethylformamide or acetonitrile at a concentration of 10 mg/ml. An aliquot of this solution (0.352 ml), containing 3.52 mg of N-succinimidyl-3-(2-pyridyldithio) butyrate, was added immediately to the concentrated antibody solution. The resulting solution was mixed and then allowed to stand at 15° C. for one hour. The solution was then desalted by gel permeation chromatography on a 2.6×58 cm column of G25 Sephadex (Pharmacia, Uppsala, Sweden) using a flow rate of 2 ml/min and a 50 mM sodium phosphate/150 mM sodium chloride/1 mM EDTA buffer, pH 8.0 in order to remove excess reagents and buffer exchange the derivatised antibody. Alternatively, the reaction products can be removed by crossflow filtration. The desalted derivatised antibody was pooled and the protein concentration determined by monitoring the uv absorbance at 280 nm. The extent of derivatisation with the linker was determined by the addition of excess dithiothreitol and monitoring the release of free thiopyridyl groups at 343 nm. The extent of derivatisation was found to be 4 to 6 linker groups per mole of antibody.

Recombinant ricin A was reduced by treating a solution of ricin A in phosphate buffer at pH 8 with excess dithiothreitol and concentrated by crossflow filtration. Excess reagents were removed by gel permeation chromatography on a 2.6×58 cm column of G25 Sephadex (Pharmacia, Uppsala, Sweden) using a flow rate of 2 ml/min and a 50 mM sodium phosphate/150 mM sodium chloride/1 mM EDTA buffer, pH 8.0.

Recombinant ricin A was conjugated to derivatised antibody by mixing prepared recombinant Ricin A (190 mg) and derivatised antibody (190 mg) solutions at a 1:1 w/w Ricin A/derivatised antibody ratio. Glycerol was added to 20% v/v and the vessel purged with argon. The resulting solution was maintained at 15° C. for 40 to 65 hours.

Cysteine was then added to a final concentration of 0.2 mM (and at least 10 fold molar excess over linker groups on the antibody) in order to cap excess linker groups on the antibody. The solution was mixed and maintained at 20° C. for 2–3 hours. Following capping with cysteine, a sample of the resulting immunotoxin was analysed by treatment with excess dithiothreitol and monitored at 343 nm to quantitate completion of the reaction.

The solution containing the conjugate was then concentrated by membrane filtration (Amicon YM10 membrane, Amicon Ltd., Stonehouse, Gloucs. U.K.) and applied to a 2.6×50 cm gel permeation chromatographic column (Pharmacia HR300 Sephacryl, Pharmacia, Uppsala, Sweden) at a flow rate 3 ml/min in 50 mM sodium phosphate/25 mM sodium chloride/1 mM EDTA buffer. The efficiency of this step was monitored through on-line measurement of the uv absorption of the column effluent at 280 nm and results in the separation of immunotoxin and unconjugated antibody from unconjugated Ricin A. The peak containing the mixture of immunotoxin and antibody was pooled and the protein concentration determined by monitoring absorbance at 280 nm.

The resulting solution containing both unconjugated antibody and immunotoxin was adjusted to pH 6.3 by the addition of 1M HCl and applied to a 8×26 cm column of triazine dye matrix Mimetic A6XL, (ACL plc, Cambridge, UK.), at a flow rate 1.5 ml/min. The column was washed with 100 ml starting buffer which elutes unconjugated antibody and the immunotoxin eluted with starting buffer containing 0.5M sodium chloride. The immunotoxin solution was dialysed against phosphate buffered saline, filtered through a 0.22 micron filter and stored at 4° C.

Purity of the immunotoxin was determined by SDS polyacrylamide electrophoresis and contained a total of 45 mg immunotoxin with the composition: 50 to 60% mono Ricin A derivative, 10 to 30% di Ricin A derivative, 5 to 15% tri Ricin A derivative and <10% underivatised antibody.

Alternatively the gel filtration step (removal of residual r-ricin A) and the dye affinity chromatography step (removal of residual 55.1 antibody) may be transposed in the purification sequence. In this variation of the method the conjugation mixture, immediately after blocking the unreacted linker moieties with cysteine (as described above) is diluted to a conductivity of less than 5 mS with distilled water. The pH is then adjusted to 6.0 with 1M acetic acid and the solution clarified by membrane filtration. The solution is then applied to the dye ligand column (2.5 ml gel/mg r-ricin A used in the conjugation mixture). The column is then washed with 0.68% sodium acetate pH 6.0 until the unconjugated 55.1 antibody has been washed through the column. The immunotoxin and residual r-ricin A may then be eluted from the column in 20 mM sodium phosphate buffer at pH 7.0, 0.5M with respect to the sodium chloride concentration. This eluate is then concentrated by crossflow filtration using a spiral cartridge ultrafiltration system and applied to a column of Sephacryl S300HR (2.5 ml gel for every mg of antibody used in the original conjugation reaction and in a volume <5% of the total volume of the column). The column may be equilibrated in any suitable formulation buffer such as phosphate buffered saline pH 7.2.

5.2 Antibody 55.1 F(ab)2 Immunoconjugates

The purified F(ab)2 fragment was initially derivatized with 3-(2-pyridyldithio)propionic acid N-hydroxysuccinimide ester (SPDP, Sigma Chemical Company, St. Louis, U.S.A. Cat. No. P 3415). An 8× molar excess of SPDP in acetonitrile (10 mg/ml) was added to 90 mgs of F(ab)2 protein in 50 mM sodium borate, 300 mM sodium chloride, pH 8.9 at a concentration of 4 mg/ml. After mixing well the derivatization was allowed to proceed at 24 deg C. for 60 min with no further agitation. A derivatization level of between 3 and 4 mol linker/mol antibody fragment was obtained.

Excess linker was removed by gel permeation chromatography using a 200 ml column of Pharmacia Sephadex G-25 (Pharmacia, Uppsala, Sweden) equilibrated with 50 mM sodium phosphate, 150 mM sodium chloride, 1 mM ethylene diamine tetra acetic acid, pH 8.0.

100 mg of reductant free purified ricin A chain were added to the derivatized F(ab)2 fragment in the 50 mM phosphate buffer made 20% (v/v) with respect to glycerol. The container was purged with oxygen free nitrogen before thoroughly mixing. The conjugate reaction was then allowed to proceed at 24 deg C. for 48 h.

Residual activated linker groups on the F(ab)2 fragment were then blocked by treatment of the conjugated reaction mixture with 0.2 mM cysteine at a protein concentration of 4 mg/ml.

The 25 mgs of conjugate obtained after the conjugation reaction were purified from residual r-ricin and cysteine as described in the previous example using gel chromatography involving a column of 150 ml of Sephacryl S-300HR equilibrated with phosphate buffered saline, pH 7.2. Residual F(ab)2 was removed by dye affinity chromatography (ACL Mimetic Blue). The 50 ml Mimetic Blue column was equilibrated in 50 mM sodium phosphate buffer, pH 6.5. The crude conjugate mixture was applied to the column and the unconjugated F(ab)2 washed through with the 50 mM phosphate buffer. The conjugate was eluted with 50 mM sodium phosphate buffer pH 6.5, with respect to 500 mM sodium chloride. The overall yield of the procedure was 20%.

EXAMPLE 6

Selectivity of Antibody 55.1

The selectivity of an immunotoxin is of paramount importance; failure to bind to a tumour-associated antigen would result in a lack of efficacy, and unwanted targeting to a normal tissue could result in tissue toxicity. To assess selectivity, many human normal and tumour tissues have been screened for reactivity with the antibody 55.1, using sensitive three-stage indirect immunohistology on acetone-fixed, frozen cryostat sections.

Immunohistology was carried out on sections of human tissue obtained either at resection surgery or at post mortem. To preserve optimal morphology and antigenicity, tissues were obtained as fresh as possible, cut into small pieces (about 1 cm2) and flash frozen in liquid nitrogen prior to storage at −80° C. 6 μM sections of tissue were cut on a cryostat, mounted on Vector-bonded slides (Vector Labs) and fixed in ice-cold acetone for 2 minutes before being wrapped in foil and stored at −80° C. Slides were allowed to defrost at room temperature before being unwrapped from the foil immediately prior to use. Each section was outlined with a PAP Pen, and to each section was added either 100 μl 55.1 antibody diluted to 5 μg/ml in Tris-Buffered Saline (TBS), 100 μl MOPC isotype control (Sigma, Chemical Company, St. Louis, U.S.A., Cat. No. M 9269) at 5 μg/ml in TBS, or 100 μl of a relevant positive control such as LP34 (Dako). All subsequent incubations were carried out at room temperature for 30 minutes in a humidified chamber: all wash steps were in TBS with 2 changes. After incubation, the slides were washed and 100 μl of second antibody reagent, comprising 1/50 rabbit anti mouse immunoglobulins conjugated to horse radish peroxidase (Dako Patts) and 1/5 normal human serum (Sigma) in TBS was added to each section. The slides were again incubated and washed in TBS. A final detecting antibody, 100 μl swine anti rabbit immunoglobulin conjugated to horse radish peroxidase (1/50 dilution with 1/5 normal human serum in TBS ), was added to each section, incubated and washed thoroughly. DAB substrate was prepared using 1 DAB tablet (Sigma) with 17 μl Hydrogen Peroxide in 17 ml TBS, and added dropwise through a Whatman Number 4 filter paper. After 3 minutes incubation the excess DAB was tapped off the slides and the slides were washed in TBS. After counterstaining with Mayer's Haematoxylin, sections were dehydrated in alcohols and xylene, and mounted in E-Z Mount (Shandon) before examination under a microscope.

The areas of antibody binding were visualised by brown staining on the section. A scoring system was used to evaluate the degree of binding of 55.1 antibody to tissues,

| | |
|---|---|
| +++ | = antibody binding to >75% tumours |
| ++ | = antibody binding to 50–75% tumour cells |
| + | = antibody binding to 25–50% tumour cells |
| +/− | = non-focal antibody binding to a small area of tumour cells |
| − | = no staining |

The data from the study of a panel of 18 individual colo-rectal tumours indicated that 55.1 antibody binds strongly to approximately 80% of tumours (Table 3).

Further analysis of the staining revealed that in approximately 50% of the tumours (those with scores of ++ and +++), more than 50% of cells stained positively and that the staining was evident on the baso-lateral and apical cell membranes. Thus, a large proportion of the epithelial cells within a particular tumour should be amenable to targeting. In addition, the baso-lateral expression should favour effective targeting from the blood to the antigen.

A large range of human normal tissues have been screened for reactivity with 55.1 as set out in Table 4. Such selective antibodies are rare; only 1/65,000 antibody supernatants generated or screened whilst inventing 55.1 have exhibited such a minimal extent of normal tissue reactivity.

EXAMPLE 7

Assay for Competitive Binding to CA55.1

7.1 (a) Production of Soluble COLO 205 Membrane Preparations.

All materials used should be of the highest quality available. A pellet of 10E9 COLO205 cells was suspended in 7 mls of ice cold lysis buffer (2.5% Tween 40, 10 mM Tris, 0.14M NaCl, 1 mM PMSF, 1 mM NEM, 100 μM Pepstatin, pH 7.4) to give a total volume of 10 mls. The resulting solution was stirred for one hour in an ice bath. The cells were then homogenised and centrifuged for 10 mins at 1500 g and 4° C. The supernatant was aspirated and centrifuged for 1 hour at 100,000 g and 4° C. To the pellet was added 5 mls of solubilisation buffer (10 mM HEPES, 150 mM NaCl, 50 mM Octylglucoside, 10 mM NEM, 1 mM PMSF, 0.1 mM Leupeptin, pH 7.4) and the resulting suspension was gently stirred for 30 minutes at 4° C. The solution was then centrifuged for 20 minutes at 30,000 g. The supernatant, the solubilised COLO 205 membrane preparation, was aspirated and stored at 4° C.

7.1 (b) Competition ELISA

All materials used should be of the highest quality available. Dilute solubilised COLO 205 membrane preparation 1 in 100 with coating buffer (20 mM Tris, 150 mM sodium chloride, pH 7.4) to generate the antigen stock solution. Pipette 50 μl of antigen stock solution into six wells per MAb per measurement, on a microtitre plate. Agitate gently 2 hrs room temperature, or overnight at 4° C. Add 50 μl of fixing buffer (0.5% glutaldehyde in coating buffer) to each well, leave for 3 minutes, wash the plate with TBS (50 mM Tris, 100 mM sodium chloride, pH 7.4). Add 200 μl of blocking buffer (3% BSA in coating buffer) to each well and agitate gently for 1 hr at room temperature. Stock solutions of MAb 55.1, labelled with biotin (Charo et. al. 1991 J. Biol. Chem. 266, p1415–1421), and the TEST MAb are made up in antibody buffer (1% BSA in coating buffer). These stock solutions are then combined to generate six antibody solutions containing the two MAbs in the following ratios;

Antibody solution 1. 2 mg/ml 55.1 and 200 mg/ml TEST MAb.

Antibody solution 2. 2 mg/ml 55.1 and 20 mg/ml TEST MAb.

Antibody solution 3. 2 mg/ml 55.1 and 2 mg/ml TEST MAb.

Antibody solution 4. 2 mg/ml 55.1 and 0.2 mg/ml TEST MAb.

Antibody solution 5. 2 mg/ml 55.1 and 0.02 mg/ml TEST MAb.

Antibody solution 6. 2 mg/ml 55.1.

At the end of the blocking step the plate was washed with TBS, and 100 μl of each of the antibody solutions was placed in a single well in each row. The plate was then agitated gently for 2 hours at room temperature. The plate was then washed with TBS, and 100 μl of second antibody solution (1 mg/ml anti-biotin peroxidase linked MAb in antibody buffer) was added to each well and gently agitated for 1 hr. To 99.5 mls of citrate phosphate buffer (0.5 g citric acid, 1.7 g Di-sodium hydrogen phosphate dodecahydrate in 100 mls of Milli-Q water) add 0.5 mls of hydrogen peroxide solution (1 g of Urea hydrogen peroxide in 25 mls of citrate phosphate buffer) and 80 mgs of O-phenylenediamine Dihydrochloride, to make the substrate solution. The plate was then washed with TBS and 100 μl of substrate solution was added to each well, and agitated gently. Developing colour is monitored at 495 nm. When a maximum absorbance of 0.7 AUFS is reached 50 μl of stop solution is added to each well, the plate is agitated gently for 5 minutes and the final absorbance is read. Inhibition of 55.1's binding by the TEST MAb is demonstrated by a TEST MAb concentration dependant decrease in the developed colour.

EXAMPLE 8

In Vivo Activity of Immunoconjugates Against CA55.1

The essential properties of an antibody in order for it to make an effective immunotoxin when conjugated to ricin A, are that it should bind to a cell membrane determinant on tumour cells and facilitate delivery of the ricin A across the cell membrane and to the ribosomes in order to inhibit protein synthesis and induce cytotoxicity.

The 55.1 antigen has been shown to be present at high levels on several colo-rectal tumour cell lines including COLO205, using flow cytometry. COLO 205 cells have been used for routine screening for internalisation and cytotoxicity studies. When antibody 55.1 was conjugated to recombinant ricin A a highly potent immunotoxin was generated, with an IC50 of $1\times10^{-11}$M against COLO 205 cells.

Endocytosis of 55.1 binding to COLO 205 was demonstrated as follows. A cell suspension of COLO 205 cells was concentrated to 20 million cells per ml in culture medium. Iodinated antibody was added at 1 ug/ml and incybated for 1 hour at 4° C. The cells were washed twice by centrifugation at 4° C. and then diluted in fresh medium to 1 million cells per ml. 1.5 ml of cell suspension was then added to 24 well tissue culture plates followed by incubation at 37° C. 1 ml samples were removed for processing at intervals. Cells and media supernates were separated by centrifugation. Some cell pellets were treated to remove surface bound antibody using acidified pepsin (10 mg/ml, pH 2.5, 1 ml/pellet at 37° C. for 40 min). The cells were then washed by centrifugation. Medium supernatants were treated with TCA to determine protein associated radioactivity. The radioactivity of cell pellets, pepsin treated cell pellets, media and TCA precipitates of media were all measured. Thus, surface, internalised and shed antibody (including degradation products) were quantitated.

Figure 4:
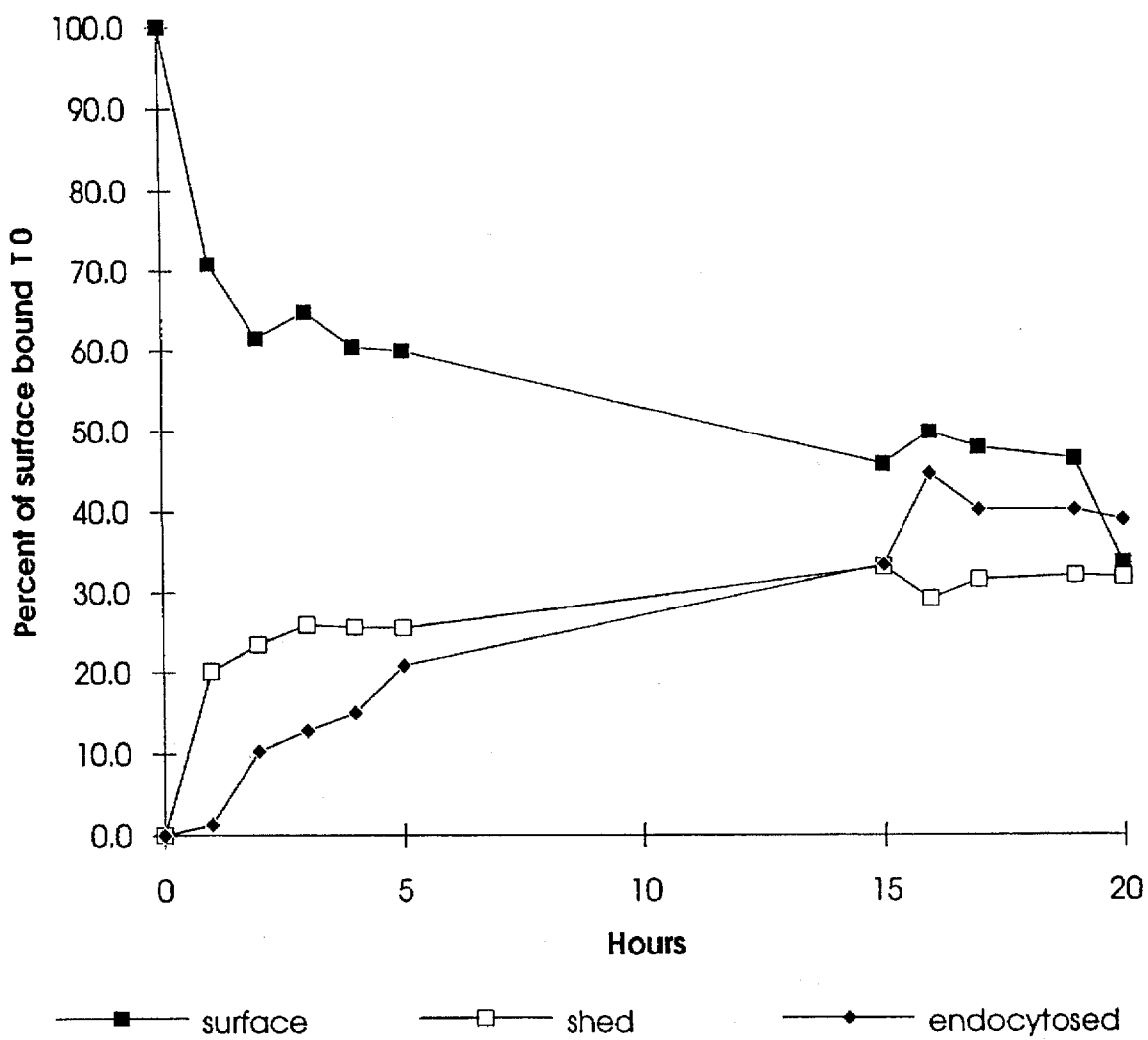
FIG. 4 shows endocytosis of CA55.1.

Compared with control non-internalising antibodies, 55.1 is efficiently internalised into COLO 205 cells, approximately 25% of the cell bound antibody crossing the cell membrane over a 4 hour in vitro incubation and 40% over a 20 hour incubation period (FIG. 4).

The in vivo potency of 55.1:ricin A has been assessed in models of human tumours grown as subcutaneous xenografts in athymic "nude" mice.

The primary anti-tumour test was carried out in groups of 10 mice implanted subcutaneously on the left flank with 5×10E6 COLO 205 cells. Tumours were allowed to grow to 0.5–0.7 cm in diameter, usually 5–7 days after implantation. At this time, 1 mg/kg 55.1:ricin A immunotoxin was dosed intravenously once a day for three days. Control groups received only iv doses of saline.

Figure 5:
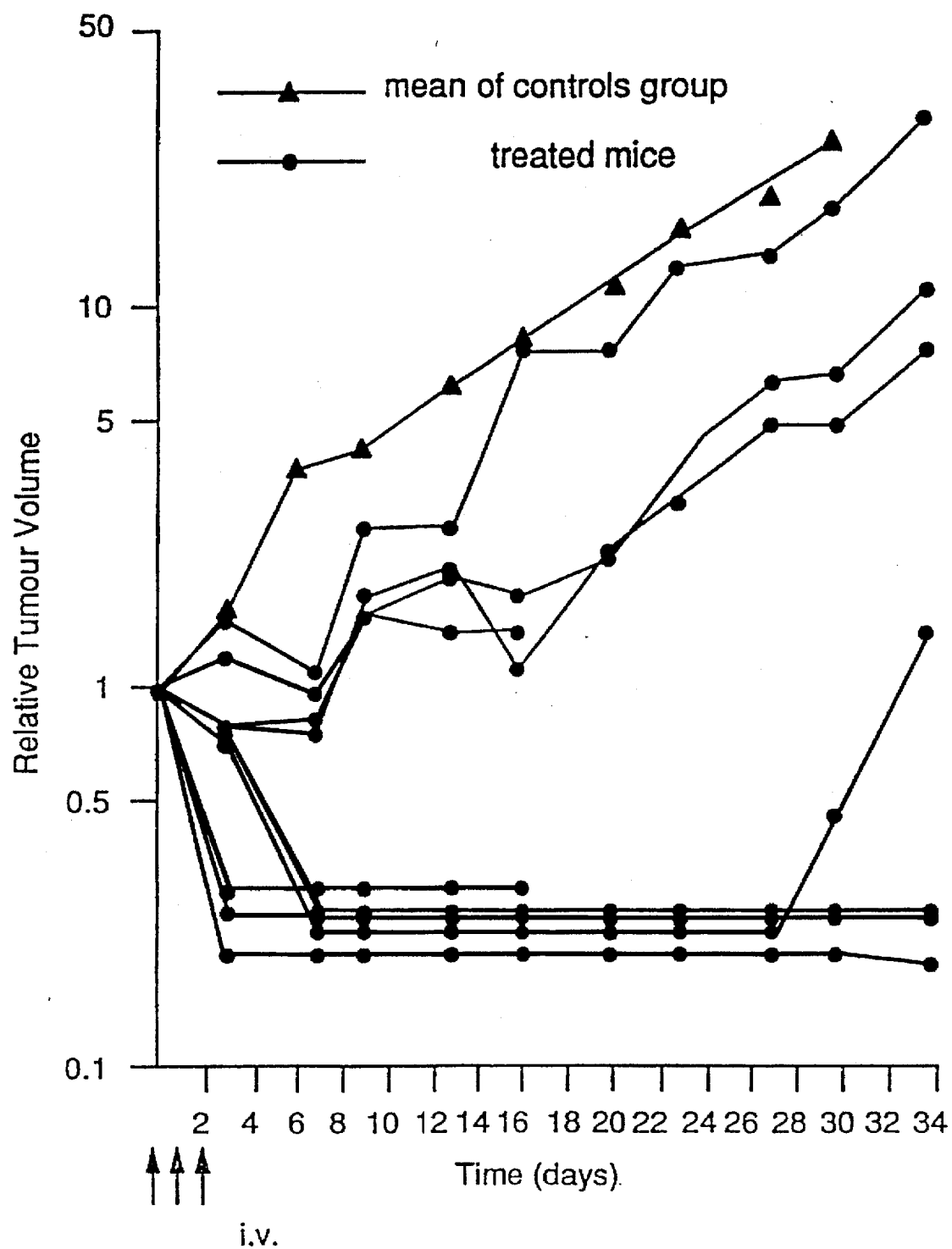
FIG. 5 shows in vivo anti-tumour effect of 55.1 antibody-ricin conjugate.

This regime produced a very substantial anti-tumour response with clear evidence of tumour regressions and complete cures in a few animals. In one such experiment, 2/10 mice were cured of their tumours. Of the remaining mice, 4/10 had moderate growth delays (10 days) and 4 had prolonged tumour growth delays of greater than 30 days (FIG. 5).

Thus, 55.1:ricin A is a highly potent, selective cytotoxic agent in vivo and is acting by targeting to and being internalised into COLO 205 cells within solid tumour xenografts. 55.1:ricin A is considerably more active, in such models, than conventional anti-cancer agents such as 5-fluorouracil.

EXAMPLE 9

Pharmaceutical Composition

The following illustrates a representative pharmaceutical dosage form containing an immunotoxin of the present invention which may be used for therapeutic purpose in humans.

| Injectable solution | |
|---|---|
| A sterile aqueous solution, for injection, containging: | |
| Ricin A/55.1 antibody immunotoxin | 1.0 mg |
| Sodium acetate trihydrate | 6.8 mg |
| Sodium chloride | 7.2 mg |
| Tween 20 | 0.05 mg per ml of solution |

EXAMPLE 10

Hybridization of DNA sequences related to the 55.1 CDR3 DNA Sequence 10.1 Hybridisation Test A method for detecting nucleic acids containing sequences related to the 55.1 antibody heavy chain gene. These nucleic acids may be present in a variety of forms such as the DNA from bacterial colonies or the DNA/RNA from eukaryotic cells fixed on to a membrane as described above in the screening of a cDNA library or as fragments of purified nuceic acid separated by gel electrophoresis and then transfered to a suitable membrane as for the techniques of Northern (Maniatis, Chapter 7, p39) or Southern (Maniatis, chapter 9, p31) hybridisation.

10.2 Hybridisation Probe

Hybridisation probes may be generated from any fragment of the DNA or RNA encoding the 55.1 H chain, more specifically from the variable region, particularly the region encoding CDR3 of this region. A synthetic oligonucleotide (SEQ ID NO: 22) or its complementary sequence can be used as a specific probe for the CDR3 encoding region.

A hybridisation probe can be generated from a synthetic oligonucleotide by addition of a radioactive 5' phospate group from 32P ATP by the action of T4 polynucleotide kinase. 20 pmoles of the oligonucleotide are added to a 20 μl reaction containing 100 mM Tris, pH 7.5 , 10 mM MgCl2, 0.1 mM Spermidine, 20 mM DTT, 7.55M ATP, 0.55M g 32P ATP and 2.5 u T4 polynucleotide kinase (Pharmacia Biotechnology Ltd, Uppsala, Sweden). The reaction is incubated for 30 minutes at 370° C. and then for 10 minutes at 70° C. prior to use in hybridisation. Methods for the generation of hybridisation probes from oligonucleotides (chapter 11) or from DNA and RNA fragments (chapter 10) are given in Maniatis. A number of proprietary kits are also available for these procedures.

10.3 Hybridisation Conditions

Filters containing the nucleic acid are pre-hybridised in 100 ml of a solution containing 6×SSC, 0.1% SDS and 0.25% Marvel™ at 65° C. for a minimum of 1 hour in a suitable enclosed vessel. A proprietary hybridisation apparatus such as model HB-1 (Techne Ltd) provides reproducible conditions for the experiment.

The pre-hybridisation solution is then replaced by 10 ml of a probe solution containing 6×SSC, 0.1% SDS, 0.25% Marvel and the oligonucleotide probe generated above. The filters are incubated in this solution for 5 minutes at 65° C. before allowing the temperature to fall gradually to below 30° C. The probe solution is then discarded and the filters washed in 100 ml 6×SSC, 0.1% SDS at room temperature for 5 minutes. Further washes are then made in fresh batches of the same solution at 30° C. and then in 10° C. increments up to 60° C. for 5 minutes per wash.

After washing, the filters are dried and used to expose an X-ray film such as Hyperfilm MP (Amersham International) at −70° C. in a light-tight film cassette using a fast tungstate intensifying screen to enhance the photographic image. The film is exposed for a suitable period (normally overnight) before developing to reveal the photographic image of the radio-active areas on the filters. Related nucleic acid sequences are identified by the presence of a photographic image compared to totally unrelated sequences which should not produce an image. Ideally, related sequences will appear positive at the highest wash temperature (60° C.). However, related sequences may only show positive at the lower wash temperatures (50°, 40° or 30° C.).

These results will also depend upon the nature of the probe used. Longer nucleic acid fragment probes will need to be hybridised for longer periods at high temperature but may remain bound to related sequences at higher wash temperatures and/or at lower salt concentrations. Shorter, mixed or degenerate oligonucleotide probes may require less stringent washing conditions such as lower temperatures and/or higher Na+ concentrations. A discussion of the considerations for hybridisation protocols is provided in Maniatis (chapter 11).

EXAMPLE 11

Analysis of CA55.1 Tumour Associated Antigen 11.1 Solubilization of CA55.1 from COLO 205 Cells.

All materials used should be of the highest quality available. A pellet of 10E9 COLO205 cells was suspended in 7 mls of ice cold lysis buffer (2.5% Tween 40, 10 mM Tris, 0.14M NaCl, 1 mM PMSF, 1 mM NEM, 100 μM Pepstatin, pH 7.4) to give a total volume of 10 mls. The resulting solution was stirred for one hour in an ice bath. The cells were then homogenised and centrifuged for 10 mins at 1500 g and 4° C. The supernatant was aspirated and centrifuged for 1 hour at 100,000 g and 4° C. To the pellet was added 5 mls of solubilisation buffer (10 mM HEPES, 150 mM NaCl, 50 mM Octylglucoside, 10 mM NEM, 1 mM PMSF, 0.1 mM Leupeptin, pH 7.4) and the resulting suspension was gently stirred for 30 minutes at 4° C. The solution was then centrifuged for 20 minutes at 30,000 g. The supernatant, the solubilised COLO 205 membrane preparation, was aspirated and stored at 4° C.

11.2 Affinity Purification of CA55.1

MAb 55.1 was coupled to CNBr activated Sepharose 4B using Pharmacia's standard protocol(Insert contained in Pharmacia CNBr Activated Sepharose, Cat. Log. No. 17-0430-01, Pharmacia AB, Uppsala Sweden). The matrix was then equilibrated into binding buffer (25 mM Tris, 150 mM NaCl, 50 mM Octyl Glucoside, pH 7.0.). The cell lysate containing the 55.1 antigen was then added to the matrix and mixed end over end at 4° C. overnight. The matrix was then washed with 6 column volumes of wash buffer (25 mM Tris, 150 mM NaCl, pH 7.0). The 55.1 antigens were then eluted by washing the matrix with 3 column volumes of elution buffer (25 mM Tris, 150 mM NaCl, 5M sodium Thiocyanate, pH 7.0.). The fractions containing the CA55.1 were identified by Western Blotting using 55.1 antibody as described below.

11.3 SDS PAGE and Western Blots of CA55.1

Samples to be analysed for MAb 55.1 reactivity are loaded onto a precast Pharmacia ExcelGel™ (8–18% gradient polyacrylamide) and run under the protocol suggested by Pharmacia using the recommended conditions (600 volts, 50 mA and 30 W for 90 minutes 15° C. see insert in Pharmacia ExcelGel Pack, Cat. No. 80-1255-53, Pharmacia, Uppsala, Sweden). The gel was removed from the backing plastic sheet and electroblotted onto PVDF membrane at 2.5 mA/cm2 for 10–12 min. After electroblotting the PVDF membrane was then transferred to blocking buffer, 3% BSA in TBS buffer (20 mM Tris, 500 mM NaCl, pH 7.4), and gently agitated for 1 hour. The membrane was then briefly rinsed with antibody buffer (1% BSA in TBS), and transferred to antibody buffer containing MAb 55.1 at a concentration of 2 mgs/L. The PVDF membrane was gently agitated for two hours.

The membrane was then briefly rinsed with Milli-Q™ water (high quality deionised water) and washed 3×5 minute in antibody buffer. The PVDF membrane was then transferred to antibody buffer containing MAb anti-mouse linked to horse radish peroxidase at a concentration of 1 mg/L. The PVDF membrane was then gently agitated for 1 h. The PVDF membrane was then briefly rinsed with Milli-Q water and washed 3×5 minutes in antibody buffer, and finally washed for 5 minutes with TBS. When the final wash step was complete the HRP colour development solution (60 mgs 4-Chloro-1-napthol in 20 mls of ice cold methanol; made within 5 min of use and stored in the dark) and the peroxide solution (60 µl of ice cold 30% $H_2O_2$ in 100 ml TBS. Made immediately prior to use) were added together and the membrane was immediately transferred into the resulting solution. When the colour had developed the reaction was stopped by washing the membrane in 2×5 min washes in Milli-Q™ water. The membrane was then air dried on tissue paper and stored.

Figure 6:
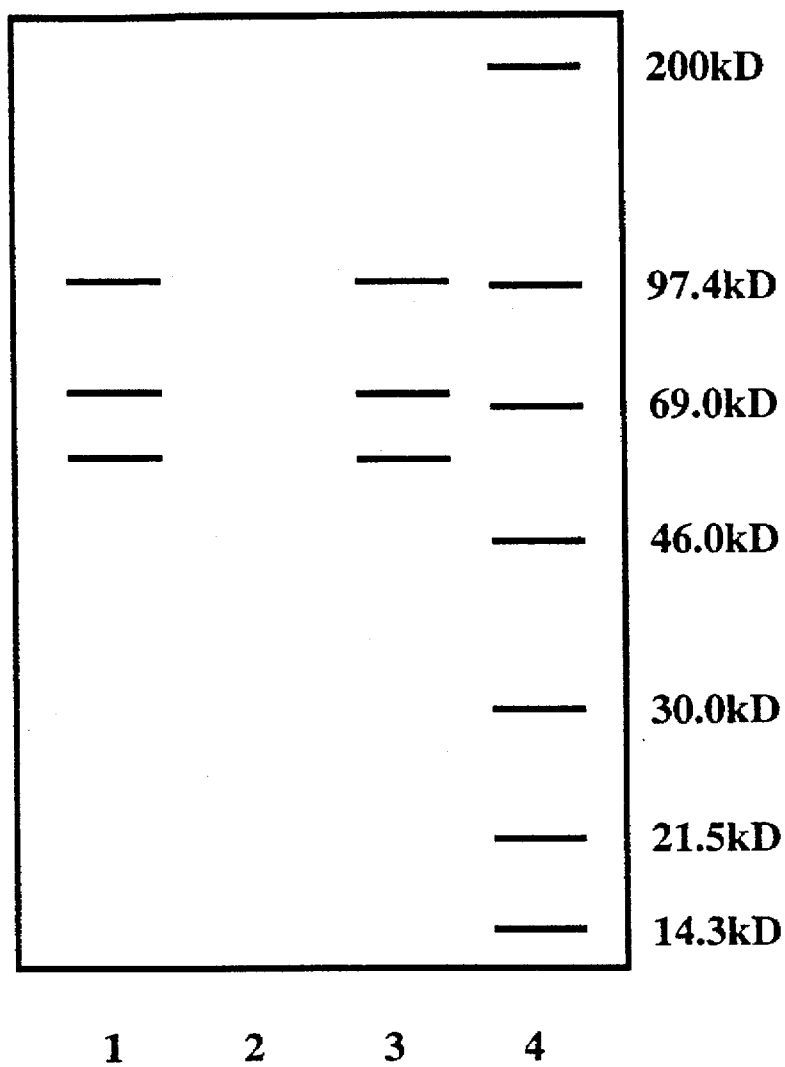
FIG. 6 shows a representation of a Western blot of PNGase treated colo 205 cells.

The results from this experiment are shown in FIG. 6. CA55.1 runs as three dominant bands molecular weights in the ranges about 48 to 52 kD, about 58 kD to 72 kD and about 88 kD to 92kd.

11.4 PNGase F Treatment, Sialidase Treatment and Lectin Blots

The carbohydrate nature of the CA55.1 epitope was demonstrated by showing the effects of the enzymes PNGase F and sialidase on CA55.1 on Western Blots. PNGase F specifically cleaves an N linked oligosaccharide from a glycoprotein between the asparagine residue and the adjacent GlcNAc residue (X-GlcNAc-GlcNAc-Asn) and is thought to be totally specific for this linkage. Sialidase cleaves non-reducing terminal sialic acids and is specific for a range of alpha 2→3,6 or 8 linkages.

11.4 (a) PNGase Treatment of CA55.1.

All materials used should be of the highest purity available. To 40 µl of COLO205 membrane preparation was added 40 µl of denaturation buffer (40 mM Sodium Hydrogen Phosphate, 0.5% SDS and 5% 2-Mercaptoethanol, pH 7.5), the resulting solution was boiled for two minutes. After cooling 2 µl Nonidet NP-40 was added (2.5% v/v). To this solution was added 20 units of PNGase F (N Glycosidase F, Ex. Boehringer Mannheim Cat. Number 913782), followed by 160 µl of digestion buffer (40 mM Sodium Hydrogen Phosphate, pH 7.5) and 160 µl of Milli Q water. The resulting solution was then incubated for 18 h at 37° C.

11.4 (b) Sialidase Treatment of CA55.1

All materials used should be of the highest purity available. Sialidase (0.1 units, Oxford Glycosystems Cat. No. X-5011) was resuspended in 10 µl of 500 mM sodium acetate buffer pH 5. The resulting solution was added to 40 µl of COLO205 membrane preparation and incubated for 18 h at 37° C.

The PNGase F and sialidase treated COLO205 membrane preparation and a sample of untreated membrane preparation were then Western blotted as described above.

FIG. 6 shows a representation of the results of the Western Blot. Track 1 contains the untreated COLO205 membrane preparation, track 2 the PNGase F treated sample and track 3 is the sialidase treated sample. Track 1 shows the three major MAb 55.1 positive species, with molecular weight of approximately 48–52 kD, 58–72 kD and 88–92 kD. Track 2 contains no detectable species. Track 3 shows 55.1 positive species with molecular weights of approximately 48–52 kD, 58–72 kD and 88–92 kD. In track 3 the 55.1 positive species were more weakly staining than the control sample in track 1; this reduction is believed to be due to partial protein precipitation during the 18 h incubation at 37° C.

These results show that treatment of a COLO205 membrane preparation with PNGase F removes MAb 55.1 reactivity but that sialidase treatment does not totally remove MAb 55.1 reactivity. Therefore MAb 55.1 recognises an N-linked oligosaccharide and that terminal sialic acid residues are not necessary for recognition.

11.4 (c) Lectin Blotting of Affinity Purified MAb 55.1 Positive Glycoproteins.

Partial structure of the carbohydrate portion of the CA55.1 antigen can be inferred from the use of proteins which specifically recognise various carbohydrate structural motifs. These proteins or lectins can be labelled with enzymes which enable their location on SDS PAGE blots to be visualised.

All materials used should be of the highest purity available. Soluble COLO205 membrane preparation was enriched in MAb 55.1 positive glycoproteins by binding, washing and elution from a MAb 55.1 coupled affinity column. This enriched fraction, together with the recommended glycoprotein controls, was then Western Blotted and probed using Boehringer Mannheim DIG labelled lectins according to the manufacturers protocols (DIG Glycan Differentiation Kit, Boehringer Mannheim Cat. Number 1210238).

FIG. 7 shows a representation of the reactivity of 4 control and MAb 55.1 positive glycoproteins with Datura stramonium agglutinin (DSA) and Galanthus nivalis agglutinin (GNA). FIG. 7A shows that DSA cross reacts with the two high molecular weight MAb 55.1 positive glycoproteins, 58–72 kD and 88–92 kD, loaded in tracks 6 & 7. No crossreactivity was seem with the lowest molecular weight MAb 55.1 positive glycoprotein 48–52 kD; this lack of crossreactivity is probably due to insufficient loading.

FIG. 7B shows that there is no detectable cross reactivity between GNA and the MAb 55.1 positive glycoproteins loaded in tracks 6 and 7. In both cases track 7 has a ×5 higher loading than track 6 and the correct cross-reactivities were seen for the glycoprotein controls.

The lectin DSA cross reacts with Galactose-beta(1-4)-N-acetylglucosamine, this disaccharide is present in complex and hybrid N-linked glycans. DSA also recognises this disaccharide in O-linked glycans. The lectin GNA cross reacts with terminally linked mannose residues found on high mannose and hybrid N-linked glycans. This lectin will also cross react with terminal mannose residues on O-linked glycans. Since PNGase treated COLO205 membrane preparations are not MAb 55.1 positive, MAb 55.1 recognises a N-linked glycan. The positive result with DSA shows that this glycan contains the Galactose-beta(1-4)-N-acetylglucosamine disaccharide. The negative result with GNA shows that the MAb 55.1 positive glycan does not contain a terminal mannose group, and therefore cannot be of the high mannose or hybrid types. These results together demonstrate that MAb 55.1 recognises a complex N-linked glycan, containing the Galactose-beta(1-4)-N-acetylglucosamine disaccharide unit.

EXAMPLE 12

Propagation, Titration and Storage of Phage Displaying the ACEHRGSGWC Sequence (ACEHRGSGWC Phage)

ACEHRGSGWC phage (NCIMB No 40638; SEQ ID No 26) were propagated in *E. coli* K12, strain TG1 (deposited with the phage at NCIMB) as follows. TG1 cells taken from single colonies, maintained on minimal medium agar plates (prepared as described below) to maintain the F pilus, were grown in liquid culture to stationary phase at 37 degrees C., with shaking, in 2×YT (Yeast-Tryptone) broth (Difco). Aliquots of stationary phase culture (2 ml) were inoculated into fresh flasks containing 100 ml 2×YT broth and grown, with shaking at 37 degrees C., to mid-log phase. ACEHRGS-GWC phage (10E11 plaque-forming units) were added to the cultures and the flasks left to stand for 10 min at 37 degrees C. to allow adsorption of phage to the F pili of E coli and insertion of the viral DNA. The cultures were then incubated at 37 degrees C. with shaking for 5 hr to allow phage replication to take place.

Cells were separated from the phage-containing supernatant by centrifugation at 10000 rpm for 10 min at 4 degrees C. in a Sorvall GSA or similar rotor. The supernatant was heated to 65 degrees C. for 15 min to kill any residual cells, following which a solution of 20% w/v polyethylene glycol (PEG) in 2.5M NaCl was added at 20 ml per 100 ml of culture supernatant. The mixture was shaken vigorously and incubated for at least 4 hr at 4 degrees C. to precipitate the phage particles. Phage were harvested by centrifugation as above, the supernatant discarded, and phage pellets resuspended in 50 mM tris/HCl, 150 mM NaCl, pH 7.5 (TBS) at 1 ml per 100 ml original culture supernatant. Where necessary, phage were reprecipitated with PEG as above to obtain more highly purified preparations. Phage were stored in TBS, either at −20 degrees C., or at 4 degrees C. in the presence of 0.02% w/v sodium azide with no noticeable difference in subsequent viability.

Minimal medium plates were prepared by autoclaving 1.8% w/v agar (Difco) in 400 ml water. After cooling to about 50 degrees the following ingredients were added: 5×M9 salts (100 ml); 1M magnesium sulphate (500 microliters); 0.1M calcium chloride (500 microliters); 4 mg/ml thiamine (500 microliters); 20% w/v glucose (5 ml).

EXAMPLE 13

Titration of Numbers of ACEHRGSGWC Phage

Numbers of viable ACEHRGSGWC phage (SEQ ID No 26) were estimated from the numbers of plaque-forming units present in E. coli indicator cells grown in solid culture. E. coli strain TG1 cells were grown to mid-log phase as described above, and 200 microliter aliquots infected with 50 microliter aliquots of a serial dilution of phage in TBS containing 1 mg/ml bovine serum albumin (TBS-BSA). The cells were stood at room temperature for 10 min to allow adsorption of phage and injection of viral DNA, diluted to 4 ml with 0.75% w/v Bacto-Agar (Difco) in 2×YT broth maintained at 48 degrees C., then immediately poured into 90 mm diameter Petri dishes previously filled with 20 ml 1.5% Bacto-Agar in 2×YT broth. The plates were incubated overnight at 37 degrees C. to develop phage plaques which were counted to estimate the numbers of viable phage in the stock suspensions being assayed.

EXAMPLE 14

Determination of ACEHRGSGWC Phage Binding Specificity by ELISA 14.1 Specificity of Direct Binding to MAb 55.1

Specificity was determined by direct binding of phage in suspension to MAb 55.1 (ECACC No. 93081901), MAb 19.9 (hybridoma ATCC No. NS 1116 ND) and MAb C242 (Kabi-Pharmacia, Uppsala, Sweden) immobilised to polystyrene as follows. Wells of polystyrene microtitre plates (Nunc, Life Technologies Ltd, UK) were coated overnight at 4 degrees C. with 50 microliter aliquots of MAb at 0.1 mg/ml in 0.1M sodium bicarbonate buffer, 0.02% sodium azide, pH 8.6 (bicarbonate-azide). Plates were blocked for 2 hr at room temperature with 400 microliter aliquots of 30 mg/ml BSA in bicarbonate-azide, followed by 3×400 microliter washes of TBS-BSA per well, each wash lasting 5 min.

Serial dilutions of ACEHRGSGWC phage were applied in 100 microliter aliquots of TBS-BSA to the antibody-coated plates and incubated overnight at 4 degrees C., after which plates were washed with 3×400 microliter aliquots of TBS-BSA containing 0.05% w/v tween 20 (TBS-BSA-tween). Sheep anti-M13 horseradish peroxidase conjugate (Pharmacia, Milton Keynes, UK) at 1:2500 dilution in TBS-BSA was added in 100 microliter aliquots to each well and incubated for 2 hr at room temperature. Plates were again washed with 3×400 microliter aliquots of TBS-BSA-tween and developed with 200 microliter aliquots of OPD substrate (10 mg ortho-phenylenediamine, 12.5 microliters 30% hydrogen peroxide solution per 25 ml 0.1M citrate-phosphate buffer, pH 5.0). The colour reactions were stopped by the addition of 50 microliter aliquots of 0.5M citric acid and absorbance read at 450 nm.

Results (FIG. 13) showed that binding of ACEHRGS-GWC phage to MAb 55.1 was specific and saturable. Half-saturation of binding of ACEHRGSGWC phage to MAb 55.1 occurred at 2×10E7 phage input in a volume of 100 microliters.

A measure of the binding affinity was derived from Avogadro's Number, where a 1 molar solution will contain 6×10E23 molecules of solute per liter or 6×10E19 molecules per 100 microliters. Working away from this number, 2×10E7 phage per 100 microliters corresponds to a concentration of 0.3 pM whole phage particles or 1.5 pM phage-displayed peptide (there are about 5 pIII molecules present on each M13 phage particle). Thus it can be inferred that the EC50, ie the concentration of peptide-phage required for 50% saturation of MAb 55.1 is in the region of 1 pM.

14.2 Specificity of Binding to MAb 55.1 in Colo 205 Competition Assay

Specificity was determined by an assay in which ACE-HRGSGWC phage competed with MAb 55.1 in solution for the epitope of the MAb immobilised on polystyrene. Wells of microtitre plates were coated for 30 min with 100 microliter aliquots of 10^ Colo 205 cells (ATCC No CCL 222) in phosphate-buffered saline (50 mM sodium phosphate, 150 mM sodium chloride, pH 7.4) (PBS), fixed by the addition of an equal volume of 1% v/v glutaraldehyde in PBS for 15 min and blocked with 10% w/v BSA in PBS (PBS-BSA) for 2 hr, all operations performed at room temperature. Plates were washed for 3×5 min with 400 microliter aliquots PBS per well and stored in a humid box at 4 degrees C. until required (up to 1 month after coating).

Serial dilutions of ACEHRGSGWC phage were incubated overnight at 4 degrees C. with MAbs 55.1, 19.9 and C242, all at 20 micrograms/ml in 250 microliters PBS containing 10% w/v BSA and 0.005% w/v tween 20 (phage diluent buffer), after which duplicate 100 microliter aliquots were pipetted into wells of prepared Colo 205 plates and incubated for 3 hours at room temperature to allow interaction between the reactants. Plates were washed for 3×5 min with PBS containing 0.05% w/v tween 20 (PBS-tween buffer) and 100 microliter aliquots of rabbit anti-mouse IgG horseradish peroxidase conjugate (Sigma, Poole, UK) at 1:1000 dilution in phage diluent buffer added per well.

Plates were incubated for 2 hr at room temperature, washed for 3×5 min with PBS-tween buffer and colour developed with OPD substrate.

Results (FIG. 14) showed that binding of MAb 55.1 to Colo 205 cells, but not that of MAbs 19.9 and C242 was inhibitable by ACEHRGSGW phage, with an IC50 of 10E12 phage input in a volume of 100 microliters.

A measure of binding affinity was derived as above from Avogadro's Number. If 6×10E19 molecules of solute per 100 microliters corresponds to a 1 molar solution, then 10E12 phage particles in 100 microliters corresponds to 16.7 nM concentration of whole particles or 80 nM phage-displayed peptide. Thus it can be inferred that the IC50 ie the concentration of phage required to achieve 50% inhibition of MAb 55.1 binding to its antigen on Colo 205 cells is of the order of 20–100 nM.

Sequences

In the event that the reader encounters any errors, omissions or other discrepancies he is specifically directed to the nucleic acid and amino acid sequences disclosed in priority documents UK 9324918.3 (filed Mar. 12, 1993) and UK 9411089.7 (filed Mar. 6, 1994).

SEQUENCE LISTING ( 1 ) GENERAL INFORMATION:

( i i i ) NUMBER OF SEQUENCES: 37

( 2 ) INFORMATION FOR SEQ ID NO: 1:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 1:

CAGGTCCAAC TGCAGCAGCC TGGGGCTGA  29

( 2 ) INFORMATION FOR SEQ ID NO: 2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 2:

CARGTCCARC TGCARCARCC TGGGGCTGA  29

( 2 ) INFORMATION FOR SEQ ID NO: 3:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 3:

GATATTGTGA TGTCTCAGTC TCCA  24

( 2 ) INFORMATION FOR SEQ ID NO: 4:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 4:

```
GATATTGTGA TGTCTCAGTC TNCC                                                      24
```

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
AGATCCAGGG GCCAGTGGAT AGACAGATGG                                                 30
```

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
TGGGAAGATG GATACAGTTG GTGCAGCATC                                                 30
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
TAATACGACT CACTATAGGG                                                            20
```

(2) INFORMATION FOR SEQ ID NO: 8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
TACTTCTGGG ACTGTACATA TTCAAGGCCT CGAGCCACAA TC                                   42
```

(2) INFORMATION FOR SEQ ID NO: 9:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
TCGACAAGAA AGTTGAGCCC AAATCTTGTG ACAAGACGCA CACGTGCGGA GGTTAATAAG               60
CTAGCGTTAA CATG                                                                  74
```

( 2 ) INFORMATION FOR SEQ ID NO: 10:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 10:

```
TTAACGCTAG CTTATTAACC TCCGCACGTG TGCGTCTTGT CACAAGATTT GGGCTCAACT    60

TTCTTG                                                               66
```

( 2 ) INFORMATION FOR SEQ ID NO: 11:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 11:

```
GTGCCCGCCG TGCCCGGCTC CGGAACTGCT GGGTGGCCCG TAATAGCTAG CGTT          54
```

( 2 ) INFORMATION FOR SEQ ID NO: 12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 12:

```
AACGCTAGCT ATTACGGGCC ACCCAGCAGT TCCGGAGCCG GGCACGGCGG GCAC          54
```

( 2 ) INFORMATION FOR SEQ ID NO: 13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 13:

```
CAACCAGCCA TGGCCCAGGT CCAACTGCAG CAGCCTGGGG                          40
```

( 2 ) INFORMATION FOR SEQ ID NO: 14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 14:

```
TTGGCAGAGG AGACGGTGAC CGAGGTTCCT                                     30
```

( 2 ) INFORMATION FOR SEQ ID NO: 15:

( i ) SEQUENCE CHARACTERISTICS:

-continued (A) LENGTH: 60 base pairs
    (B) TYPE: nucleic acid
    (C) STRANDEDNESS: single
    (D) TOPOLOGY: linear ( i i ) MOLECULE TYPE: DNA (genomic)

( x i ) SEQUENCE DESCRIPTION: SEQ ID NO: 15:

ATTGTTATTA CTCGCGGCCC AACCGGCCCA GGCCGACATT GTGATGTCAC AGTCTCCATC    60

( 2 ) INFORMATION FOR SEQ ID NO: 16:

( i ) SEQUENCE CHARACTERISTICS:
        (A) LENGTH: 30 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO: 16:

ATCAGCCCGT TTGATCTCGA GCTTGGTGCC    30

( 2 ) INFORMATION FOR SEQ ID NO: 17:

( i ) SEQUENCE CHARACTERISTICS:
        (A) LENGTH: 32 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO: 17:

TGAGGAGACG GTGACCGTGG TCCCTTGGCC CC    32

( 2 ) INFORMATION FOR SEQ ID NO: 18:

( i ) SEQUENCE CHARACTERISTICS:
        (A) LENGTH: 24 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO: 18:

GACATTGAGC TCACCCAGTC TCCA    24

( 2 ) INFORMATION FOR SEQ ID NO: 19:

( i ) SEQUENCE CHARACTERISTICS:
        (A) LENGTH: 92 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO: 19:

GGACCACGGT CACCGTCTCC TCAGGTGGCG GTGGCTCGGG CGGTGGTGGG TCGGGTGGCG    60

GCGGATCTGA CATTGAGCTC ACCCAGTCTC CA    92

( 2 ) INFORMATION FOR SEQ ID NO: 20:

( i ) SEQUENCE CHARACTERISTICS:
        (A) LENGTH: 93 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 20:

```
TGGAGACTGG GTGAGCTCAA TGTCAGATCC GCCGCCACCC GACCCACCAC CGCCCGAGCC      60
ACCGCCACCT GAGGAGACGG TGACCGTGGT CCC                                   93
```

(2) INFORMATION FOR SEQ ID NO: 21:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 21:

```
TCTAGGAATT CGAGCTGGAT CCTTACTATT TGATCTCGAG CTTGG                      45
```

(2) INFORMATION FOR SEQ ID NO: 22:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 22:

```
GAGAGGGCCT ATGGTTACGA CGATGCTATG GACTAC                                36
```

(2) INFORMATION FOR SEQ ID NO: 23:

(i) SEQUENCE CHARACTERISTICS:
    (A) LENGTH: 1572 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 23:

```
CGCGGCCGCC AGTTCTCTCT ACAGTTACTG AGCACACAGG ACCTCACCAT GGGATGGAGC      60
TATATCATCC TCTTTTTGGT AGCAACAGGT ACAGATGTCC ACTCCCAGGT CCAACTGCAG     120
CAGCCTGGGG CTGAACTGGT GAAGCCTGGG GCTTCAGTGC AGCTGTCCTG CAAGGCTTCT     180
GGCTACACCT TCACCGGCTA CTGGATACAC TGGGTGAAGC AGAGGCCTGG ACAAGGCCTT     240
GAGTGGATTG GAGAGGTTAA TCCTAGTACC GGTCGTTCTG ACTACAATGA GAAGTTCAAG     300
AACAAGGCCA CACTGACTGT AGACAAATCC TCCACCACAG CCTACATGCA ACTCAGCAGC     360
CTGACATCTG AGGACTCTGC GGTCTATTAC TGTGCAAGAG AGAGGGCCTA TGGTTACGAC     420
GATGCTATGG ACTACTGGGG TCAAGGAACC TCAGTCACCG TCTCCTCTGC CAAAACGACA     480
CCCCCATCTG TCTATCCACT GGCCCCTGGA TCTGCTGCCC AAACTAACTC CATGGTGACC     540
CTGGGATGCC TGGTCAAGGG CTATTTCCCT GAGCCAGTGA CAGTGACCTG GAACTCTGGA     600
TCCCTGTCCA GCGGTGTGCA CACCTTCCCA GCTGTCCTGC AGTCTGACCT CTACACTCTG     660
AGCAGCTCAG TGACTGTCCC CTCCAGCACC TGGCCCAGCG AGACCGTCAC CTGCAACGTT     720
GCCCACCCGG CCAGCAGCAC CAAGGTGGAC AAGAAAATTG TGCCCAGGGA TTGTGGTTGT     780
AAGCCTTGCA TATGTACAGT CCCAGAAGTA TCATCTGTCT TCATCTTCCC CCCAAAGCCC     840
```

```
AAGGATGTGC TCACCATTAC TCTGACTCCT AAGGTCACGT GTGTTGTGGT AGACATCAGC      900
AAGGATGATC CCGAGGTCCA GTTCAGCTGG TTTGTAGATG ATGTGGAGGT GCACACAGCT      960
CAGACGCAAC CCCGGGAGGA GCAGTTCAAC AGCACTTTCC GCTCAGTCAG TGAACTTCCC     1020
ATCATGCACC AGGACTGGCT CAATGGCAAG GAGTTCAAAT GCAGGGTCAA CAGTGCAGCT     1080
TTCCCTGCCC CCATCGAGAA AACCATCTCC AAAACCAAAG GCAGACCGAA GGCTCCACAG     1140
GTGTACACCA TTCCACCTCC CAAGGAGCAG ATGGCCAAGG ATAAAGTCAG TCTGACCTGC     1200
ATGATAACAG ACTTCTTCCC TGAAGACATT ACTGTGGAGT GGCAGTGGAA TGGGCAGCCA     1260
GCGGAGAACT ACAAGAACAC TCAGCCCATC ATGGACACAG ATGGCTCTTA CTTCGTCTAC     1320
AGCAAGCTCA ATGTGCAGAA GAGCAACTGG GAGGCAGGAA ATACTTTCAC CTGCTCTGTG     1380
TTACATGAGG GCCTGCACAA CCACCATACT GAGAAGAGCC TCTCCCACTC TCCTGGTAAA     1440
TGATCCCAGT GTCCTTGGAG CCCTCTGGTC CTACAGGACT CTGACACCTA CCTCCACCCC     1500
TCCCTGTATA AATAAAGCAC CCAGCACTGC CTTGGGACCC TGCAAAAAAA AAAAAAAAA     1560
AAAGCGGCCG CG                                                       1572
```

( 2 ) INFORMATION FOR SEQ ID NO: 24:

( i ) SEQUENCE CHARACTERISTICS:
    ( A ) LENGTH: 940 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 24:

```
GCGGCCGCGA TGGATTCACA GGCCCAGGTT CTTATATTGC TGCTGCTATG GGTATCTGGA       60
ACCTGTGGGG ACATTGTGAT GTCACAGTCT CCATCCTCCC TGGCTGTGTC AGCAGGAGAG      120
AAGGTCACCA TGAGCTGCAA ATCCAGTCAG AGTCTCCTCA ACAGTAGAAC CCGAAAGAAC      180
TACTTGGCTT GGTACCAGCA GAGACCAGGG CAGTCTCCTA AACTGCTGAT CTATTGGGCA      240
TCCACTAGGA CATCTGGGGT CCCTGATCGC TTCACAGGCA GTGGATCTGG GACAGATTTC      300
ACTCTCACCA TCAGCAGTGT GCAGGCTGAA GACCTGGCAA TTTATTACTG CAAGCAATCT     360
TATACTCTTC GGACGTTCGG TGGAGGCACC AAGCTGGAAA TCAAACGGGC TGATGCTGCA      420
CCAACTGTAT CCATCTTCCC ACCATCCAGT GAGCAGTTAA CATCTGGAGG TGCCTCAGTC      480
GTGTGCTTCT TGAACAACTT CTACCCCAAA GACATCAATG TCAAGTGGAA GATTGATGGC      540
AGTGAACGAC AAAATGGCGT CCTGAACAGT TGGACTGATC AGGACAGCAA AGACAGCACC      600
TACAGCATGA GCAGCACCCT CACGTTGACC AAGGACGAGT ATGAACGACA TAACAGCTAT      660
ACCTGTGAGG CCACTCACAA GACATCAACT TCACCCATTG TCAAGAGCTT CAACAGGAAT      720
GAGTGTTAGA GACAAAGGTC CTGAGACGCC ACCACCAGCT CCCAGCTCC ATCCTATCTT       780
CCCCTTCTAA GGTCTTGGAG GCTTCCCCAC AAGCGACCTA CCACTGTTGC GGTGCTCCAA      840
ACCTCCTCCC CACCTCCTTC TCCTCCTCCT CCCTTTCCTT GGCTTTATC ATGCTAATAT       900
TTGCAGAAAA TATTCAATAA AGTGAGTCTT TGGCGGCCGC                            940
```

( 2 ) INFORMATION FOR SEQ ID NO: 25:

( i ) SEQUENCE CHARACTERISTICS:
    ( A ) LENGTH: 82 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 25:

```
TCGAGATCAA ACGGGAACAA AAACTCATCT CAGAAGAGGA TCTGAATTAA TAATGATCAA      60
ACGGTAATAA GGATCCAGCT CG                                               82
```

( 2 ) INFORMATION FOR SEQ ID NO: 26:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 26:

```
Ala Cys Glu His Arg Gly Ser Gly Trp Cys
 1               5                   10
```

( 2 ) INFORMATION FOR SEQ ID NO: 27:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 27:

```
Gly Tyr Trp Ile His
 1               5
```

( 2 ) INFORMATION FOR SEQ ID NO: 28:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 28:

```
Glu Val Asn Pro Ser Thr Gly Arg Ser Asp Tyr Asn Glu Lys Phe Lys
 1               5                   10                  15
Asn
```

( 2 ) INFORMATION FOR SEQ ID NO: 29:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 29:

```
Glu Arg Ala Tyr Gly Tyr Asp Asp Ala Met Asp Tyr
 1               5                   10
```

( 2 ) INFORMATION FOR SEQ ID NO: 30:

( i ) SEQUENCE CHARACTERISTICS:
  ( A ) LENGTH: 17 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO: 30:

```
Lys Ser Ser Gln Ser Leu Leu Asn Ser Arg Thr Arg Lys Asn Tyr Leu
1               5                   10                  15
Ala
```

(2) INFORMATION FOR SEQ ID NO: 31:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 31:

```
Trp Ala Ser Thr Arg Thr Ser
1               5
```

(2) INFORMATION FOR SEQ ID NO: 32:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 32:

```
Lys Gln Ser Tyr Thr Leu Arg Thr
1               5
```

(2) INFORMATION FOR SEQ ID NO: 33:

(i) SEQUENCE CHARACTERISTICS:
(A) LENGTH: 445 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 33:

```
Gln Val Gln Leu Gln Gln Pro Gly Ala Glu Leu Val Lys Pro Gly Ala
1               5                   10                  15

Ser Val Gln Leu Ser Cys Lys Ala Ser Gly Tyr Thr Phe Thr Gly Tyr
                20                  25                  30

Trp Ile His Trp Val Lys Gln Arg Pro Gly Gln Gly Leu Glu Trp Ile
            35                  40                  45

Gly Glu Val Asn Pro Ser Thr Gly Arg Ser Asp Tyr Asn Glu Lys Phe
        50                  55                  60

Lys Asn Lys Ala Thr Leu Thr Val Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Arg Ala Tyr Gly Tyr Asp Asp Ala Met Asp Tyr Trp Gly
                100                 105                 110

Gln Gly Thr Ser Val Thr Val Ser Ser Ala Lys Thr Thr Pro Pro Ser
```

|     |     | 115 |     |     |     | 120 |     |     |     | 125 |     |     |     |     |
|-----|-----|-----|-----|-----|-----|-----|-----|-----|-----|-----|-----|-----|-----|-----|
| Val | Tyr | Pro | Leu | Ala | Pro | Gly | Ser | Ala | Ala | Gln | Thr | Asn | Ser | Met | Val |
|     | 130 |     |     |     |     | 135 |     |     |     | 140 |     |     |     |     |
| Thr | Leu | Gly | Cys | Leu | Val | Lys | Gly | Tyr | Phe | Pro | Glu | Pro | Val | Thr | Val |
| 145 |     |     |     |     | 150 |     |     |     |     | 155 |     |     |     |     | 160 |
| Thr | Trp | Asn | Ser | Gly | Ser | Leu | Ser | Ser | Gly | Val | His | Thr | Phe | Pro | Ala |
|     |     |     |     | 165 |     |     |     |     | 170 |     |     |     |     | 175 |     |
| Val | Leu | Gln | Ser | Asp | Leu | Tyr | Thr | Leu | Ser | Ser | Ser | Val | Thr | Val | Pro |
|     |     |     | 180 |     |     |     |     | 185 |     |     |     |     | 190 |     |     |
| Ser | Ser | Thr | Trp | Pro | Ser | Glu | Thr | Val | Thr | Cys | Asn | Val | Ala | His | Pro |
|     |     | 195 |     |     |     |     | 200 |     |     |     |     | 205 |     |     |     |
| Ala | Ser | Ser | Thr | Lys | Val | Asp | Lys | Lys | Ile | Val | Pro | Arg | Asp | Cys | Gly |
|     | 210 |     |     |     |     | 215 |     |     |     |     | 220 |     |     |     |     |
| Cys | Lys | Pro | Cys | Ile | Cys | Thr | Val | Pro | Glu | Val | Ser | Ser | Val | Phe | Ile |
| 225 |     |     |     |     | 230 |     |     |     |     | 235 |     |     |     |     | 240 |
| Phe | Pro | Pro | Lys | Pro | Lys | Asp | Val | Leu | Thr | Ile | Thr | Leu | Thr | Pro | Lys |
|     |     |     |     | 245 |     |     |     |     | 250 |     |     |     |     | 255 |     |
| Val | Thr | Cys | Val | Val | Val | Asp | Ile | Ser | Lys | Asp | Asp | Pro | Glu | Val | Gln |
|     |     |     | 260 |     |     |     |     | 265 |     |     |     |     | 270 |     |     |
| Phe | Ser | Trp | Phe | Val | Asp | Asp | Val | Glu | Val | His | Thr | Ala | Gln | Thr | Gln |
|     |     | 275 |     |     |     |     | 280 |     |     |     |     | 285 |     |     |     |
| Pro | Arg | Glu | Glu | Gln | Phe | Asn | Ser | Thr | Phe | Arg | Ser | Val | Ser | Glu | Leu |
|     | 290 |     |     |     |     | 295 |     |     |     |     | 300 |     |     |     |     |
| Pro | Ile | Met | His | Gln | Asp | Trp | Leu | Asn | Gly | Lys | Glu | Phe | Lys | Cys | Arg |
| 305 |     |     |     |     | 310 |     |     |     |     | 315 |     |     |     |     | 320 |
| Val | Asn | Ser | Ala | Ala | Phe | Pro | Ala | Pro | Ile | Glu | Lys | Thr | Ile | Ser | Lys |
|     |     |     |     | 325 |     |     |     |     | 330 |     |     |     |     | 335 |     |
| Thr | Lys | Gly | Arg | Pro | Lys | Ala | Pro | Gln | Val | Tyr | Thr | Ile | Pro | Pro | Pro |
|     |     |     | 340 |     |     |     |     | 345 |     |     |     |     | 350 |     |     |
| Lys | Glu | Gln | Met | Ala | Lys | Asp | Lys | Val | Ser | Leu | Thr | Cys | Met | Ile | Thr |
|     |     |     | 355 |     |     |     |     | 360 |     |     |     |     | 365 |     |     |
| Asp | Phe | Phe | Pro | Glu | Asp | Ile | Thr | Val | Glu | Trp | Gln | Trp | Asn | Gly | Gln |
|     | 370 |     |     |     |     | 375 |     |     |     |     | 380 |     |     |     |     |
| Pro | Ala | Glu | Asn | Tyr | Lys | Asn | Thr | Gln | Pro | Ile | Met | Asp | Thr | Asp | Gly |
| 385 |     |     |     |     | 390 |     |     |     |     | 395 |     |     |     |     | 400 |
| Ser | Tyr | Phe | Val | Tyr | Ser | Lys | Leu | Asn | Val | Gln | Lys | Ser | Asn | Trp | Glu |
|     |     |     |     | 405 |     |     |     |     | 410 |     |     |     |     | 415 |     |
| Ala | Gly | Asn | Thr | Phe | Thr | Cys | Ser | Val | Leu | His | Glu | Gly | Leu | His | Asn |
|     |     |     | 420 |     |     |     |     | 425 |     |     |     |     | 430 |     |     |
| His | His | Thr | Glu | Lys | Ser | Leu | Ser | His | Ser | Pro | Gly | Lys |     |     |     |
|     |     | 435 |     |     |     |     | 440 |     |     |     |     | 445 |     |     |     |

( 2 ) INFORMATION FOR SEQ ID NO: 34:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 34:

| Asp | Ile | Val | Met | Ser | Gln | Ser | Pro | Ser | Ser | Leu | Ala | Val | Ser | Ala | Gly |
|-----|-----|-----|-----|-----|-----|-----|-----|-----|-----|-----|-----|-----|-----|-----|-----|
| 1 |   |   |   | 5 |   |   |   |   | 10 |   |   |   |   | 15 |   |
| Glu | Lys | Val | Thr | Met | Ser | Cys | Lys | Ser | Ser | Gln | Ser | Leu | Leu | Asn | Ser |
|   |   |   | 20 |   |   |   |   | 25 |   |   |   |   | 30 |   |   |

```
Arg  Thr  Arg  Lys  Asn  Tyr  Leu  Ala  Trp  Tyr  Gln  Gln  Arg  Pro  Gly  Gln
          35                      40                           45

Ser  Pro  Lys  Leu  Leu  Ile  Tyr  Trp  Ala  Ser  Thr  Arg  Thr  Ser  Gly  Val
     50                      55                           60

Pro  Asp  Arg  Phe  Thr  Gly  Ser  Gly  Ser  Gly  Thr  Asp  Phe  Thr  Leu  Thr
65                       70                      75                           80

Ile  Ser  Ser  Val  Gln  Ala  Glu  Asp  Leu  Ala  Ile  Tyr  Tyr  Cys  Lys  Gln
                    85                      90                          95

Ser  Tyr  Thr  Leu  Arg  Thr  Phe  Gly  Gly  Gly  Thr  Lys  Leu  Glu  Ile  Lys
               100                      105                     110

Arg  Ala  Asp  Ala  Ala  Pro  Thr  Val  Ser  Ile  Phe  Pro  Pro  Ser  Ser  Glu
          115                      120                     125

Gln  Leu  Thr  Ser  Gly  Gly  Ala  Ser  Val  Val  Cys  Phe  Leu  Asn  Asn  Phe
     130                      135                     140

Tyr  Pro  Lys  Asp  Ile  Asn  Val  Lys  Trp  Lys  Ile  Asp  Gly  Ser  Glu  Arg
145                      150                     155                          160

Gln  Asn  Gly  Val  Leu  Asn  Ser  Trp  Thr  Asp  Gln  Asp  Ser  Lys  Asp  Ser
                    165                     170                     175

Thr  Tyr  Ser  Met  Ser  Ser  Thr  Leu  Thr  Leu  Thr  Lys  Asp  Glu  Tyr  Glu
               180                     185                     190

Arg  His  Asn  Ser  Tyr  Thr  Cys  Glu  Ala  Thr  His  Lys  Thr  Ser  Thr  Ser
          195                     200                     205

Pro  Ile  Val  Lys  Ser  Phe  Asn  Arg  Asn  Glu  Cys
     210                     215
```

(2) INFORMATION FOR SEQ ID NO: 35:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
AATTCGAGCT GGATCCTTAT TACCGTTTGA TCATTATTAA TTCAGATCCT CTTCTGAGAT    60
GAGTTTTTGT TCCCGTTTGA TC                                             82
```

(2) INFORMATION FOR SEQ ID NO: 36:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 36:

```
Met  Gly  Trp  Ser  Tyr  Ile  Ile  Leu  Phe  Leu  Val  Ala  Thr  Gly  Thr  Asp
1              5                       10                      15

Val  His  Ser  Gln  Val  Gln  Leu  Gln  Gln  Pro  Gly  Ala  Glu  Leu  Val  Lys
          20                      25                          30

Pro  Gly  Ala  Ser  Val  Gln  Leu  Ser  Cys  Lys  Ala  Ser  Gly  Tyr  Thr  Phe
          35                      40                          45

Thr  Gly  Tyr  Trp  Ile  His  Trp  Val  Lys  Gln  Arg  Pro  Gly  Gln  Gly  Leu
     50                      55                           60

Glu  Trp  Ile  Gly  Glu  Val  Asn  Pro  Ser  Thr  Gly  Arg  Ser  Asp  Tyr  Asn
```

-continued

| | | | | | | | | | | | | | | |
|---|---|---|---|---|---|---|---|---|---|---|---|---|---|---|
| 65 | | | | | 70 | | | | 75 | | | | | 80 |
| Glu | Lys | Phe | Lys | Asn 85 | Lys | Ala | Thr | Leu 90 | Thr | Val | Asp | Lys | Ser 95 | Ser | Thr |
| Thr | Ala | Tyr | Met 100 | Gln | Leu | Ser | Ser | Leu 105 | Thr | Ser | Glu | Asp | Ser 110 | Ala | Val |
| Tyr | Tyr | Cys 115 | Ala | Arg | Glu | Arg | Ala 120 | Tyr | Gly | Tyr | Asp | Asp 125 | Ala | Met | Asp |
| Tyr | Trp 130 | Gly | Gln | Gly | Thr | Ser 135 | Val | Thr | Val | Ser | Ser 140 | Ala | Lys | Thr | Thr |
| Pro 145 | Pro | Ser | Val | Tyr | Pro 150 | Leu | Ala | Pro | Gly | Ser 155 | Ala | Ala | Gln | Thr | Asn 160 |
| Ser | Met | Val | Thr | Leu 165 | Gly | Cys | Leu | Val | Lys 170 | Gly | Tyr | Phe | Pro | Glu 175 | Pro |
| Val | Thr | Val | Thr 180 | Trp | Asn | Ser | Gly | Ser 185 | Leu | Ser | Ser | Gly | Val 190 | His | Thr |
| Phe | Pro | Ala 195 | Val | Leu | Gln | Ser | Asp 200 | Leu | Tyr | Thr | Leu | Ser 205 | Ser | Ser | Val |
| Thr | Val 210 | Pro | Ser | Ser | Thr | Trp 215 | Pro | Ser | Glu | Thr | Val 220 | Thr | Cys | Asn | Val |
| Ala 225 | His | Pro | Ala | Ser | Ser 230 | Thr | Lys | Val | Asp | Lys 235 | Lys | Ile | Val | Pro | Arg 240 |
| Asp | Cys | Gly | Cys | Lys 245 | Pro | Cys | Ile | Cys | Thr 250 | Val | Pro | Glu | Val | Ser 255 | Ser |
| Val | Phe | Ile | Phe 260 | Pro | Pro | Lys | Pro | Lys 265 | Asp | Val | Leu | Thr | Ile 270 | Thr | Leu |
| Thr | Pro | Lys 275 | Val | Thr | Cys | Val | Val 280 | Val | Asp | Ile | Ser | Lys 285 | Asp | Asp | Pro |
| Glu | Val 290 | Gln | Phe | Ser | Trp | Phe 295 | Val | Asp | Asp | Val | Glu 300 | Val | His | Thr | Ala |
| Gln 305 | Thr | Gln | Pro | Arg | Glu 310 | Glu | Gln | Phe | Asn | Ser 315 | Thr | Phe | Arg | Ser | Val 320 |
| Ser | Glu | Leu | Pro | Ile 325 | Met | His | Gln | Asp | Trp 330 | Leu | Asn | Gly | Lys | Glu 335 | Phe |
| Lys | Cys | Arg | Val 340 | Asn | Ser | Ala | Ala | Phe 345 | Pro | Ala | Pro | Ile | Glu 350 | Lys | Thr |
| Ile | Ser | Lys 355 | Thr | Lys | Gly | Arg | Pro 360 | Lys | Ala | Pro | Gln | Val 365 | Tyr | Thr | Ile |
| Pro | Pro 370 | Pro | Lys | Glu | Gln | Met 375 | Ala | Lys | Asp | Lys | Val 380 | Ser | Leu | Thr | Cys |
| Met 385 | Ile | Thr | Asp | Phe | Phe 390 | Pro | Glu | Asp | Ile | Thr 395 | Val | Glu | Trp | Gln | Trp 400 |
| Asn | Gly | Gln | Pro | Ala 405 | Glu | Asn | Tyr | Lys | Asn 410 | Thr | Gln | Pro | Ile | Met 415 | Asp |
| Thr | Asp | Gly | Ser 420 | Tyr | Phe | Val | Tyr | Ser 425 | Lys | Leu | Asn | Val | Gln 430 | Lys | Ser |
| Asn | Trp | Glu 435 | Ala | Gly | Asn | Thr | Phe 440 | Thr | Cys | Ser | Val | Leu 445 | His | Glu | Gly |
| Leu | His 450 | Asn | His | His | Thr | Glu 455 | Lys | Ser | Leu | Ser | His 460 | Ser | Pro | Gly | Lys |

( 2 ) INFORMATION FOR SEQ ID NO: 37:

( i ) SEQUENCE CHARACTERISTICS:
        ( A ) LENGTH: 239 amino acids
        ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO: 37:

| Met | Asp | Ser | Gln | Ala | Gln | Val | Leu | Ile | Leu | Leu | Leu | Trp | Val | Ser |
|---|---|---|---|---|---|---|---|---|---|---|---|---|---|---|
| 1 | | | | 5 | | | | 10 | | | | | | 15 |
| Gly | Thr | Cys | Gly | Asp | Ile | Val | Met | Ser | Gln | Ser | Pro | Ser | Ser | Leu | Ala |
| | | | 20 | | | | 25 | | | | | 30 | | |
| Val | Ser | Ala | Gly | Glu | Lys | Val | Thr | Met | Ser | Cys | Lys | Ser | Ser | Gln | Ser |
| | | 35 | | | | | 40 | | | | | 45 | | | |
| Leu | Leu | Asn | Ser | Arg | Thr | Arg | Lys | Asn | Tyr | Leu | Ala | Trp | Tyr | Gln | Gln |
| | 50 | | | | | 55 | | | | | 60 | | | | |
| Arg | Pro | Gly | Gln | Ser | Pro | Lys | Leu | Leu | Ile | Tyr | Trp | Ala | Ser | Thr | Arg |
| 65 | | | | | 70 | | | | | 75 | | | | | 80 |
| Thr | Ser | Gly | Val | Pro | Asp | Arg | Phe | Thr | Gly | Ser | Gly | Ser | Gly | Thr | Asp |
| | | | | 85 | | | | | 90 | | | | | 95 | |
| Phe | Thr | Leu | Thr | Ile | Ser | Ser | Val | Gln | Ala | Glu | Asp | Leu | Ala | Ile | Tyr |
| | | | 100 | | | | | 105 | | | | | 110 | | |
| Tyr | Cys | Lys | Gln | Ser | Tyr | Thr | Leu | Arg | Thr | Phe | Gly | Gly | Gly | Thr | Lys |
| | | 115 | | | | | 120 | | | | | 125 | | | |
| Leu | Glu | Ile | Lys | Arg | Ala | Asp | Ala | Ala | Pro | Thr | Val | Ser | Ile | Phe | Pro |
| | 130 | | | | | 135 | | | | | 140 | | | | |
| Pro | Ser | Ser | Glu | Gln | Leu | Thr | Ser | Gly | Gly | Ala | Ser | Val | Val | Cys | Phe |
| 145 | | | | | 150 | | | | | 155 | | | | | 160 |
| Leu | Asn | Asn | Phe | Tyr | Pro | Lys | Asp | Ile | Asn | Val | Lys | Trp | Lys | Ile | Asp |
| | | | | 165 | | | | | 170 | | | | | 175 | |
| Gly | Ser | Glu | Arg | Gln | Asn | Gly | Val | Leu | Asn | Ser | Trp | Thr | Asp | Gln | Asp |
| | | | 180 | | | | | 185 | | | | | 190 | | |
| Ser | Lys | Asp | Ser | Thr | Tyr | Ser | Met | Ser | Ser | Thr | Leu | Thr | Leu | Thr | Lys |
| | | 195 | | | | | 200 | | | | | 205 | | | |
| Asp | Glu | Tyr | Glu | Arg | His | Asn | Ser | Tyr | Thr | Cys | Glu | Ala | Thr | His | Lys |
| | 210 | | | | | 215 | | | | | 220 | | | | |
| Thr | Ser | Thr | Ser | Pro | Ile | Val | Lys | Ser | Phe | Asn | Arg | Asn | Glu | Cys |
| 225 | | | | | 230 | | | | | 235 | | | | | |

We claim:

1. An antigen binding structure having complementarity determining regions (CDRs) recognising antigen CA55.1 in which the CDRs have the following sequences:

a) heavy chain
CDR1 G Y W I H (SEQ ID NO: 27)
CDR2 E V N P S T G R S D Y N E K F K N (SEQ ID NO: 28)
CDR3 E R A Y G Y D D A M D Y (SEQ ID NO: 29)

b) light chain
CDR1 K S S Q S L L N S R T R K N Y L A (SEQ ID NO: 30)
CDR2 W A S T R T S (SEQ ID NO: 31)
CDR3 K Q S Y T L R T (SEQ ID NO: 32)
or a conservative analogue thereof.

2. An antigen binding structure having the following structure:

a heavy chain sequence (SEQ ID NO: 33)

Gln Val Gln Leu Gln Gln Pro Gly Ala Glu Leu Val Lys Pro Gly Ala

Ser Val Gln leu Ser Cys Lys Ala Ser Gly Tyr Thr Phe Thr Gly Tyr

Trp Ile His Trp Val Lys Gln Arg Pro Gly Gln Gly Leu Glu Trp Ile

Gly Glu Val Asn Pro Ser Thr Gly Arg Ser Asp Tyr Asn Glu Lys Phe

-continued

Lys Asn Lys Ala Thr Leu Thr Val Asp Lys Ser Ser Thr Thr Ala Tyr

Met Gln Leu Ser Ser Leu Thr Ser Glu Asp Ser Ala Val Tyr Tyr Cys

Ala Arg Glu Arg Ala Tyr Gly Tyr Asp Asp Ala Met Asp Tyr Trp Gly

Gln Gly Thr Ser Val Thr Val Ser Ser Ala Lys Thr Thr Pro Pro Ser

Val Tyr Pro Leu Ala Pro Gly Ser Ala Ala Gln Thr Asn Ser Met Val

Thr Leu Gly Cys Leu Val Lys Gly Tyr Phe Pro Glu Pro Val Thr Val

Thr Trp Asn Ser Gly Ser Leu Ser Ser Gly Val His Thr Phe Pro Ala

Val Leu Gln Ser Asp Leu Tyr Thr Leu Ser Ser Ser Val Thr Val Pro

Ser Ser Thr Trp Pro Ser Glu Thr Val Thr Cys Asn Val Ala His Pro

Ala Ser Ser Thr Lys Val Asp Lys Lys Ile Val Pro Arg Asp Cys Gly

Cys Lys Pro Cys Ile Cys Thr Val Pro Glu Val Ser Ser Val Phe Ile

Phe Pro Pro Lys Pro Lys Asp Val Leu Thr Ile Thr Leu Thr Pro Lys

Val Thr Cys Val Val Val Asp Ile Ser Lys Asp Asp Pro Glu Val Gln

Phe Ser Trp Phe Val Asp Asp Val Glu Val His Thr Ala Gln Thr Gln

Pro Arg Glu Glu Gln Phe Asn Ser Thr Phe Arg Ser Val Ser Glu Leu

Pro Ile Met His Gln Asp Trp Leu Asn Gly Lys Glu Phe Lys Cys Arg

Val Asn Ser Ala Ala Phe Pro Ala Pro Ile Glu Lys Thr Ile Ser Lys

Thr Lys Gly Arg Pro Lys Ala Pro Gln Val Tyr Thr Ile Pro Pro Pro

Lys Glu Gln Met Ala Lys Asp Lys Val Ser Leu Thr Cys Met Ile Thr

Asp Phe Phe Pro Glu Asp Ile Thr Val Glu Trp Gln Trp Asn Gly Gln

Pro Ala Glu Asn Tyr Lys Asn Thr Gln Pro Ile Met Asp Thr Asp Gly

Ser Tyr Phe Val Tyr Ser Lys Leu Asn Val Gln Lys Ser Asn Trp Glu

Ala Gly Asn Thr Phe Thr Cys Ser Val Leu His Glu Gly Leu His Asn

His His Thr Glu Lys Ser Leu Ser His Ser Pro Gly Lys and;

a light chain sequence (SEQ ID NO: 34):

Asp Ile Val Met Ser Gln Ser Pro Ser Ser Leu Ala Val Ser Ala Gly

Glu Lys Val Thr Met Ser Cys Lys Ser Ser Gln Ser Leu Leu Asn Ser

Arg Thr Arg Lys Asn Tyr Leu Ala Trp Tyr Gln Gln Arg Pro Gly Gln

-continued

Ser Pro Lys Leu Leu Ile Tyr Trp Ala Ser Thr Arg Thr Ser Gly Val

Pro Asp Arg Phe Thr Gly Ser Gly Ser Gly Thr Asp Phe Thr Leu Thr

Ile Ser Ser Val Gln Ala Glu Asp Leu Ala Ile Tyr Tyr Cys Lys Gln

Ser Tyr Thr Leu Arg Thr Phe Gly Gly Gly Thr Lys Leu Glu Ile Lys

Arg Ala Asp Ala Ala Pro Thr Val Ser Ile Phe Pro Pro Ser Ser Glu

Gln Leu Thr Ser Gly Gly Ala Ser Val Val Cys Phe Leu Asn Asn Phe

Tyr Pro Lys Asp Ile Asn Val Lys Trp Lys Ile Asp Gly Ser Glu Arg

Gln Asn Gly Val Leu Asn Ser Trp Thr Asp Gln Asp Ser Lys Asp Ser

Thr Tyr Ser Met Ser Ser Thr Leu Thr Leu Thr Lys Asp Glu Tyr Glu

Arg His Asn Ser Tyr Thr Cys Glu Ala Thr His Lys Thr Ser Thr Ser

Pro Ile Val Lys Ser Phe Asn Arg Asn Glu Cys;

or any one of the following constructs thereof:

F(ab')2; F(ab'), Fab, Fv, single chain Fv & V-min or; a conservative analogue thereof.

3. The antigen binding structure of claim 2 wherein the structure is humanized.

4. A polynucleotide sequence encoding at least the variable region of the heavy chain or the light chain of an antigen binding structure as defined in any one of claims 1, 2 and 3.

5. An expression vector encoding at least the variable region of the heavy or light chain of an antigen binding structure as defined in any one of claims 1, 2 and 3.

6. A host cell transformed with a polynucleotide sequence or a transgenic non-human animal or transgenic plant developed from the host cell in which the polynucloetide sequence encodes at least the variable region of the heavy chain or light chain of an antigen binding structure as defined in any one of claims 1, 2 and 3.

7. Hybridoma 55.1 deposited as ECACC deposit no. 93081901, variant cell lines thereof or antibody produced thereby.

8. ACEHRGSGWC phage deposited as NCIMB No. 40638 and variants thereof.

9. A method of making at least a variable region of a heavy or light chain of an antigen binding structure as defined in any one of claims 1, 2 and 3 comprising:

a) transforming a host cell with a polynucleotide sequence which encodes at least the variable region of the heavy or light chain of the antigen binding structure and optionally developing the transformed host cell into a transgenic non-human mammal or transgenic plant;

b) subjecting the host cell, transgenic non-human mammal or transgenic plant to conditions conducive to expression, and optionally secretion, of at least the variable region and optionally;

c) at least partially purifying the variable region.

10. A method according to claim 9 in which both heavy and light chain variable regions are expressed in the same cell and assembled thereby to form an antigen binding structure.

11. A method of making monoclonal antibody 55.1 comprising:

a) culturing hybridoma 55.1 deposited as ECACC deposit no. 93081901 in medium under conditions conducive to expression of antibody therefrom and;

b) obtaining antibody 55.1 from the culture medium and optionally;

c) preparing a F(ab')2 fragment of antibody 55.1 by enzymic digestion.

12. An immunotoxin conjugate which comprises a toxin and an antigen binding structure as defined in any one of claims 1, 2 and 3.

13. A pharmaceutical composition comprising an immunotoxin conjugate which comprises a toxin and an antigen binding structure as defined in any one of claims 1, 2 and 3, and a pharmaceutically acceptable diluent or carrier.

14. A method of targeting a toxin to cells displaying antigen CA55.1 in a mammal in need of such targetting which comprises administration of a pharmaceutically effective amount of an immunotoxin conjugate which comprises a toxin and an antigen binding structure as defined in any one of claims 1, 2 and 3.

15. A diagnostic method comprising contacting an antigen binding structure of any one of claims 1, 2 and 3 with a sample under conditions which permit the formation of an antigen binding structure-antigen complex and detecting the presence of the antigen binding structure-antigen complex.

* * * * *